(12) United States Patent
Garcia-Guzman Blanco et al.

(10) Patent No.: US 7,563,795 B2
(45) Date of Patent: Jul. 21, 2009

(54) PHENYL-PIPERAZINE DERIVATIVES AS MODULATORS OF MUSCARINIC RECEPTORS

(75) Inventors: Miguel Garcia-Guzman Blanco, San Diego, CA (US); Daniele Bergeron, La Mesa, CA (US); Peter D. J. Grootenhuis, San Diego, CA (US); Dennis Hurley, San Marcos, CA (US); Akiko Nakatani, San Diego, CA (US); Lewis R. Makings, Enchintas, CA (US); Daniel DiSepio, Carlsbad, CA (US); Gabriel Raffai, Perris, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 459 days.

(21) Appl. No.: 10/951,242

(22) Filed: Sep. 27, 2004

(65) Prior Publication Data

US 2005/0137211 A1 Jun. 23, 2005

Related U.S. Application Data

(60) Provisional application No. 60/506,585, filed on Sep. 26, 2003.

(51) Int. Cl.
*A61K 31/4965* (2006.01)
*C07D 241/04* (2006.01)
*C07D 295/00* (2006.01)
(52) U.S. Cl. .................................. 514/255.03; 544/392
(58) Field of Classification Search ................. 544/392; 514/255.03
See application file for complete search history.

(56) References Cited

U.S. PATENT DOCUMENTS

| | | | |
|---|---|---|---|
| 3,146,235 A | 8/1964 | Gust | |
| 3,309,370 A | 3/1967 | Schut | |
| 3,354,161 A | 11/1967 | Schut | |
| 3,391,142 A | 7/1968 | Eriks et al. | |
| 3,598,825 A | 8/1971 | Biel et al. | |
| 3,689,490 A | 9/1972 | Schut | |
| 3,716,538 A | 2/1973 | Schut | |
| 3,726,872 A | 4/1973 | Schut | |
| 3,792,053 A | 2/1974 | Potoski et al. | |
| 4,203,986 A | 5/1980 | Joullie et al. | |
| 4,518,712 A | 5/1985 | Fujimura et al. | |
| 5,192,775 A | 3/1993 | Malen et al. | |
| 5,254,548 A | 10/1993 | Wermuth et al. | |
| 5,332,732 A | 7/1994 | Scott et al. | |
| 5,589,477 A | 12/1996 | Chokai et al. | |
| 5,686,454 A | 11/1997 | Bock et al. | |
| 6,197,772 B1 | 3/2001 | Janssens et al. | |
| 6,271,230 B1 | 8/2001 | Baker et al. | |
| 6,288,068 B1 | 9/2001 | Lowe et al. | |
| 6,420,559 B1 | 7/2002 | Anand et al. | |
| 6,436,962 B1 | 8/2002 | Hoffman et al. | |
| 6,498,168 B2 | 12/2002 | Lowe et al. | |
| 6,635,764 B2 | 10/2003 | Mammen et al. | |
| 6,693,202 B1 | 2/2004 | Aggen et al. | |
| 6,713,479 B2 | 3/2004 | Persons et al. | |
| 6,727,249 B2 | 4/2004 | Curtis et al. | |
| 2002/0103205 A1 | 8/2002 | Lowe et al. | |
| 2003/0181446 A1 | 9/2003 | Leonardi et al. | |
| 2003/0185869 A1 | 10/2003 | Wertz et al. | |
| 2003/0232839 A1 | 12/2003 | Hangauer et al. | |
| 2004/0048913 A1 | 3/2004 | Gao et al. | |
| 2004/0110947 A1 | 6/2004 | Chandrakumar | |
| 2004/0142904 A1 | 7/2004 | Rariy et al. | |
| 2004/0186142 A1 | 9/2004 | Taveras et al. | |
| 2006/0019962 A1* | 1/2006 | Makings et al. | ........ 514/252.11 |

FOREIGN PATENT DOCUMENTS

| | | |
|---|---|---|
| DE | 10161809 | 6/2003 |
| EP | 0050072 | 4/1982 |
| EP | 0368188 A1 | 5/1990 |
| EP | 0503411 A1 | 9/1992 |
| EP | 0545095 | 6/1993 |
| EP | 0841330 A1 | 5/1998 |
| FR | 2687401 | 8/1993 |
| WO | WO 9412495 A1 | 6/1994 |
| WO | WO 9415928 | 7/1994 |
| WO | WO 0035878 A1 | 6/2000 |
| WO | WO 2002083863 | 10/2002 |
| WO | WO 2003089410 | 10/2003 |
| WO | WO 2004006836 | 1/2004 |
| WO | WO 04069794 A2 | 8/2004 |

OTHER PUBLICATIONS

Boido, Caterina Canu and Sparatore, Fabio. "Synthesis and preliminary pharmacological evaluation of some cystisine derivatives." Journal: IL Farmaco, vol. 54, Apr. 23, 1999, pp. 438-451.

(Continued)

*Primary Examiner*—James O Wilson
*Assistant Examiner*—Erich A Leeser
(74) *Attorney, Agent, or Firm*—Honigan Miller Schwartz and Cohn LLP; Andrew N. Weber; Jonathan P. O'Brien

(57) ABSTRACT

The present invention relates to modulators of muscarinic receptors. The present invention also provides compositions comprising such modulators, and methods therewith for treating muscarinic receptor mediated diseases.

22 Claims, No Drawings

OTHER PUBLICATIONS

Caulfield, M. P. et al., "Muscarine Receptors—Characterization, Coupling, and Function," Pharmacol. Ther., vol. 58, (1993), pp. 319-379.

Caulfield, M. P. et al., International Union of Pharmacology. XVII. "Classification of Muscarinic Acetylcholine Receptors," Pharmacol. Rev., vol. 50, (1998), pp. 279-290.

Chernyavsky, Alex I. et al., "Novel signaling pathways mediating reciprocal control of keratinocyte migration and wound epithelizlization through M3 and M4 muscarinic recptors." The Journal of Cell Biology, vol. 166, No. 2, Jul. 19, 2004, pp. 261-272.

Delapp, N. et al., "Therapeutic Opportunities for Muscsrinic Receptors in the Central Nervous System," Journal of Medicinal Chemistry, vol. 43, No. 23, (2000), pp. 4333-4353.

Germane, S. and Karina, L., "Effect of N-[1-adamantylmethy]-N'-substituted piperazine dihydrochlorides on the central nervous system." Jounal: Khimiko-Farmatsevticheskii Zhurnal, vol. 12, No. 6, (1978), pp. 95-99.

Hulme, E. C. et al., "Muscarinic Receptor Subtypes," Ann. Rev. Pharmacol. Toxicol., vol. 30, (1990), pp. 633-673.

Kaiser, Carl, et al., "Synthesis and antimuscarinic properties of some N-substituted 5-(aminomethyl) -3, 3-diphenyl-2 (3H)—furanones." Journal of Medicinal Chemistry, vol. 35, No. 23, Jun. 26, 1992, pp. 4415-4424.

Limbeck, Marcus and Gundisch, Daniela. "Tetrahydrofuranylmethylamines: An efficient and simple one-step synthesis and biological activities." Journal of Heterocyclic Chemistry, vol. 40, No. 5, (2003), pp. 895-900.

Lopez-Rodriguez, Maria L., et al., "Design and synthesis of new benzimidazole-arhypiprazine acting as mixed 5-HT1A/5-HT3 ligands." Journal: Bioorganic & Medicinal Chemistry Letters, vol. 13, Jul. 1, 2003, pp. 3177-3180.

Minardi, Giovanna and Schenone, Pietro. "N-substituted 3-aminomethylboman-2-ones." Journal: Farmaco, Edizione Scientifica, vol. 25, No. 7, (1970), pp. 519-532.

Rogers, G.A., et al., "Synthesis, in vitro acetycholine-storage-blocking activites, and biological properties of derivatives and analogues of trans-2-(4-Phenylpiperidino) cyclohexanol (Vesamicol)" Journal of Medicinal Chemistry, vol. 32, No. 6, Jun. 1, 1989, pp. 1217-1230.

Schenone, Pietro; Tasca, Antonietta; Bignardi, Gaetano; and Mosti, Luisa, "N, N-disubstituted 10-amino-2-exo-bornanols and related esters." European Journal of Medicinal Chemistry, vol. 10, No. 4, (1975), pp. 412-417.

Zlokarnik, G; Negulescu, P.A.; Knapp, T. E.; Mere, L; Burres, N; Feng, L; Whitney. M; Roemer, K; Tsien, R.Y. "Quantitation of transcription and clonal selection of single living cells with␣-lactamase as reporter" Science, vol. 279, Jan. 2, 1998, pp. 84-88.

Chemical Library; May 15, 2002; XP002329724; RN: 415971-89-0; abstract.

Chemical Library; Oct. 30, 2002; XP002329725; RN: 467447-94-5; abstract.

Chemical Library; Oct. 29, 2002; XP002329726; RN: 467239-95-8; abstract.

Scott, MK, et al., "Pyrrole Mannich Bases as Potential Antipsychotic Agents" Journal of Medicinal Chemistry, American Chemical Society, (1992) vol. 35 No. 3 552-558.

International Search Report dated Feb. 2, 2005.

International Search Report dated Aug. 4, 2005.

Bando, Kazunori, et al.; "Piperazine analog of vesamicol: in vitro and in vivo characterization for vesicular acetylocholine transporter," Synapse (New York) (2000), 38(1), 27-37.

Chambers, Mark S., et al.; "Spiropiperidines As High-Affinity, Selective σ Ligands," Journal of Medicinal Chemistry (1992), 35(11), 2033-9.

Evans, Ben E., et al.; "Orally Active, Nonpeptide Oxytocin Antagonists," Journal of Medicinal Chemistry (1992), 35(21), 3919-27.

Mouithys-Mickalad, Ange, et al.; "Synthesis And Pharmacological Evaluation of 6-Piperidino- and 6-Piperazinoalkyl-23(3H)-Benzothizolones as Mixed σ/5-HTIA Ligands," Bioorganic & Medicinal Chemistry Letters (2002), 12(8), 1149-1152.

Sakamuri, Sukumar, et al., "Pharmacophore-Based Discovery, Synthesis, and Biological Evaluation of 4-Phenyl-1-arylalkyl Piperidines as Dopamine Transporter Inhibitors," Bioorganic & Medicinal Chemistry Letters, 2001, 11, 495.

Simpson, Merrill M., et al.; "Dopamine D4/D2 Receptor Selectivity Is Determined By A Divergent Aromatic Microdomain Contained Within The Second, Third, And Seventh Membrane-Spanning Segments," Molecular Pharmacology (1999), 56(6), 1116-1126.

* cited by examiner

PHENYL-PIPERAZINE DERIVATIVES AS MODULATORS OF MUSCARINIC RECEPTORS

This application claims priority under 35 U.S.C. §119(e) to U.S. Ser. No. 60/506,585 filed on Sep. 26, 2003.

TECHNICAL FIELD OF THE INVENTION

The present invention relates to modulators of muscarinic receptors. The present invention also provides compositions comprising such modulators, and methods therewith for treating muscarinic receptor mediated diseases.

BACKGROUND OF THE INVENTION

The neurotransmitter acetylcholine binds to two types of cholinergic receptors: the ionotropic family of nicotinic receptors and the metabotropic family of muscarinic receptors. Muscarinic receptors belong to the large superfamily of plasma membrane-bound G protein coupled receptors (GPCRs). To date, five subtypes of muscarinic receptors ($M_1$-$M_5$) have been cloned and sequenced from a variety of species, and show a remarkably high degree of homology across species and receptor subtype. These $M_1$-$M_5$ muscarinic receptors are predominantly expressed within the parasympathetic nervous system which exerts excitatory and inhibitory control over the central and peripheral tissues and participate in a number of physiologic functions, including heart rate, arousal, cognition, sensory processing, and motor control.

Muscarinic agonists such as muscarine and pilocarpine, and antagonists, such as atropine have been known for over a century, but little progress has been made in the discovery of receptor subtype-selective compounds, thereby making it difficult to assign specific functions to the individual receptors. See, e.g., DeLapp, N. et al., "Therapeutic Opportunities for Muscarinic Receptors in the Central Nervous System," *J. Med. Chem.*, 43(23), pp. 4333-4353 (2000); Hulme, E. C. et al., "Muscarinic Receptor Subtypes," *Ann. Rev. Pharmacol. Toxicol.*, 30, pp. 633-673 (1990); Caulfield, M. P. et al., "Muscarinic Receptors-Characterization, Coupling, and Function," *Pharmacol. Ther.*, 58, pp. 319-379 (1993); Caulfield, M. P. et al., International Union of Pharmacology. XVII. Classification of Muscarinic Acetylcholine Receptors," *Pharmacol. Rev.*, 50, pp. 279-290 (1998), the disclosures of which are incorporated herein by reference.

The Muscarinic family of receptors is the target of a large number of pharmacological agents used for various diseases, including leading drugs for COPD, asthma, urinary incontinence, glaucoma, Alzheimer's (AchE inhibitors), and Pain.

Pain can be roughly divided into three different types: acute, inflammatory, and neuropathic. Acute pain serves an important protective function in keeping the organism safe from stimuli that may produce tissue damage. Severe thermal, mechanical, or chemical inputs have the potential to cause severe damage to the organism if unheeded. Acute pain serves to quickly remove the individual from the damaging environment. Acute pain by its very nature generally is short lasting and intense. Inflammatory pain on the other had may last for much longer periods of time and it's intensity is more graded. Inflammation may occur for many reasons including tissue damage, autoimmune response, and pathogen invasion. Inflammatory pain is mediated by an "inflammatory soup" that consists of substance P, histamines, acid, prostaglandin, bradykinin, CGRP, cytokines, ATP, and neurotransmitter release. The third class of pain is neuropathic and involves nerve damage that results in reorganization of neuronal proteins and circuits yielding a pathologic "sensitized" state that can produce chronic pain lasting for years. This type of pain provides no adaptive benefit and is particularly difficult to treat with existing therapies.

Pain, particularly neuropathic and intractable pain is a large unmet medical need. Millions of individuals suffer from severe pain that is not well controlled by current therapeutics. The current drugs used to treat pain include NSAIDS, COX2 inhibitors, opioids, tricyclic antidepressants, and anticonvulsants. Neuropathic pain has been particularly difficult to treat as it does not respond well to opiods until high doses are reached. Gabapentin is currently the favored therapeutic for the treatment of neuropathic pain although it works in only 60% of patients where it shows modest efficacy. The drug is however very safe and side effects are generally tolerable although sedation is an issue at higher doses.

Despite the large therapeutic value of this family, cholinergic drugs are limited by the lack of selectivity of these agents, with significant activation of the parasympathetic autonomous system and elevated incidence of adverse effects. The molecular cloning of the muscarinic receptors and the identification of the physiological role of specific isoforms using knock-out mice, has recently delineated novel opportunities for selective muscarinic ligands, and has helped to define the selectivity profile that is required for enhanced efficacy and reduced side effects.

There is a need for modulators of muscarinic receptors $M_1$-$M_5$. There is also a need for methods for treating muscarinic receptor-mediated diseases.

There is also a need for modulators of muscarinic receptors that are selective as to subtypes $M_1$-$M_5$.

SUMMARY OF THE INVENTION

The present invention provides a method of modulating activity of a muscarinic receptor, comprising the step of contacting said receptor with a compound having the formula:

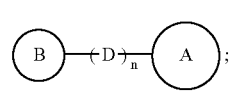
(I)

wherein:
B is selected from

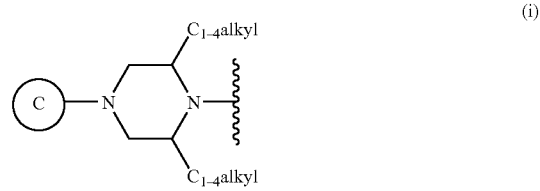
(i)

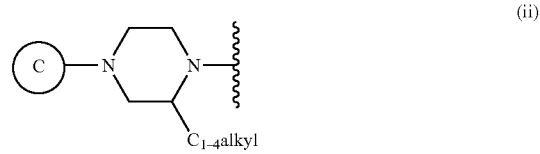
(ii)

-continued (iii)

[Structure: C—N(piperazine)N—]

D is CF$_2$, CH$_2$, or CHR$^9$;

Ring C is phenyl optionally substituted with 1 to 4 of R$^1$, R$^2$, R$^3$, R$^4$, or R$^5$;

Ring A is a 3-8 membered monocyclic carbocyclic ring, a 7-14 membered bicylic carbocyclic ring, a 7-14 tricyclic carbocyclic ring, a 3-8 membered monocyclic heterocyclic ring, a 7-14 membered bicylic heterocyclic ring, or a 7-14 tricyclic heterocyclic ring, in which the heterocyclic rings contain 1-5 atoms selected from O, S, and N;

wherein ring A contains up to 5 substituents independently selected from R$^1$, R$^2$, R$^3$, R$^4$, or R$^5$;

Each R$^1$ is independently oxo or ((C1-C4)aliphatic)$_m$-Q$^1$;

Each Q$^1$ is independently halo, CN, NO$_2$, CF$_3$, OCF$_3$, OH, SR$^6$, S(O)R$^6$, SO$_2$R$^6$, N(R$^6$)$_2$, NR$^6$R$^8$, COOH, COOR$^6$ or OR$^6$;

Each R$^2$ is independently aliphatic optionally substituted with 1-3 substituents independently selected from R$^1$, R$^4$, or R$^5$;

Each R$^3$ is independently a cycloaliphatic, aryl, heterocyclic, or heteroaryl ring, wherein each of the cycloaliphatic, aryl, heterocyclic, or heteroaryl are optionally substituted with 1-3 substituents independently selected from R$^1$, R$^2$, R$^4$, or R$^5$;

Each R$^4$ is independently OR$^5$, OR$^6$, OC(O)R$^6$, OC(O)R$^5$, OC(O)OR$^6$, OC(O)OR$^5$, OC(O)N(R$^6$)$_2$, OC(O)N(R$^5$)$_2$, OC(O)N(R$^6$R$^5$), S(O)$_i$R$^6$, S(O)$_i$R$^5$, SO$_2$N(R$^6$)$_2$, SO$_2$N(R$^5$)$_2$, SO$_2$NR$^5$R$^6$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^5$, C(O)N(OR$^5$)R$^6$, C(NOR$^6$)R$^6$, C(NOR$^6$)R$^5$, C(NOR$^5$)R$^6$, C(NOR$^5$)R$^5$, N(R$^6$)$_2$, N(R$^5$)$_2$, N(R$^5$R$^6$), NR$^5$C(O)R$^5$, NR$^6$C(O)R$^6$, NR$^6$C(O)R$^5$, NR$^6$C(O)OR$^6$, NR$^5$C(O)OR$^6$, NR$^6$C(O)OR$^5$, NR$^5$C(O)OR$^5$, NR$^6$C(O)N(R$^6$)$_2$, NR$^6$C(O)NR$^5$R$^6$, NR$^6$C(O)N(R$^5$)$_2$, NR$^5$C(O)N(R$^6$)$_2$, NR$^5$C(O)NR$^5$R$^6$, NR$^5$C(O)N(R$^5$)$_2$, NR$^6$SO$_2$R$^6$, NR$^6$SO$_2$R$^5$, NR$^5$SO$_2$R$^5$, NR$^6$SO$_2$N(R$^6$)$_2$, NR$^6$SO$_2$NR$^5$R$^6$, NR$^6$SO$_2$N(R$^5$)$_2$, NR$^5$SO$_2$NR$^5$R$^6$, NR$^5$SO$_2$N(R$^5$)$_2$, N(OR$^6$)R$^6$, N(OR$^6$)R$^5$, N(OR$^5$)R$^5$, or N(OR$^5$)R$^6$;

Each R$^5$ is independently a cycloaliphatic, aryl, heterocyclic, or heteroaryl ring, wherein each of the cycloaliphatic, aryl, heterocyclic, or heteroaryl are optionally substituted with 1 to 3 of R$^1$;

Each R$^6$ is independently H or aliphatic optionally substituted with R$^7$;

Each R$^7$ is independently a cycloaliphatic, aryl, heterocyclic, or heteroaryl ring, wherein each of the cycloaliphatic, aryl, heterocyclic, or heteroaryl are optionally substituted with 1 to 2 of (C$_1$-C$_6$)-straight or branched alkyl, (C$_2$-C$_6$) straight or branched alkenyl or alkynyl, 1,2-methylenedioxy, 1,2-ethylenedioxy, or (CH$_2$)$_n$-Q$^2$;

Each Q$^2$ is independently selected from halo, CN, NO$_2$, CF$_3$, OCF$_3$, OH, S-aliphatic, S(O)-aliphatic, SO$_2$-aliphatic, COOH, C(O)O-aliphatic, or O-aliphatic;

Each R$^8$ is independently an amino protecting group;

Each R$^9$ is independently R$^2$, R$^3$, or R$^6$;

Each i is independently 0, 1, 2, or 3;

Each m is independently 0 or 1; and

Each n is independently 0 or 1;

further provided that (i) when n is 1, D is CH$_2$, C is phenyl, and B is piperazine then ring A is not

[Structure: furanone with two Ph groups]

(ii) when n is 1, D is CH$_2$, C is phenyl, and B is piperazine then ring A is not

[Structure: tetrahydrofuran]

(iii) when n is 0, C is phenyl, and B is piperazine then ring A is not

[Structure: tetrahydronaphthalene with OH]

(iv) when n is 1, D is CH$_2$, ring A is 1,2,3,4 tetrahydroquinoline optionally substituted with R$^4$, and B is piperazine, then C is not phenyl substituted with halo, phenyl substituted with —OCH$_3$, or phenyl substituted with halo and —OCH$_3$;

(v) when n is 1, D is CH$_2$, ring A is

[Structures: piperidine-N-R$^{20}$ and piperidine-NH]

in which R$^{20}$ is —C(O)R$^5$, —C(O)R6, —C(O)OR5, C(O)OR6, and B is piperazine, then C is not phenyl optionally substituted with halo or —OCH$_3$.

The present invention also provides compounds of formula (I), compositions comprising compounds of formula (I), and methods of treating muscarinic receptor mediated diseases using compounds of formula (I).

Advantageously, the compounds of the invention unexpectedly modulate muscarinic receptors.

DETAILED DESCRIPTION OF THE INVENTION

As used herein, the following definitions shall apply unless otherwise indicated.

The term "muscarinic receptor," without a prefix specifying the receptor subtype, refers to one or more of the five receptor subtypes $M_1$-$M_5$.

The term "modulating" as used herein means increasing or decreasing, e.g. activity, by a measurable amount. Compounds that modulate muscarinic activity by increasing the activity of the muscarinic receptors are called agonists. Compounds that modulate muscarinic activity by decreasing the activity of the muscarinic receptors are called antagonists. An agonist interacts with a muscarinic receptor to increase the ability of the receptor to transduce an intracellular signal in response to endogenous ligand binding. An antagonist interacts with a muscarinic receptor and competes with the endogenous ligand(s) or substrate(s) for binding site(s) on the receptor to decrease the ability of the receptor to transduce an intracellular signal in response to endogenous ligand binding.

The phrase "treating or reducing the severity of a muscarinic receptor mediated disease" refers both to treatments for diseases that are directly caused by muscarinic activities and alleviation of symptoms of diseases not directly caused by muscarinic activities. Examples of diseases whose symptoms may be affected by muscarinic activity include, but are not limited to, CNS derived pathologies including cognitive disorders, Attention Deficit Hyperactivity Disorder (ADHD), obesity, Alzheimer's disease, various dementias such as vascular dementia, psychosis including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, bradhycardia, gastric acid secretion, asthma, GI disturbances and wound healing.

The phrase "optionally substituted" is used interchangeably with the phrase "substituted or unsubstituted."

The term "aliphatic" or "aliphatic group", as used herein, means a straight-chain or branched, substituted or unsubstituted hydrocarbon chain that is completely saturated (alkyl) or is unsaturated (alkenyl or alkynyl). Unless otherwise specified, an aliphatic group has 1 to 12 carbon atoms, preferably, 1-6 carbon atoms, and more preferably, 1-4 carbon atoms. Up to three, and preferably two, —CH$_2$— in said aliphatic may be replaced with O, S, or —NR$^6$.

The term "cycloaliphatic" means a saturated or partially unsaturated monocyclic or bicyclic hydrocarbon ring that has a single point of attachment to the rest of the molecule. Unless otherwise specified, preferred cycloaliphatic rings are 3-8 membered monocyclic rings, more preferably 3-6, and even more preferably, 3, 5, or 6. Also preferred, unless otherwise specified, are 8-12 membered bicyclic hydrocarbon rings, more preferably 10 membered bicyclic hydrocarbon rings.

The term "heteroatom," unless otherwise specified, means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or as in N-substituted pyrrolidinyl.

The term "unsaturated", as used herein, means a double bond or a triple bond. Each such bond constitutes one unit of unsaturation.

The term "aryl" used alone or as part of a larger moiety as in "aralkyl", "aralkoxy", or "aryloxyalkyl", refers to monocyclic, bicyclic and tricyclic aromatic carbocyclic ring systems. Unless otherwise specified, preferred aryl rings have a total of five to fourteen ring members, wherein at least one ring, if bicyclic or tricyclic, in the system is aromatic and wherein each ring in the system contains up to 6 ring members. The term "aryl" may be used interchangeably with the term "aryl ring". Phenyl is an example of aryl.

The term "heterocycle", "heterocyclyl", or "heterocyclic" as used herein means non-aromatic, monocyclic, bicyclic or tricyclic ring systems wherein one or more ring members is a heteroatom. Unless otherwise specified, each ring in the system preferably contains 3 to 7 ring members with preferably 1-3 heteroatoms.

The term "heteroaryl", used alone or as part of a larger moiety as in "heteroaralkyl" or "heteroarylalkoxy", refers to monocyclic, bicyclic and tricyclic ring systems, wherein at least one ring in the system is aromatic, and at least one ring in the system contains one or more heteroatoms. Unless otherwise specified, such ring systems preferably have a total of 5 to 15 ring members, wherein each ring in the system preferably contains 3 to 7 ring members, with preferably 1-3 heteroatoms. The term "heteroaryl" may be used interchangeably with the term "heteroaryl ring" or the term "heteroaromatic".

The term "amino protecting group" refers to a suitable chemical group that may be attached to a nitrogen atom. The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

A combination of substituents or variables is permissible only if such a combination results in a stable or chemically feasible compound. A stable compound or chemically feasible compound is one that is not substantially altered when kept at a temperature of 40° C. or less, in the absence of moisture, light, or other chemically reactive conditions, for at least a week.

According to one embodiment, the present invention provides a method of modulating activity of a muscarinic receptor, comprising the step of contacting said receptor with a compound having the formula (IA):

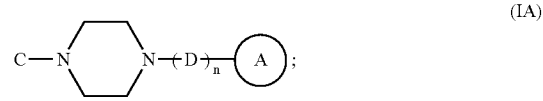

(IA)

wherein:

D is CF$_2$, CH$_2$, or CHR$^9$, S(O), S(O)$_2$, C(O);

Ring A is a 3-8 membered monocyclic or 7-14 membered bicylic aryl, a 3-8 membered monocyclic or 7-14 membered bicylic heteroaryl, a 3-8 membered monocyclic or 7-14 membered bicylic or tricyclic carbocyclic ring, or a 3-8 membered monocyclic or 7-14 membered bicylic or tricyclic heterocyclic ring containing 1-5 atoms selected from O, S, and N;

in which ring A contains up to 5 substituents independently selected from R$^1$, R$^2$, R$^3$, R$^4$, or R$^5$; and Each of C, R1, R2, R3, R4, R5, R6, R7, R8, R9, and n are defined above as in formula I.

Embodiments of this aspect of the invention include one or more of the following.

D is CF$_2$, CH$_2$, CHR$^9$, or C(O). D is D is CF$_2$, CH$_2$, CHR$^9$. D is CH$_2$ or C(O), or D is CH$_2$ or CF$_2$. D is CH$_2$. D is C(O). n is 0. n is 1.

The methods of the present invention employ compounds of formula (IA) provided that in formula (IA) one or more of the following:

(i) when n is 0 and C is phenyl, then ring A is not

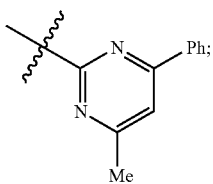

(ii) when n is 0 and C is not 3-chlorophenyl, then ring A is not

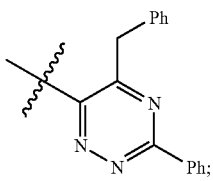

(iii) when n is 0 and C is

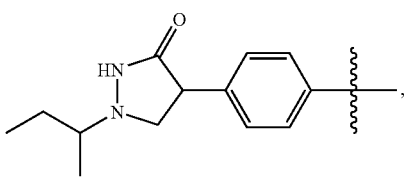

then ring A is not

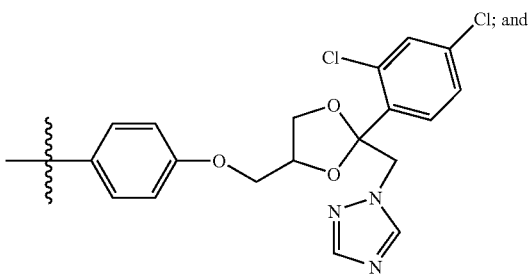

and (iv) when n is 0 and C is 2-methoxyphenyl, then ring A is not

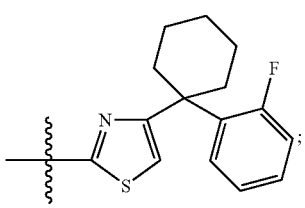

(v) when n is 1, D is CH$_2$, and C is 4-chlorophenyl, then ring A is not

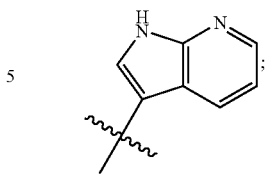

(vi) when n is 1, D is CH$_2$, and C is phenyl, then ring A is not

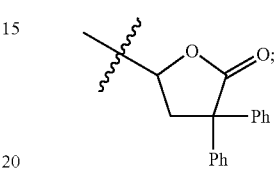

(viii) when n is 1, D is CHR$^9$ wherein R$^9$ is methyl, and C is 2-methoxyphenyl, phenyl, or 4-nitrophenyl, then ring A is not 4-benzenesulfonyl-phenyl, or 4-(4'-tolyl)-phenyl.

A is an optionally substituted monocyclic C3-C8 cycloaliphatic ring, such as an optionally substituted cyclopropyl, cyclopentyl, cyclohexyl, or cycloheptyl. A is an optionally substituted C7-C14 cycloaliphatic ring, such as a bicylic, bridged bicyclic or bridged tricyclic. In particular, A is an optionally substituted 1-adamantyl, 2-adamantyl, 1-norbornyl, or 1-bicyclo[2.2.1]hept-5-en-2-yl. A is an optionally substituted C6-C10 aryl ring. In particular, A is an optionally substituted phenyl or naphthyl. A is an optionally substituted C5-C12 heteroaryl ring. For instance, A is selected from an optionally substituted triazinyl, pyrazinyl, pyrimidinyl, pyridazinyl, pyridinyl, thiadiazolyl, triazolyl, oxadiazolyl, isothiazolyl, pyrazolyl, imidazolyl, thiazolyl, oxazolyl, pyrrolyl, thienyl, furanyl, indolizinyl, indolyl, isoindolyl, benzofuranyl, benzo[b]thienyl, 1H-indazolyl, benzimidazolyl, benzthiazolyl, purinyl, quinolinyl, isoquinolinyl, cinnolinyl, phthazinyl, quinazolinyl, quinoxalinyl, 1,8-naphthyridinyl, pteridinyl, acridinyl, phenazinyl, phenothiazinyl, or phenoxazinyl. A is an optionally substituted monocyclic, bicylic, bridged bicyclic or bridged tricyclic C3-C12 heterocyclic ring. A is selected from an optionally substituted aziridine, oxirane, thiirane, pyrrolidyl, tetrahydrofuranyl, tetrahydrothienyl, dioxolanyl, pyrrolinyl, pyranyl, pyrazolinyl, pyrazolidinyl, piperidinyl, 1,4-dioxanyl, morpholinyl, 1,4-dithianyl, thiomorpholinyl, piperazinyl, 3H-indolyl, or indolinyl.

In other embodiments of compounds of formulae I and IA, A is a monocyclic, bicylic, bridged bicyclic or bridged tricyclic C3-C12 heterocyclic ring, each optionally substituted with 1-5 substituents independently selected from R$^1$, R$^2$, R$^3$, R$^4$, or R$^5$. For instance, A is selected from optionally substituted oxirane, thiirane, pyrrolidyl, tetrahydrofuranyl, tetrahydrothienyl, dioxolanyl, pyrrolinyl, pyranyl, piperidinyl, 1,4-dioxanyl, morpholinyl, 1,4-dithianyl, thiomorpholinyl, or indolinyl. As described below in certain embodiments, ring A together with any substituents on ring A do not include any basic nitrogen atoms.

Two R$^1$ groups form 1,2-methylenedioxy, or 1,2-ethylenedioxy. Two R$^1$ groups form —CH═CH—CH═CH—, —CH═N—CH═CH—, —CH═CH—NH—. R$^1$ is R$^6$, wherein R$^6$ is straight chain or branched (C1-C6)alkyl or (C2-C6 alkenyl) or alkynyl, optionally substituted with R$^7$.

$R^1$ is $(CH_2)_m$—Y, wherein m is 0, 1, or 2, and Y is halo, CN, $NO_2$, $CF_3$, $OCF_3$, OH, $SR^6$, $S(O)R^6$, $SO_2R^6$, $NH_2$, $NHR^6$, $N(R^6)_2$, $NR^6R^8$, COOH, $COOR^6$ or $OR^6$. $R^1$ is selected from halo, $CF_3$, $NH_2$, NH(C1-C4 alkyl), $NHC(O)CH_3$, OH, O(C1-C4 alkyl), OPh, O-benzyl, S—(C1-C4 alkyl), C1-C4 aliphatic, $NO_2$, CN, methylenedioxy, ethylenedixoy, $SO_2NH$(C1-C4 alkyl), or $SO_2N$(C1-C4 alkyl)$_2$. $R^1$ is selected from methyl, n-propyl, i-propyl, t-butyl, halo, $CF_3$, $NH_2$, $NH(CH_3)$, $NHC(O)CH_3$, OH, $OCH_3$, OPh, O-benzyl, S—($C_2H_5$), S—$CH_3$, $NO_2$, CN, methylenedioxy, $SO_2NH$(n-propyl), or $SO_2N$(n-propyl)$_2$.

$R^2$ is a straight chain or branched (C1-C6)alkyl or (C2-C6) alkenyl or alkynyl, optionally substituted with $R^1$, $R^4$, or $R^5$. $R^2$ is a straight chain or branched (C1-C4)alkyl or (C2-C4) alkenyl or alkynyl, optionally substituted with $R^1$, $R^4$, or $R^5$.

$R^3$ is an optionally substituted phenyl, napthyl, C5-C10 heteroaryl or C3-C7 heterocyclyl. $R^3$ is an optionally substituted phenyl, C5-C6 heteroaryl, or C3-C6 heterocyclyl.

$R^4$ is selected from $OR^5$, $OR^6$, $SR^5$, $SR^6$, $NR^5COR^5$, $NR^5COR^6$, $NR^6COR^5$, or $NR^6COR^6$.

$R^5$ is C5-C6 cycloalkyl, C6 or C10 aryl, C5-C10 heteroaryl or C3-C7 heterocyclyl, optionally substituted with up to 2 $R^1$. $R^5$ is an optionally substituted cyclohexyl, phenyl, C5-C6 heteroaryl, or C3-C6 heterocyclyl.

$R^6$ is H. $R^6$ is a straight chain or branched (C1-C6)alkyl or (C2-C6 alkenyl) or alkynyl, optionally substituted with $R^7$. $R^6$ is a straight chain or branched (C1-C6)alkyl or (C2-C6 alkenyl) or alkynyl.

$R^7$ is C5-C6 cycloalkyl, phenyl, naphthyl, C5-C10 heteroaryl or C3-C7 heterocyclyl, optionally substituted with straight chain or branched (C1-C6)alkyl or (C2-C6 alkenyl) or alkynyl. $R^7$ is C5-C6 cycloalkyl, phenyl, naphthyl, C5-C10 heteroaryl or C3-C7 heterocyclyl, optionally substituted with 1-2-methylenedioxy, 1,2-ethylenedioxy, or $(CH_2)_n$-$Q^2$. In still other embodiments $R^7$ is an optionally substituted cyclohexyl, phenyl, C5-C6 heteroaryl, or C3-C6 heterocyclyl.

$R^8$ is acetyl, arylsulfonyl or alkylsulfonyl.

Ring A is selected from (a)-(n) as shown below:

(a)

(b)

(c)

(d)

-continued (e)
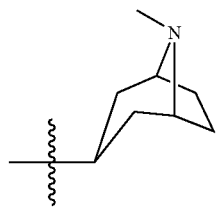

(f)
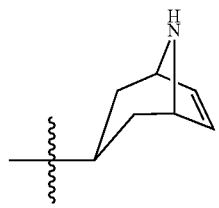

(g)
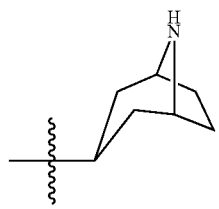

(h)
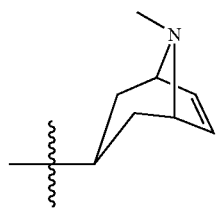

(i)
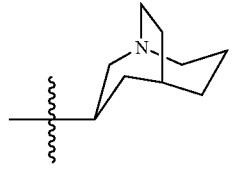

(j)
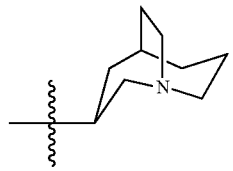

(k)
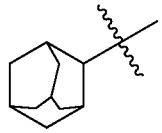

(l)
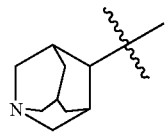

(m)
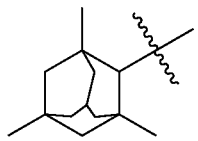
(n)
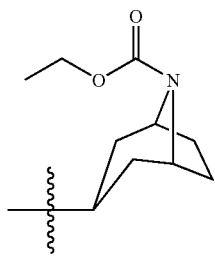
The invention also features compounds of formula I in which the piperazine ring may be replaced by any one of the following (i)-(xiv).
(i)
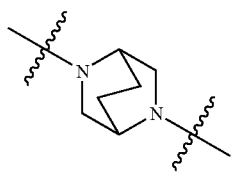
(ii)
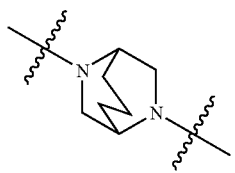
(iii)
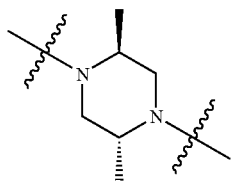
(iv)
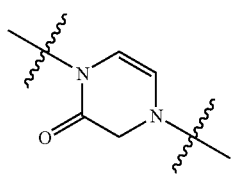
(v)
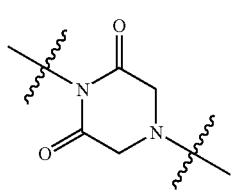
(vi)
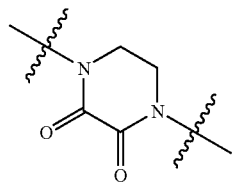
(vii)
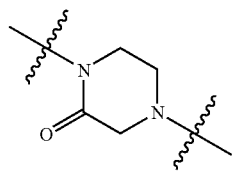
(viii)
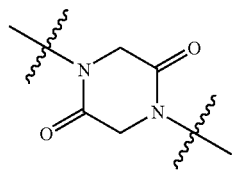
(ix)
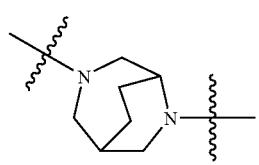
(x)
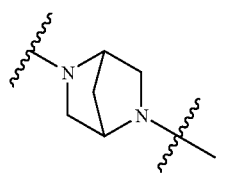
(xi)
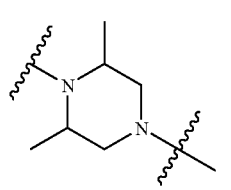
(xii)
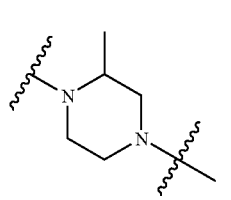
(xiii)
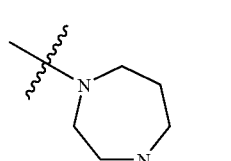
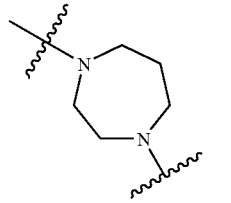

-continued (xiv)

According to another aspect, the present invention provides a compound having formula (II):

(II)

wherein:
ring $A_{II}$ is selected from:

X, Y, and $Z_5$ are each independently CR' or N;

$X_1$ and $Y_1$ are independently selected from a bond, $CH_2$, $CHR^9$, O, S, NH, NR', C(O), S(O), or $SO_2$ provided that both $X_1$ and $Y_1$ are not simultaneously a bond;

Z is $C(R')_2$, $C(R')_2$—$C(R')_2$, $C(R')_2$-Q, or Q, wherein Q is O, NR', S(O), $SO_2$, or C(O);

Each of $Z_1$, $Z_2$, $Z_3$, and $Z_4$ is independently selected from $CH_2$, CHR', O, S, NH, NR', C(O), S(O), $SO_2$;

Each R' is independently selected from (C1-C4)aliphatic)$_m$-$Q^1$, $S(O)_iR^6$, $S(O)_iR^5$, $SO_2N(R^6)_2$, $SO_2N(R^5)_2$, $SO_2NR^5R^6$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $R^2$, or $R_6$, provided that when any of $X_1$, $Y_1$, Z, $Z_1$, $Z_2$, $Z_3$, and $Z_4$ are NR', then R' is $S(O)_iR^6$, $S(O)_iR^5$, $SO_2N(R^6)_2$, $SO_2N(R^5)_2$, $SO_2NR^5R^6$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$;

Each of B, D, $Q^1$, $R^1$, $R^2$, $R^3$, $R^4$, $R^5$, $R^6$, $R^7$, $R^8$, $R^9$, and n are defined above as in formula I; and further provided one or more of the following:
(i) when C is dimethyl-fluoro-phenyl, n is 1, D is $CH_2$, Z is $C(CH_3)_2$, X and Y are both CH, and B is piperazine, then $X_1$ and $Y_1$ are not both $CH_2$; and (ii) when C is 2-methylphenyl, n is 1, D is C(O), Z is $C(alkyl)_2$, $X_1$ and $Y_1$ both are simultaneously CH or $CH_2$, and B is piperazine, then X and Y are not simultaneously CH;
(iii) when C is phenyl substituted with R2, D is C(O) or $CH_2$, n is 1, and B is piperazine, then ring $A_{II}$ is not adamantanyl; and
(iv) the compound is not 1-phenyl-4-4(tricycle[3.3.1.13,7]dec-1ylmethyl-piperazine.

Embodiments of the compounds of formula II include one or more of the following.

The radical R' in the compounds of formula (II) is (C1-C4) aliphatic)$_m$-$Q^1$. The radical R' is $R^2$. The radical R' is $R^6$.

The ring $A_{II}$ in formula (II) has the structure wherein X, Y, Z, $X_1$ and $Y_1$ are as described above. X and Y are CH. One of X and Y is CH and the other of X and Y is N. $X_1$ and $Y_1$ are both $CH_2$. $X_1$ and $Y_1$ are both NR. One of $X_1$ and $Y_1$ is $CH_2$ and the other of $X_1$ and $Y_1$ is NR, such as NH. Z is O, $CH_2$ or NR, such as NH. Z is C(O), —$CH_2$—C(O)—, or —C(O)—$CH_2$—.

The ring $A_1$ in formula (II) has the structure wherein $Z_1$, $Z_2$, and $Z_5$ are as described above. Each of $Z_1$ and $Z_2$ is $CH_2$, CHR, NH, or C(O). Each of $Z_1$ and $Z_2$ is $CH_2$ or NH. $Z_5$ is CH. $Z_5$ is N.

The ring $A_1$ in formula (II) has the structure wherein $Z_1$, $Z_3$, X and Y are as defined above. $Z_1$ and $Z_3$ are each independently $CH_2$ or NH. $Z_1$ and $Z_3$ are each $CH_2$. Preferably, each of X and Y is CH. Or, each of X and Y is N. Or, one of two X is N. Or, one of two Y is N.

In other embodiments of compounds of formula II, the variables X, Y, and $Z_5$ are each independently CR'; $X_1$ and $Y_1$ are independently selected from a bond, $CH_2$, $CHR^9$, O, S, NR', C(O), S(O), $SO_2$, or together form —CH=CH—, provided that both $X_1$ and $Y_1$ are not simultaneously a bond; Z is $C(R')_2$, $C(R')_2$—$C(R')_2$, $C(R')_2$-Q, or Q, wherein Q is O, NR', S(O), $SO_2$, or C(O); Each of $Z_1$, $Z_2$, $Z_3$, and $Z_4$ is independently selected from CH$_2$, CHR', O, S, NR', C(O), S(O), SO$_2$; and R' is selected from (C1-C4)aliphatic)$_m$-Q$^1$, R$^2$, or R$_6$, provided that when any of X$_1$, Y$_1$, Z, Z$_1$, Z$_2$, Z$_3$, and Z$_4$ are NR', then R' is not hydrogen.

According to another aspect, the present invention provides a compound having formula (III):

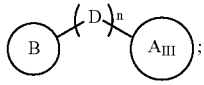
(III)

wherein:

ring A$_{III}$ is

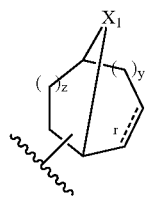

optionally substituted with 1-3 of R';

X$_1$ is independently selected from a bond, CH$_2$, CHR$^9$, O, S, NH, NR', C(O), S(O), SO$_2$;

Each R' is independently selected from (C1-C4)aliphatic)$_m$-Q$^1$, S(O)$_i$R$^6$, S(O)$_i$R$^5$, SO$_2$N(R$^6$)$_2$, SO$_2$N(R$^5$)$_2$, SO$_2$NR$^5$R$^6$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^6$, C(O)N(OR$^6$)R$^5$, C(O)N(OR$^5$)R$^5$, C(NOR$^6$)R$^6$, C(NOR$^6$)R$^5$, C(NOR$^5$)R$^6$, C(NOR$^5$)R$^5$, R$^2$ or R$_6$, provided that when any of X$_1$, Y$_1$, Z, Z$_1$, Z$_2$, Z$_3$, and Z$_4$ are NR', then R' is S(O)$_i$R$^6$, S(O)$_i$R$^5$, SO$_2$N(R$^6$)$_2$, SO$_2$N(R$^5$)$_2$, SO$_2$NR$^5$R$^6$, C(O)R$^5$, C(O)OR$^5$, C(O)R$^6$, C(O)OR$^6$, C(O)N(R$^6$)$_2$, C(O)N(R$^5$)$_2$, C(O)N(R$^5$R$^6$), C(O)N(OR$^6$)R$^6$, C(O)N(OR$^5$)R$^6$, C(O)N(OR$^6$)R$^5$, C(O)N(OR$^5$)R$^5$, C(NOR$^6$)R$^6$, C(NOR$^6$)R$^5$, C(NOR$^5$)R$^6$, C(NOR$^5$)R$^5$;

Each y is 0, 1 or 2;

Each z is 0, 1, or 2, provided that y+z is 1, 2, or 3;

Bond r is a single or double bond; and

Each of B, D, Q1, R1, R2, R3, R4, R5, R6, R7, R8, R9, and n are defined above as in formula I;

provided that when D is CH$_2$, y is 1 and z is 2, that X1 is other than C(O) or —CH(OH)—.

Embodiments of this aspect include one or more of the following. X$_1$ is NR'. X$_1$ is —N(C(O)OR$_5$)—. X$_1$ is independently selected from a bond, CH$_2$, CHR$^9$, O, S, NR', C(O), S(O), SO$_2$; and R' is selected from (C1-C4)aliphatic)$_m$-Q$^1$, R$^2$, or R$_6$, provided that R$_6$ is not hydrogen.

In some embodiments, the compounds of formulae I, IA, II, and III include only a single basic nitrogen atom in any of B, D, or A and any of the substituents attached to B, D, and A, wherein a basic nitrogen atom is defined as any nitrogen whose conjugate acid pka is greater than 7.1. For instance, the nitrogen atom at the 4 position relative to C is a basic nitrogen atom. In other embodiments, A and substituents attached to A do not include any basic nitrogen atoms, but B and D along with substituents attached to B and D may include one or more basic nitrogen atoms. Alternatively, ring A does not include any basic nitrogen atoms that form ring A, such as the nitrogen in piperidine, but B, D, and substituents attached to B,D, and A may include one or more basic nitrogen atoms.

In still other aspects, the invention features compounds of formulae I, IA, II, and III that include combinations of the different aspects and embodiments described above. For instance, embodiments of compounds of formula III may include one or more of the embodiments described above for compounds of formula I.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds that differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention. Such compounds are useful, for example, as analytical tools or probes in biological assays.

The compounds of formulae (I, IA, II, and III) may be readily synthesized using methods known in the art. An exemplary synthetic route to produce compounds of formula (I, IA II, and III), when ring B is piperazine, is provided below in Scheme 1.

Scheme 1:

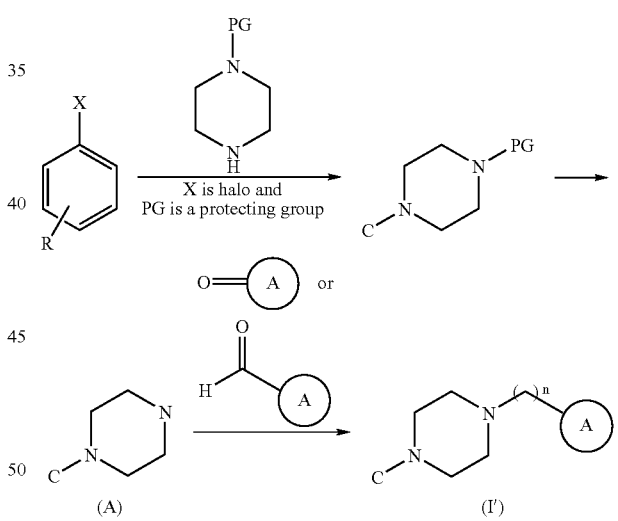

Referring to Scheme 1, the reaction of a ketone or aldehyde with an amine of formula (A) in the presence of a suitable reducing agent, e.g., sodium triacetoxyborohydride, produces compounds of formula I'. One of skill in the art will recognize that the above synthetic route depicted above are generic and can be readily adapted for other embodiments of compound formula (I) using methods known to those skilled in the art.

Compounds of formula (A) may be purchased commercially or synthesized from an optionally protected piperazine and aryl halide using methods known to those skilled in the art. Additionally, compounds of formulae I, IA, II, and III in which the piperazine ring is replaced by

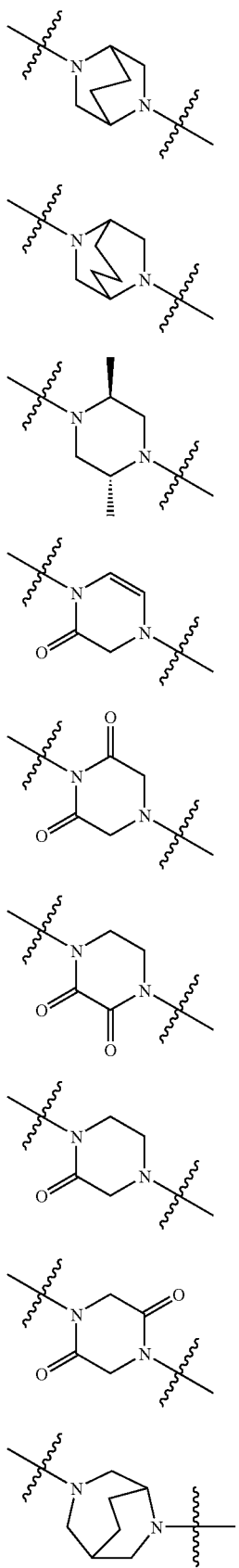

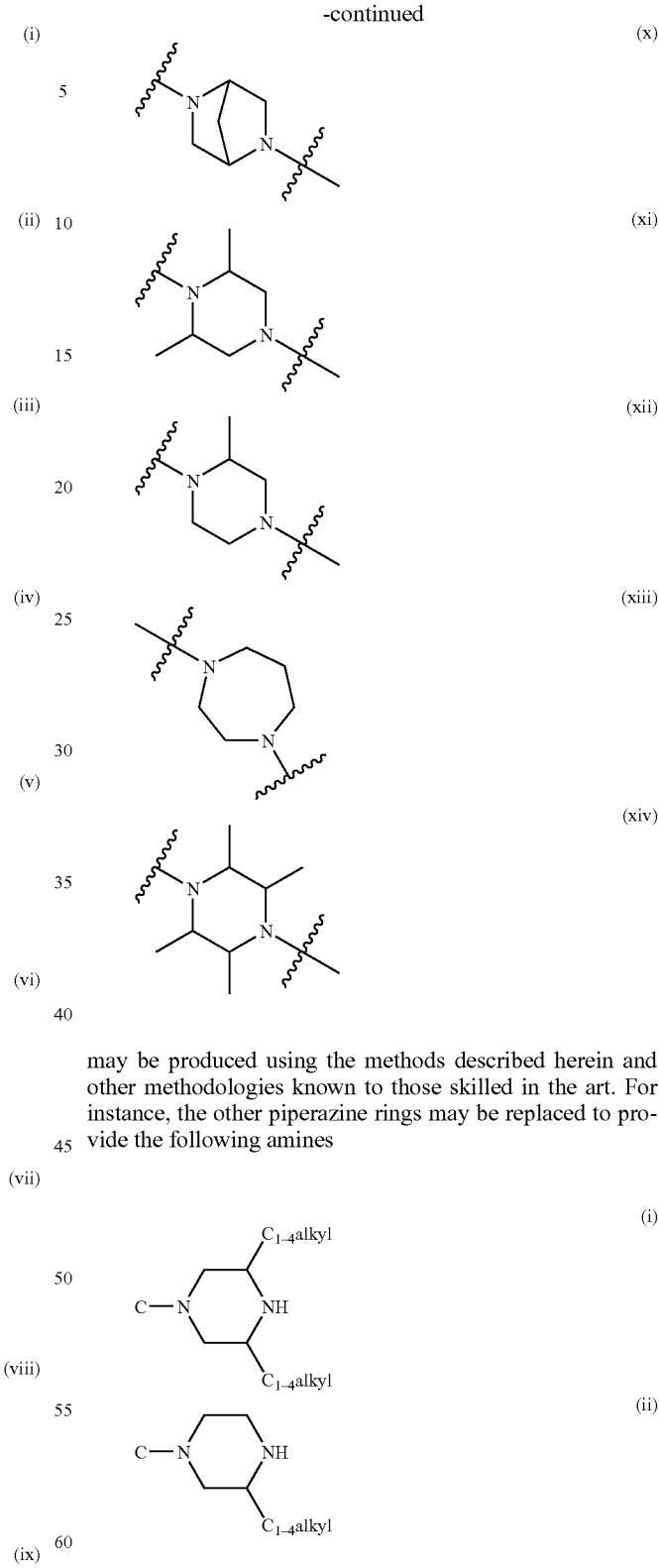

may be produced using the methods described herein and other methodologies known to those skilled in the art. For instance, the other piperazine rings may be replaced to provide the following amines The present invention includes within its scope pharmaceutically acceptable prodrugs of the compounds of the present invention. A "pharmaceutically acceptable prodrug" means any pharmaceutically acceptable salt, ester, salt of an ester, or other derivative of a compound of the present invention which, upon administration to a recipient, is capable of providing (directly or indirectly) a compound of this invention or an active metabolite or residue thereof. Preferred prodrugs are those that increase the bioavailability of the compounds of this invention when such compounds are administered to a mammal or which enhance delivery of the parent compound to a biological compartment relative to the parent species.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., calcium or magnesium), ammonium and $N^+(C_{1-4} alkyl)_4$ salts or salts of lysine and arginine. This invention also envisions the quaternization of any basic nitrogen-containing groups of the compounds disclosed herein. Water or oil-soluble or dispersible products may be obtained by such quaternization. Other salts can be found in "Practical Process, Research, & Development," Anderson, Neal G., Academic Press, 2000, the contents of which are incorporated herein by reference.

The compositions of the present invention may be administered orally, parenterally, by inhalation spray, topically, rectally, intermuscularly, subcutaneously, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the modulator can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated."

According to a preferred embodiment, the compounds of formulae (I, IA, II, and III) are selective modulators of $M_1$, $M_2$ and $M_4$. More preferably, the compounds of formula (I, IA, II, and III) are selective modulators of $M_1$ and $M_4$. Or, the compounds of formula (I, IA, II, and III) are selective modulators of $M_2$ and $M_4$. Yet more preferably, the compounds of formula (I, IA, II, and III) are selective modulators of one of $M_1$, $M_2$, and $M_4$. The compounds of formula (I, IA, II, and III) are selective modulators of $M_4$. The compounds of formula (I, IA, II, and III) are selective modulators of $M_1$.

Applicants believe that the ability of the compounds of the present invention to modulate the activity of muscarinic receptors is derived from the affinity of these compounds to the muscarinic receptors. Such affinity, applicants believe, activates a muscarinic receptor (i.e, an agonist) or inhibits the activity of a muscarinic receptor.

According to another embodiment, the compounds of formula (I, IA, II, and III) are selective activators of all of $M_1$, $M_2$, and $M_4$. In other embodiments, the compounds of formula (I, IA, II, and III) are selective activators of one of $M_1$, $M_2$, and $M_4$ and selective inhibitors of the other two of $M_1$, $M_2$, and $M_4$. In another embodiment, the compounds of formula (I, IA, II, and III) are selective activators of up to two of $M_1$, $M_2$, and $M_4$ and selective inhibitors of the other of $M_1$, $M_2$, and $M_4$. In still another embodiment, the compounds of formula (I, IA, II, and III) are selective inhibitors of all of $M_1$, $M_2$, and $M_4$.

According to another embodiment, the compounds of compounds of formula (I, IA, II, and III) are selective inhibitors of one or more of $M_1$, $M_2$, or $M_4$. In one embodiment, preferably, the compounds of formula (I, IA, II, and III) are selective inhibitors of $M_4$. In another embodiment, the compounds of formulae (I, IA, II, and III) are selective inhibitors of $M_1$. In yet another embodiment, the compounds of formulae (I, IA, II, and III) are selective inhibitors of $M_1$ and $M_4$. In still another embodiment, the compounds of formulae (I, IA, II, and III) are selective inhibitors of $M_1$ and $M_2$ or $M_4$ and $M_2$.

The term "selective" as used herein means a measurably greater ability to modulate one muscarinic receptor subtype when compared to the other muscarinic receptor subtypes. E.g., the term "selective $M_4$ agonist" means a compound that has a measurably greater ability to act as an $M_4$ agonist when compared to that compound's agonist activity with the other muscarinic receptor subtype(s).

According to an alternative embodiment, the present invention provides a method of treating a muscarinic receptor mediated disease in a mammal, comprising the step of administering to said mammal a composition comprising a compound of formulae (I, IA, II, and III), or a preferred embodiment thereof as set forth above.

According to a preferred embodiment, the present invention provides a method of treating a disease mediated by one or more of $M_1$, $M_2$, or $M_4$, comprising the step of administering to said mammal a composition comprising a compound of formula (I, IA, II, and III), or a preferred embodiment thereof as set forth above. Or in another embodiment the disease is mediated by $M_2$. Or, said disease is mediated by $M_1$. Yet more preferably, said disease is mediated by $M_4$. In still further embodiments, the disease is mediate by all of $M_1$, $M_2$, and $M_4$. In another embodiment, the disease is mediate by two of $M_1$, $M_2$, and $M_4$.

According to a preferred embodiment, the present invention provides a method of treating or reducing the severity of a disease in a patient, wherein said disease is selected from CNS derived pathologies including cognitive disorders, Attention Deficit Hyperactivity Disorder (ADHD), obesity, Alzheimer's disease, various dementias such as vascular dementia, psychosis associated with CNS disorders including schizophrenia, mania, bipolar disorders, pain conditions including acute and chronic syndromes, Huntington's Chorea, Friederich's ataxia, Gilles de la Tourette's Syndrome, Downs Syndrome, Pick disease, clinical depression, Parkinson's disease, peripheral disorders such as reduction of intra ocular pressure in Glaucoma and treatment of dry eyes and dry mouth including Sjögren's Syndrome, and wound healing, wherein said method comprises the step of contacting said patient with a compound according to the present invention.

In one embodiment, the present invention provides a method for the treatment or lessening the severity of acute, chronic, neuropathic, or inflammatory pain, arthritis, migrane, cluster headaches, trigeminal neuralgia, herpetic neuralgia, general neuralgias, epilepsy or epilepsy conditions, neurodegenerative disorders, psychiatric disorders such as anxiety and depression, myotonia, arrythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, post-surgical pain, back pain, or cancer pain is provided comprising administering an effective amount of a compound or a pharmaceutically acceptable composition to a subject in need thereof.

According to an alternative embodiment, the present invention provides a method of treating or reducing the severity of a disease in a patient, wherein said disease is selected from pain, psychosis (including schizophrenia, hallucinations, and delusions), Alzheimer's disease, Parkinson's disease, glaucoma, bradhycardia, gastric acid secretion, asthma, GI disturbances or wound healing.

According to a preferred embodiment, the present invention is useful for treating or reducing the severity of psychosis, Alzheimer's disease, pain, or Parkinson's disease.

In order that the invention described herein may be more fully understood, the following examples are set forth. It should be understood that these examples are for illustrative purposes only and are not to be construed as limiting this invention in any manner.

All references cited above are incorporated herein by reference.

Other embodiments of the compounds of formulae (I, IA, II, and III) are shown below. The following examples are illustrative of the compounds of formula (I, IA, II, and III) and are not meant to be limiting.

EXAMPLES

Example 1

Synthesis of 1-Bicyclo[2.2.1]hept-5-en-2-ylmethyl-4-(2-chloro-phenyl)-piperazine.

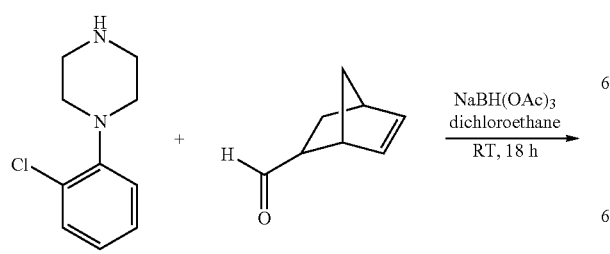

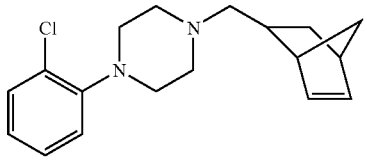

1-(2-Chloro-phenyl)-piperazine (4.0 g, 20.34 mmol) was dissolved in 80 mL anhydrous 1,2-dichloroethane (DCE) in a 250 mL flask, followed by the addition of 2.48 g (20.34 mmol) of 5-norbornene-2-carboxaldehyde and 6.05 g (28.47 mmol, 1.4 eq) of sodium triacetoxyborohydride [NaBH(OAc)3]. The flask was flushed with nitrogen and allowed to stir for 18 h. The reaction was diluted with 0.1 N NaOH and the product extracted into dichloromethane (3×100 mL). The dichloromethane was washed with 10% saturated sodium bicarbonate, brine, dried over $Na_2SO_4$, and concentrated to form a colorless oil. The residue was brought up in 30 mL anhydrous diethyl ether and the product precipitated as the HCl salt with the addition of 10.2 mL HCl in ether (2.0 M solution in ether, 20.4 mmol). The white precipitate was filtered, washed with ether, and then recrystallized from ethyl acetate/methanol to yield the product as white crystals.

$^1$H NMR (400 mHz, DMSO-$d_6$) δ 10.34 (bs, 1H), 7.45 (dd, J=7.9 Hz, 1.4 Hz, 1H), 7.35 (dt, J=7.9 Hz, 1.4 Hz, 1H), 7.21 (dd, J=8.1 Hz, 1.4 Hz, 1H), 7.11 (dt, J=7.8 Hz, 1.4 Hz, 1H), 6.24 (m, 0.8H), 6.14 (m, 0.4H), 6.07 (m, 0.8H), 3.59 (m, 2H), 3.38 (m, 2H), 3.11-3.30 (m, 4.5H), 2.90-3.05 (m, 1.5H), 2.75-2.90 (m, 2H), 2.54 (m, 0.8H, obscured by DMSO), 2.00 (m, 0.8H), 1.80 (m, 0.2H), 1.2-1.37 (m, 2.5H), 0.71 (m, 0.8H);

LC/MS retention time (10-99% CH$_3$CN/0.085% TFA gradient over 5 min): 2.39 min; Theoretical (M+H)$^+$ m/z=303.2; Found 303.2.

Example 2

Synthesis of 1-Bicyclo[2.2.1]hept-2-yl-4-o-tolyl-piperazine

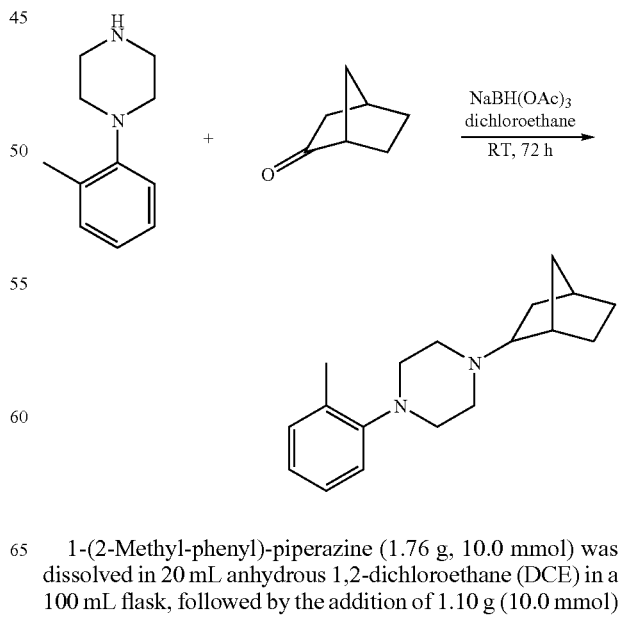

1-(2-Methyl-phenyl)-piperazine (1.76 g, 10.0 mmol) was dissolved in 20 mL anhydrous 1,2-dichloroethane (DCE) in a 100 mL flask, followed by the addition of 1.10 g (10.0 mmol)

of norcamphor, 1.15 mL glacial acetic acid (20 mmol), and 2.97 g (14.0 mmol) of sodium triacetoxyborohydride [NaBH(OAc)₃]. The flask was flushed with nitrogen and allowed to stir for 72 h at room temperature. The reaction was diluted with 20% saturated sodium bicarbonate and the product extracted into dichloromethane (3×100 mL). The dichloromethane was washed brine, dried over Na₂SO₄, and concentrated to form a colorless oil. The residue was brought up in 30 mL anhydrous diethyl ether and clarified with 1 mL anhydrous ethanol. The product was precipitated as the HCl salt with the addition of 4.9 mL HCl in ether (2.0 M solution in ether, 9.8 mmol). The white precipitate was filtered, washed with ether, and dried to yield the product as a white powder.

¹H NMR (400 mHz, DMSO-d₆) δ 10.50 (bs, 1H), 7.17-7.21 (m, 2H), 6.99-7.04 (m, 2H), 3.40-3.50 (m, 4H), 3.18-3.32 (m, 2H), 3.05-3.16 (m, 3H), 2.58 (m, 1H), 2.27 (m, 1H), 2.25 (m, 3H), 1.90-1.96 (m, 2H), 1.49-1.60 (m, 3H), 1.29-1.45 (m, 3H);

LC/MS retention time (10-99% CH₃CN/0.085% TFA gradient over 5 min): 2.10 min; Theoretical (M+H)⁺ m/z=271.4; Found 271.4.

Example 3

Synthesis of 1-(2-Chloro-phenyl)-4-(4-ethyl-cyclohexyl)-piperazine

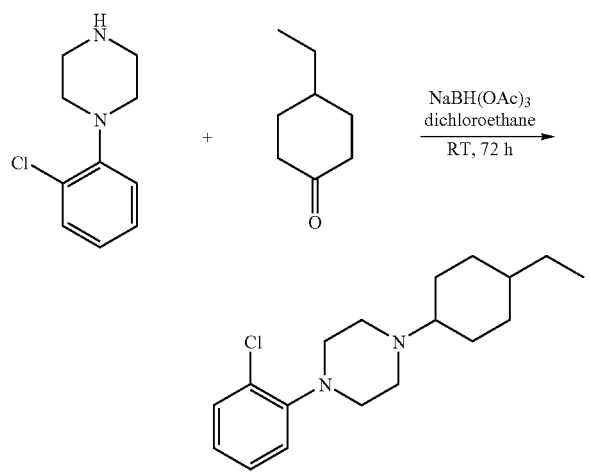

2-chlorophenylpiperazine (140 mg, 0.713 mmol) and 4-ethylcyclohexanone (100 mg, 0.792 mmol) were mixed in 1,2-dichloroethane (4 mL) and then treated with sodium triacetoxyborohydride (218 mg, 1.03 mmol) and glacial acetic acid (43 mg, 0.713 mmol). The mixture was stirred under N₂ at room temperature for 18 h. The reaction was quenched through the addition of 1.0 N NaOH (10 mL), and the product extracted in to methylene chloride (2×100 mL). The methylene chloride was washed with brine (25 mL), dried over Na₂SO₄, and filtered. The solvent was evaporated to give the crude free base as a colorless oil. The product was dissolved in anhydrous diethyl ether and treated with ethereal HCl (1 eq) to give the HCl salt. Recrystallization from ethyl acetate/methanol provided the product as white crystals.

¹H NMR (HCl salt, d₆-DMSO) δ 10.35 (bs, 1H), 7.46 (dd, 1H), 7.35 (dt, 1H), 7.21 (dd, 1H), 7.11 (dt, 1H), 3.60 (d, 2H), 3.43 (d, 2H), 3.11-3.24 (m, 5H), 1.35-2.0 (m, 11H), 0.86 (t, 3H);

LC/MS retention time (10-99% CH₃CN/0.05% TFA gradient over 5 min): 2.75 min. Theoretical (M+H)⁺ m/z=307.2; Found 307.2.

Example 4

Synthesis of 1-Bicyclo[2.2.1]hept-5-en-2-ylmethyl-4-(2-methoxy-5-methyl-phenyl)-piperazine

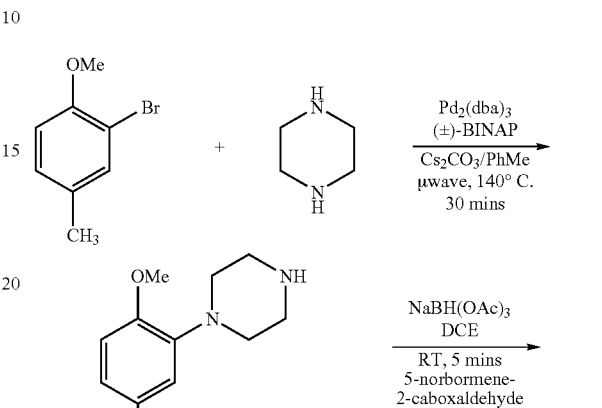

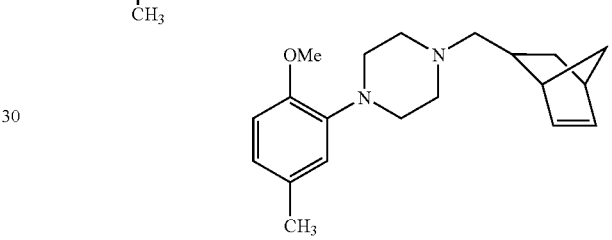

15 mg (0.016 mmol, 0.027 eq) Tris(dibenzylidene-acetone)dipalladium (0) (Pd₂dba₃), 27 mg (0.043 mmol, 0.072 eq) racemic-2,2'-Bis(diphenylphosphino)-1,1'-binaphthyl [(±)-BINAP] and 450 mg (1.38 mmol, 2.3 eq) cesium carbonate were combined in a microwave vial. 1.5 mL anhydrous toluene was added, followed by 121 mg (0.60 mmol, 1.0 eq) 2-bromo-4-methylanisole and 207 mg (2.40 mmol, 4.0 eq) piperazine. The vial was flushed with nitrogen prior to being microwaved at 140° C. for 30 minutes. The reaction mixture was diluted with 3.0 mL DMSO:methanol (1:1), filtered and purified by reverse-phase HPLC (2-99% CH₃CN in 0.085% TFA (aq), 50 mL/min, 3×1.5 mL injected). Yield=83 mg (43%) of 1-(2-Methoxy-5-methyl-phenyl)-piperazine as a pale yellow oil (isolated as the mono-TFA salt);

¹H-NMR (400 MHz, DMSO-d₆) δ 8.97 (br s, 2H), 6.85 (d, J=8.2 Hz, 1H), 6.80 (dd, J=8.2 Hz, 1.3 Hz, 1H), 6.74 (d, J=1.7 Hz, 1H), 3.75 (s, 3H), 3.23 (br m, 4H), 3.14 (br m, 4H), 2.22 (s, 3H); LC/MS retention time (10-99% CH₃CN/0.05% TFA gradient over 5 min): 1.58 min; Theoretical (M+H)⁺ m/z=207.1; Found 207.2.

32 mg (0.10 mmol, 1.0 eq) of 1-(2-Methoxy-5-methylphenyl)-piperazine (as the mono-TFA salt) was suspended in 1.0 mL anhydrous 1,2-dichloroethane (DCE) and treated with 1.0 eq (10 mg) triethylamine. 1.0 eq (12 mg) 5-norbornene-2-carboxaldehyde was added, followed by 1.4 eq (30 mg) sodium triacetoxyborohydride [NaBH(OAc)₃]. The reaction was stirred at room temperature for 5 minutes, then quenched with 1.0 mL DMSO:methanol (1:1). The reaction mixture was filtered and purified by reverse-phase HPLC (2-99% CH₃CN in 0.085% TFA (aq), 50 mL/min, 2.0 mL injected). Yield=30 mg (70%) (isolated as the mono-TFA salt);

$^1$H-NMR (400 MHz, DMSO-d$_6$) δ 9.73 (br s, 1H), 6.86 (d, J=8.2 Hz, 1H), 6.81 (dd, J=8.2 Hz, 1.2 Hz, 1H), 6.73 (d, J=1.7 Hz, 1H), 6.25 (m, 0.8H), 6.15 (m, 0.2H), 6.04 (m, 0.8H), 5.92 (m, 0.2H), 3.75 (s, 3H), 3.58 (m, 2H), 3.48 (m, 2H), 3.18 (br m, 2H), 2.95 (br m, 4H), 2.80 (m, 2H), 2.23 (s, 3H), 2.00 (m, 0.8H), 1.78 (m, 0.4H), 1.35 (m, 1.4H), 1.27 (m, 1.6H), 0.67 (m, 0.8H); LC/MS retention time (10-99% CH$_3$CN/0.05% TFA gradient over 5 min): 2.16 min; Theoretical (M+H)$^+$ m/z=313.2; Found 313.2.

Example 5

Synthesis of 1-Bicyclo[2.2.1]hept-5-en-2-ylmethyl-4-(5-chloro-2-methoxy-phenyl)-2-methyl-piperazine

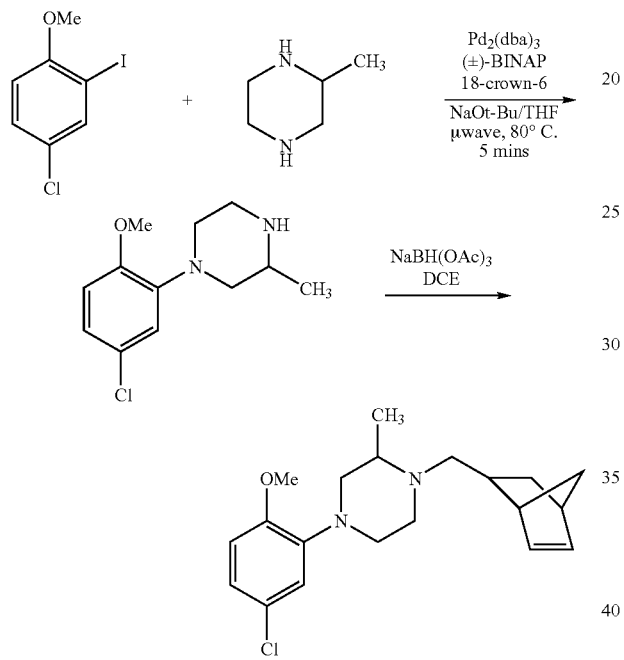

10 mg (0.010 eq) Pd$_2$dba$_3$.CHCl$_3$, 9.0 mg (0.015 eq) racemic BINAP, 135 mg (1.4 eq) NaOt-Bu, 370 mg (1.4 eq) 18-crown-6 ether and 1.0 mL anhydrous tetrahydrofuran were combined in a microwave vial. 268 mg (1.0 eq, 1.0 mmol) 4-Chloro-2-iodoanisole was added, followed by 120 mg (1.2 eq) racemic 2-methylpiperazine. The vial was flushed with nitrogen prior to being microwaved at 80° C. for 5 minutes. The reaction mixture was diluted with 1.0 mL DMSO:methanol (1:1) and centrifuged (4,000 rpm, RT, 8 min). The supernatant was filtered and purified by reverse-phase HPLC (2-99% CH$_3$CN in 0.085% TFA (aq), 50 mL/min, 2.0 mL injected). Yield=50 mg (14%) of a light brown oil (isolated as the mono-TFA salt);

$^1$H-NMR (400 MHz, DMSO-d$_6$) δ 9.14 (br d, J=8.6 Hz, 1H), 8.71 (br d, J=7.8 Hz, 1H), 7.10 (dd, J=8.7 Hz, 2.4 Hz, 1H), 6.99 (d, J=8.8 Hz, 1H), 6.94 (d, J=2.5 Hz, 1H), 3.80 (s, 3H), 3.42 (br m, 4H), 3.17 (m, 1H), 2.85 (m, 1H), 2.72 (m, 1H), 1.25 (d, J=6.4 Hz, 3H); LC/MS retention time (10-99% CH$_3$CN/0.05% TFA gradient over 5 min): 1.82 min; Theoretical (M+H)$^+$ m/z=241.1; Found 241.2.

48 mg (0.2 mmol) of 1-(5-Chloro-2-methoxy-phenyl)-3-methyl-piperazine was dissolved in 1.5 mL anhydrous 1,2-dichloroethane. 5-Norbornene-2-carboxaldehyde (25 mg, 0.2 mmol) was added, followed by followed by 63 mg (0.3 mmol) sodium triacetoxyborohydride [NaBH(OAc)$_3$]. The reaction was stirred overnight, then quenched with 1.0 mL DMSO:methanol (1:1). The reaction mixture was filtered and purified by reverse-phase HPLC (2-99% CH$_3$CN in 0.085% TFA (aq), 50 mL/min, 2.0 mL injected), and the product 1-bicyclo[2.2.1]hept-5-en-2-ylmethyl-4-(5-chloro-2-methoxy-phenyl)-2-methyl-piperazine isolated as the mono-TFA salt. Theoretical (M+H)$^+$ m/z=347.9; Found 348.0.

Example 6

Specific Compounds of Formulae I, IA, II, and III (I-1 through I-188) may be produced by methods described above using modifications know to those skilled in the art.

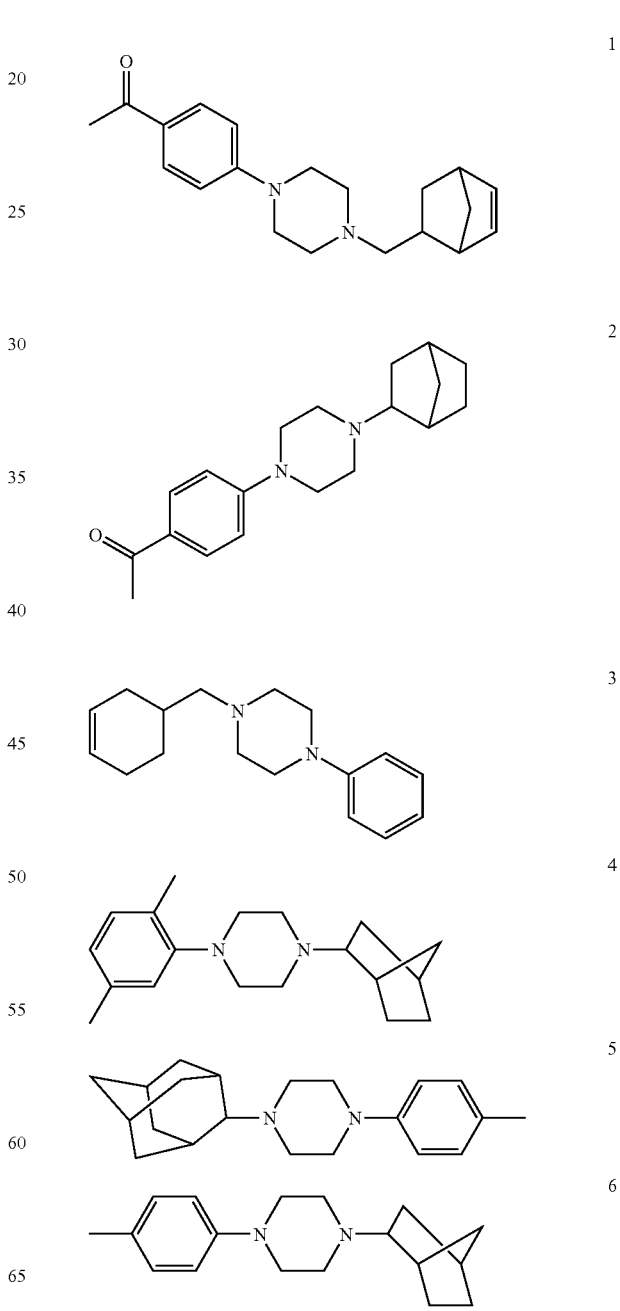

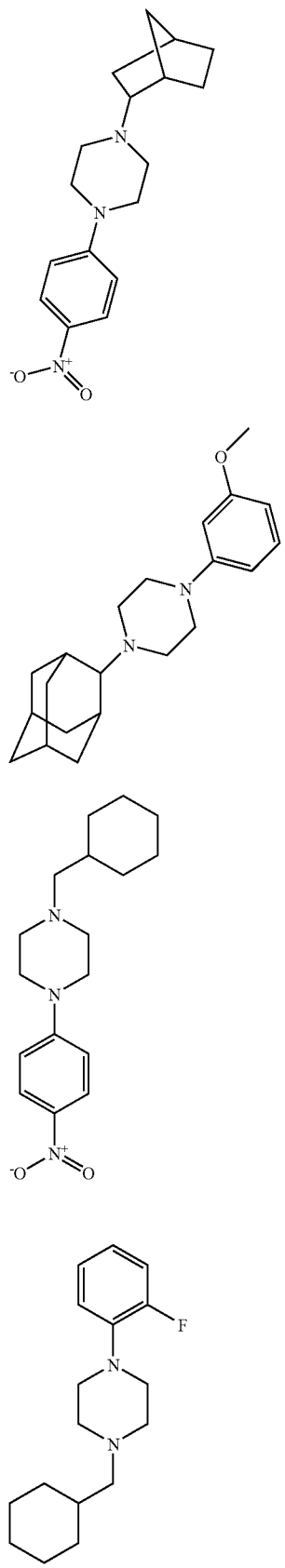
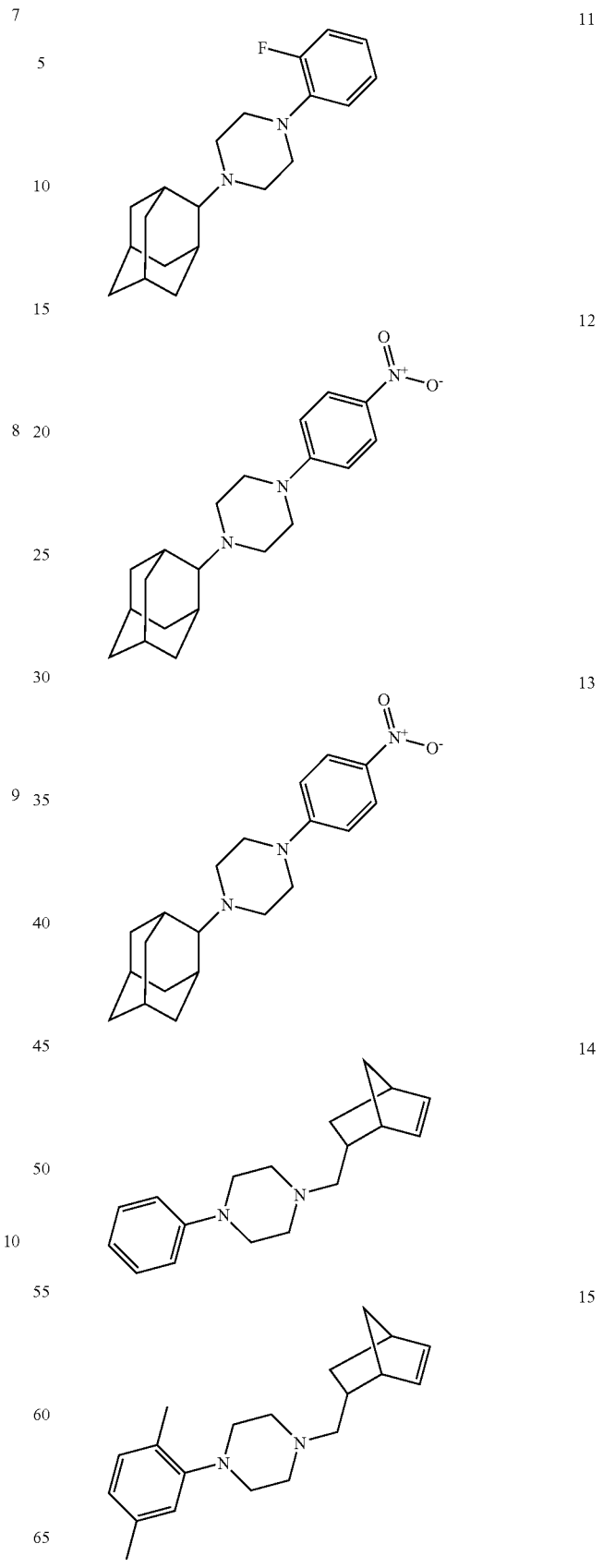

-continued
16 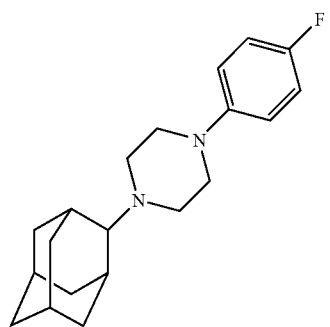
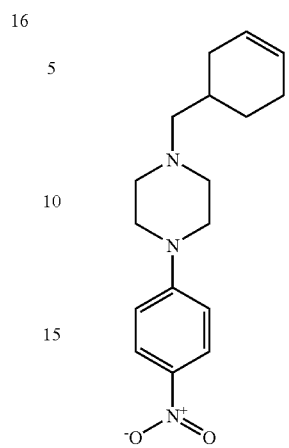
17 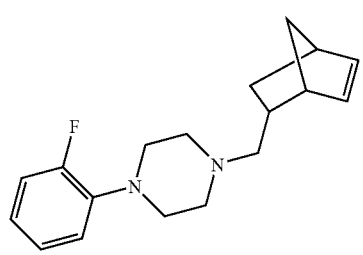
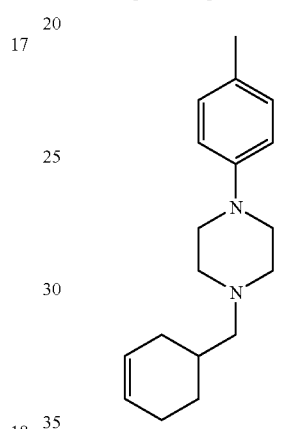
18 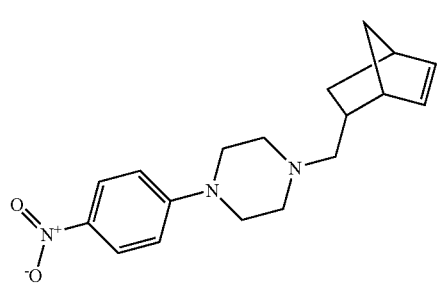
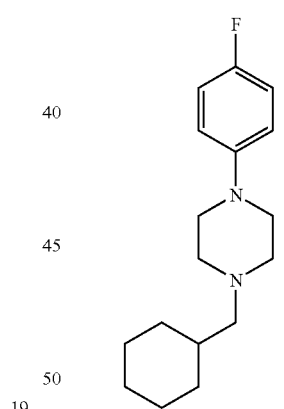
19 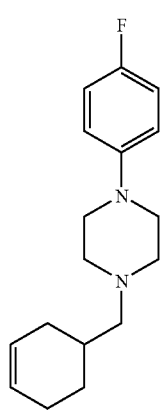
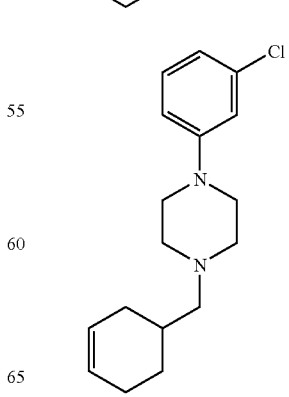

-continued
24
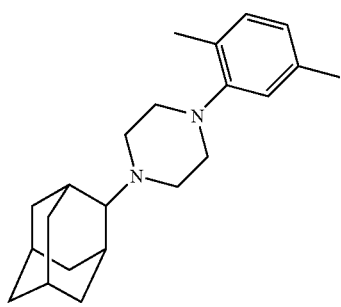
25
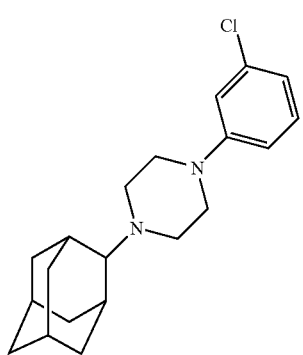
26
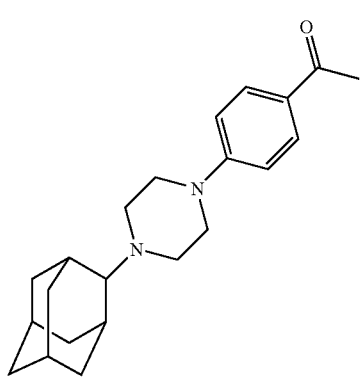
27
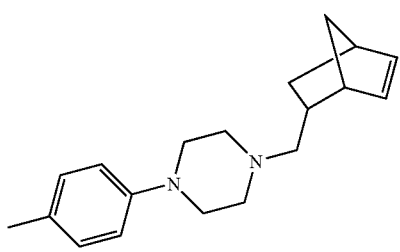
28
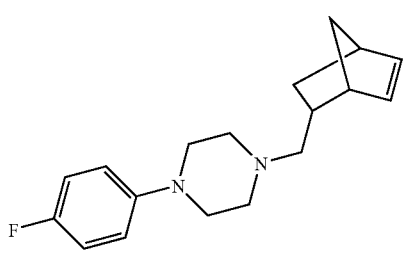
-continued
29
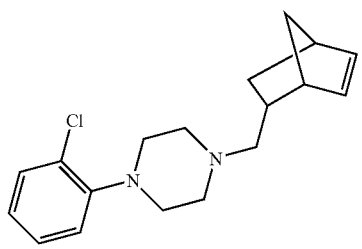
30
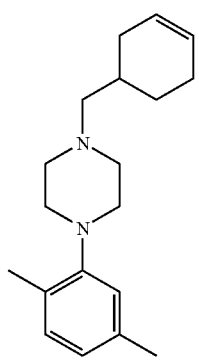
31
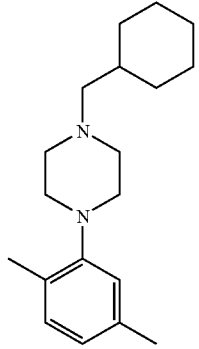
32
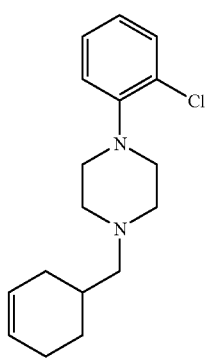

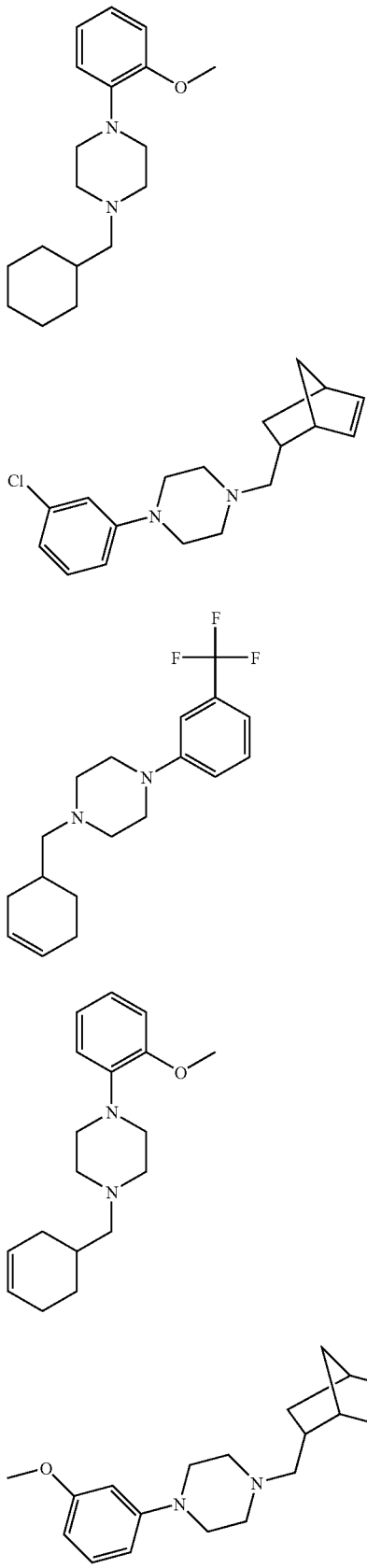

-continued
43
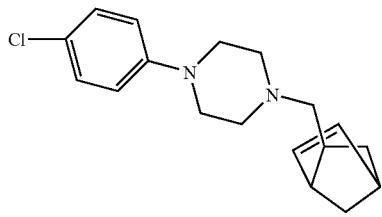
44
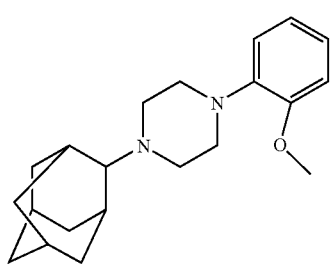
45
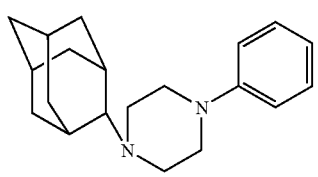
46
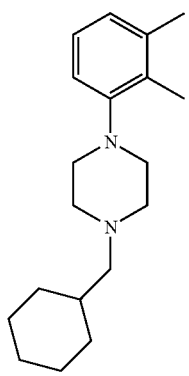
47
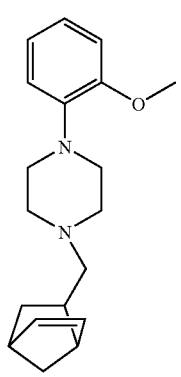
-continued
48
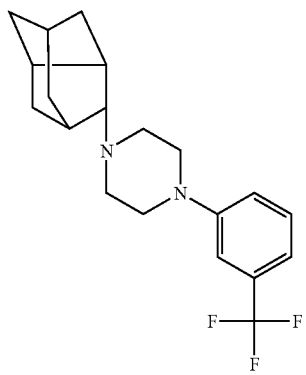
49
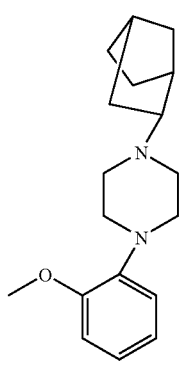
50
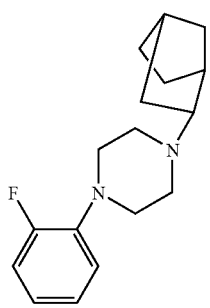
51
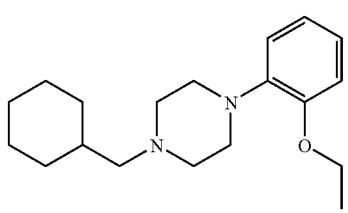

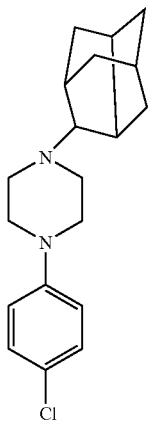
52
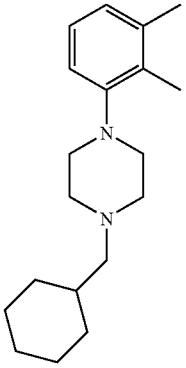
56
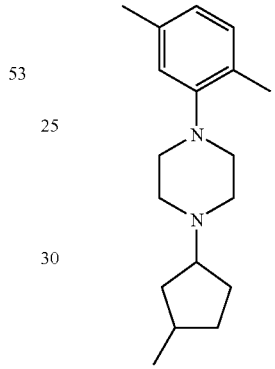
53
57
54
58
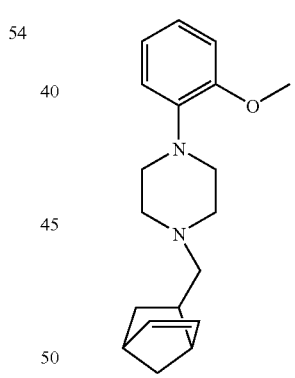
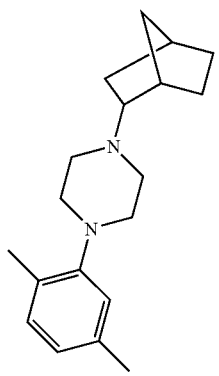
55
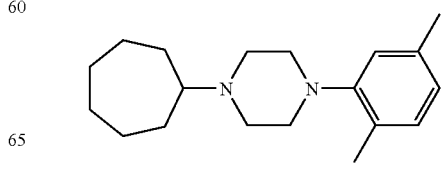
59
60

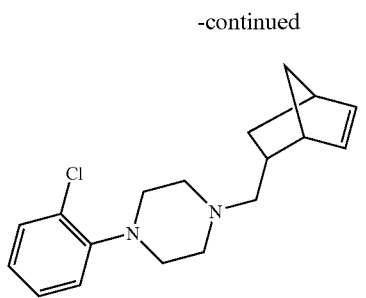
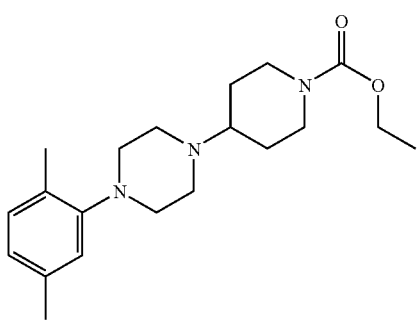
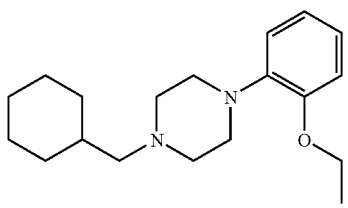
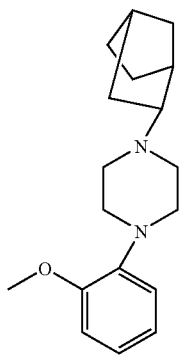
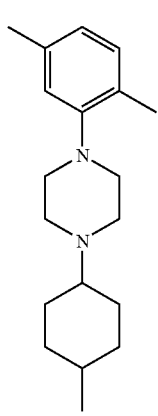
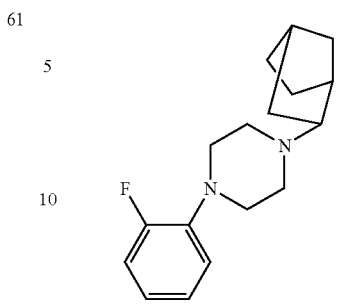
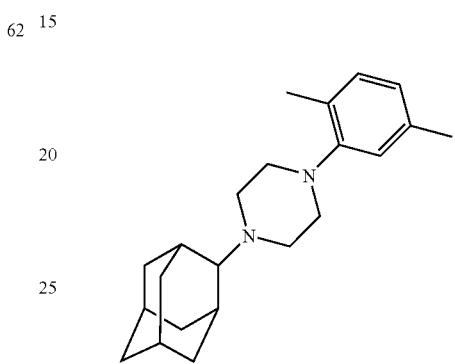
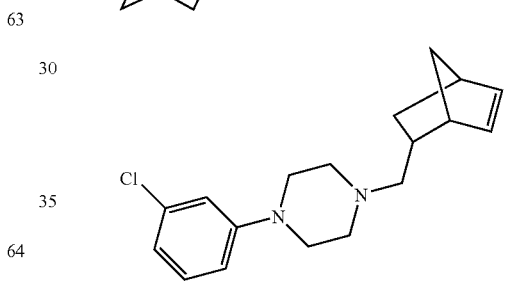
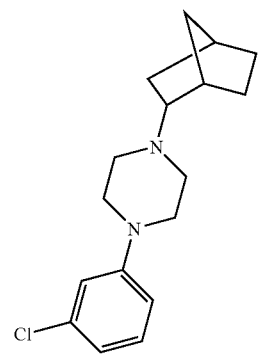
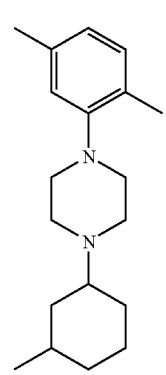

71
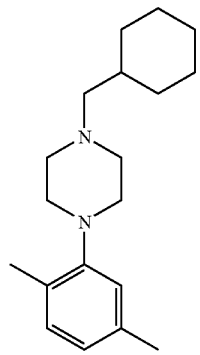
72
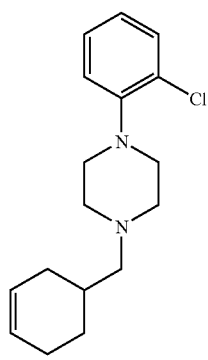
73
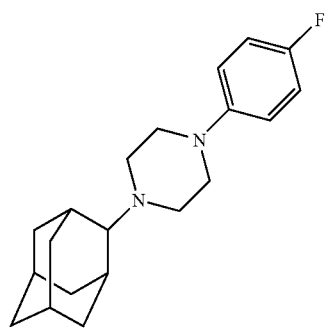
74
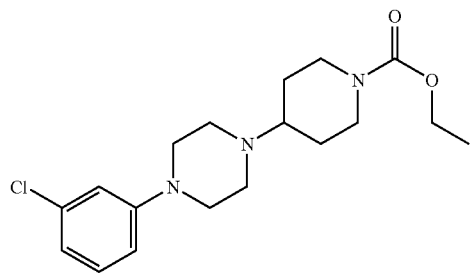
75
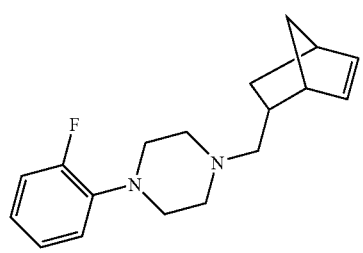
76
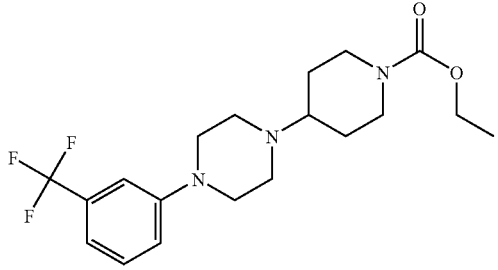
77
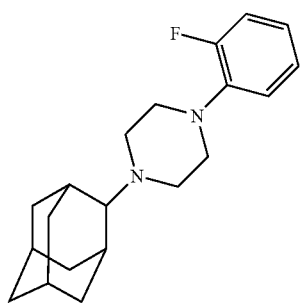
78
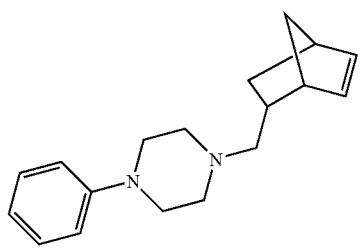
79
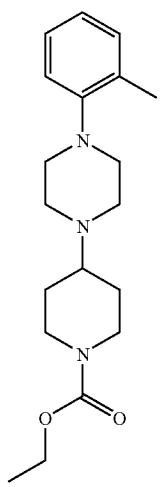

-continued
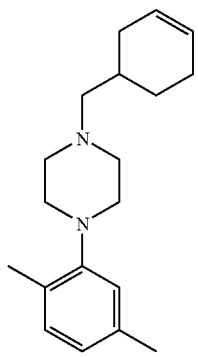
80
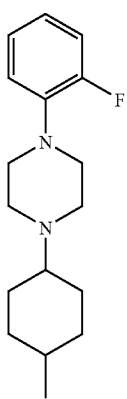
81
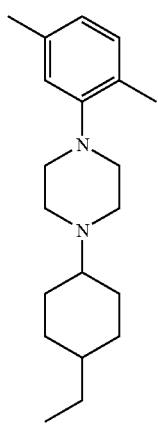
82
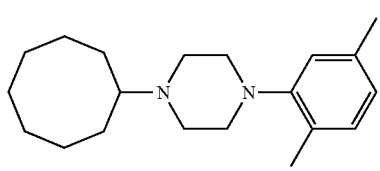
83
-continued
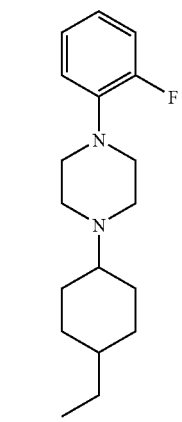
84
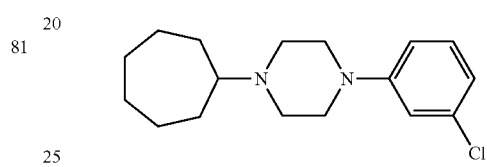
85
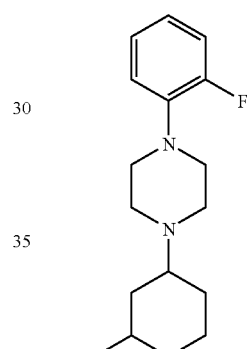
86
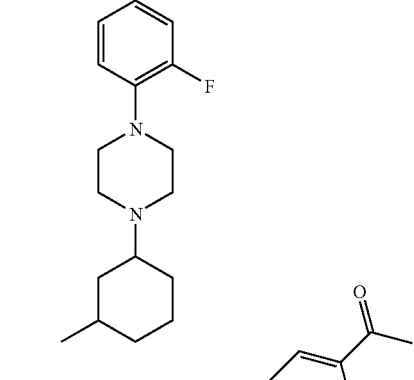
87
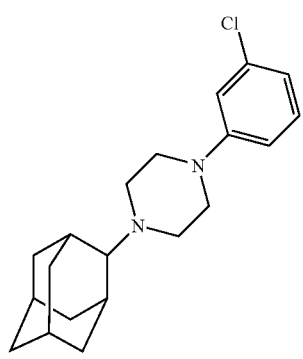
88

Example 7

Additional Compounds of formulae I, IA, II, and III (89-I-294) were produced by methods described above using modifications know to those skilled in the art.

| Compound | Cmpd # | LC/MS m/z | LC-RT (min) |
|---|---|---|---|
| | 89 | 321.30 | 2.27 |
| | 90 | 335.40 | 2.25 |
| | 91 | 321.10 | 2.28 |
| | 92 | 285.20 | 2.17 |

-continued

| Compound | Cmpd # | LC/MS m/z | LC-RT (min) |
|---|---|---|---|
| | 93 | 301.20 | 1.97 |
| | 94 | 317.20 | 2.24 |
| | 95 | 299.20 | 2.36 |
| | 96 | 317.00 | 2.09 |

-continued

| Compound | Cmpd # | LC/MS m/z | LC-RT (min) |
|---|---|---|---|
| | 97 | 335.40 | 2.22 |
| | 98 | 321.10 | 2.40 |
| | 99 | 333.30 | 2.55 |
| | 100 | 378.20 | 2.12 |
| | 101 | 299.20 | 2.42 |

-continued

| Compound | Cmpd # | LC/MS m/z | LC-RT (min) |
|---|---|---|---|
| | 102 | 335.40 | 0.56 |
| | 103 | 382.00 | 2.05 |
| | 104 | 283.10 | 2.57 |
| | 105 | 315.20 | 2.26 |

-continued

| Compound | Cmpd # | LC/MS m/z | LC-RT (min) |
|---|---|---|---|
| | 106 | 347.20 | 2.36 |
| | 107 | 305.20 | 2.30 |
| | 108 | 297.10 | 2.73 |
| | 109 | 319.20 | 2.15 |
| | 110 | 421.21 | 2.07 |

-continued
| Compound | Cmpd # | LC/MS m/z | LC-RT (min) |
|---|---|---|---|
| 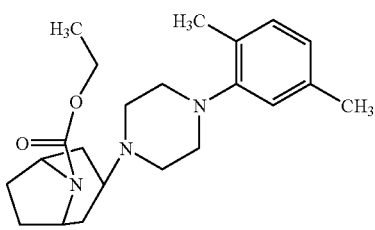 | 111 | 372.20 | 2.26 |
| 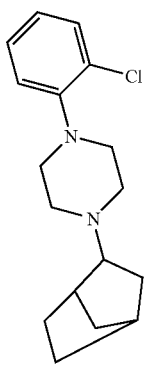 | 112 | 290.83 | 2.04 |
| 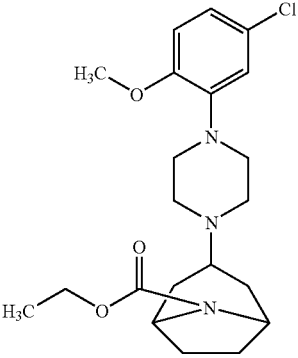 | 113 | 408.50 | 2.15 |
| 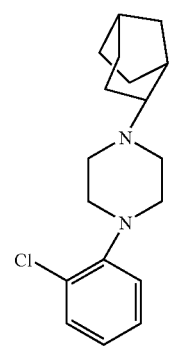 | 114 | 305.20 | 2.19 |

-continued
| Compound | Cmpd # | LC/MS m/z | LC-RT (min) |
|---|---|---|---|
| 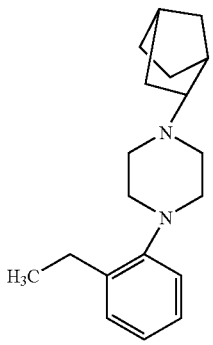 | 115 | 285.10 | 2.50 |
| 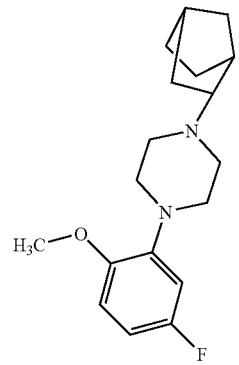 | 116 | 305.00 | 1.89 |
| 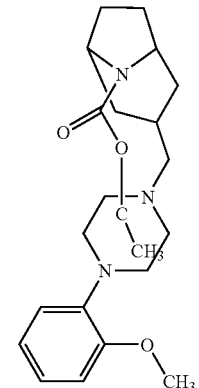 | 117 | 387.25 | 1.76 |
| 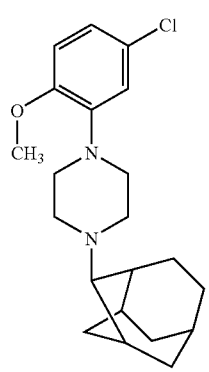 | 118 | 361.20 | 2.39 |

| Compound | Cmpd # | LC/MS m/z | LC-RT (min) |
|---|---|---|---|
| | 119 | 299.20 | 2.05 |
| | 120 | 323.50 | 3.12 |
| | 121 | 364.40 | 2.08 |
| | 122 | 303.20 | 2.12 |

-continued
| Compound | Cmpd # | LC/MS m/z | LC-RT (min) |
|---|---|---|---|
| 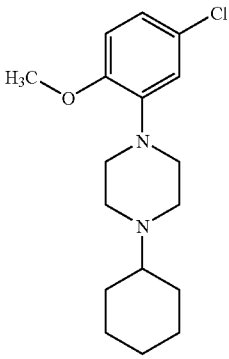 | 123 | 309.30 | 3.06 |
| 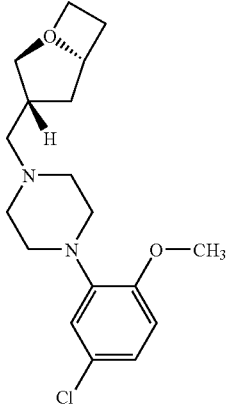 | 124 | 336.16 | 1.79 |
| 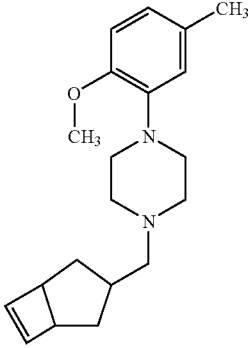 | 125 | 313.20 | 2.16 |
| 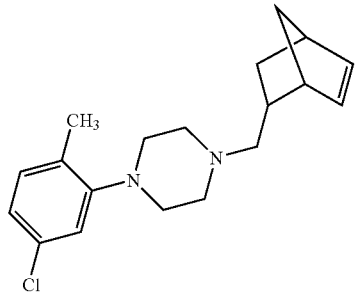 | 126 | 317.00 | 2.45 |

| Compound | Cmpd # | LC/MS m/z | LC-RT (min) |
|---|---|---|---|
| | 127 | 305.32 | 2.30 |
| | 128 | 358.20 | 2.35 |
| | 129 | 328.20 | 1.85 |
| | 130 | 344.20 | 2.15 |

-continued
| Compound | Cmpd # | LC/MS m/z | LC-RT (min) |
|---|---|---|---|
| 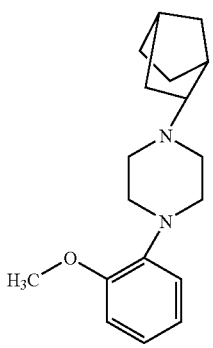 | 131 | 287.00 | 2.20 |
| 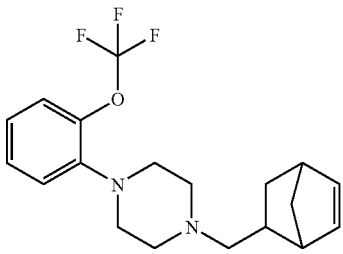 | 132 | 353.20 | 2.50 |
| 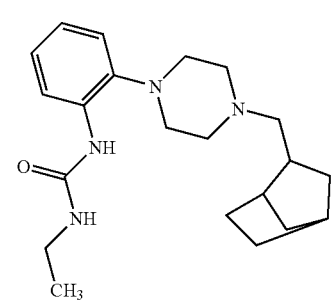 | 134 | 357.20 | 2.02 |
| 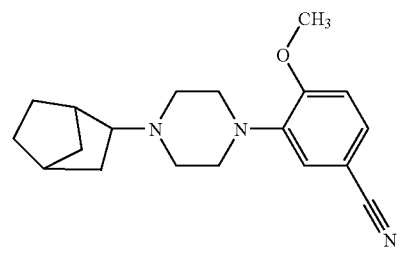 | 135 | 312.20 | 1.86 |
| 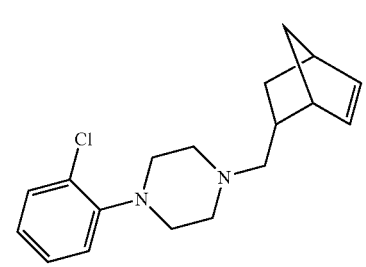 | 136 | 303.50 | 2.35 |

| Compound | Cmpd # | LC/MS m/z | LC-RT (min) |
|---|---|---|---|
| 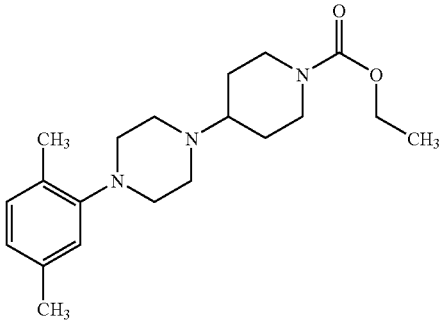 | 137 | | |
| 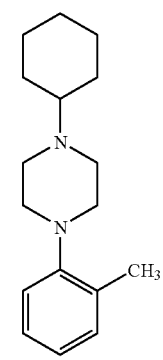 | 138 | 259.20 | 2.06 |
| 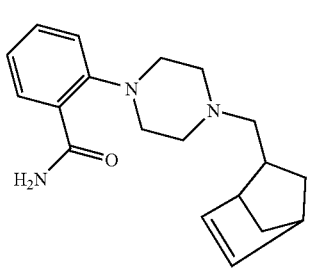 | 139 | 312.20 | 1.55 |
| 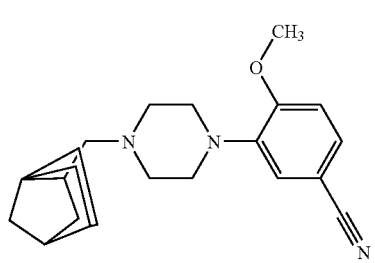 | 140 | 324.20 | 2.03 |
| 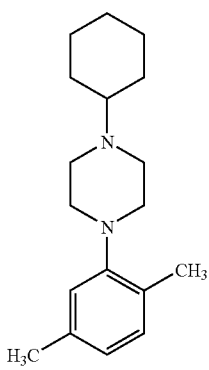 | 141 | 273.20 | 2.23 |

-continued
| Compound | Cmpd # | LC/MS m/z | LC-RT (min) |
|---|---|---|---|
| 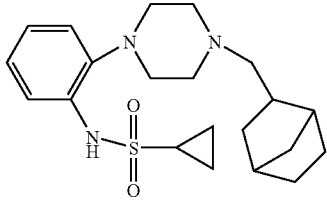 | 142 | 390.40 | 2.30 |
| 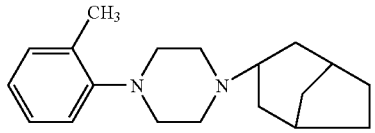 | 143 | 285.20 | 2.22 |
| 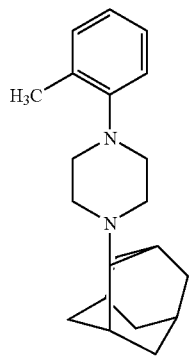 | 144 | 311.20 | 2.37 |
| 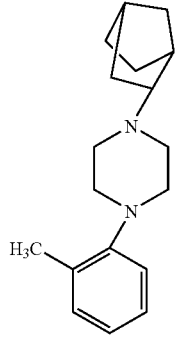 | 145 | 272.10 | 2.35, 2.10 |
| 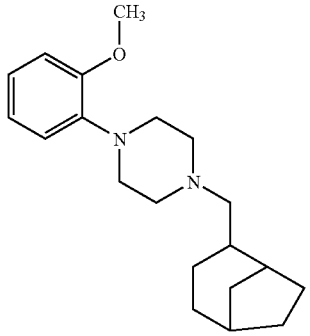 | 146 | 314.20 | 2.11 |

-continued
| Compound | Cmpd # | LC/MS m/z | LC-RT (min) |
|---|---|---|---|
| 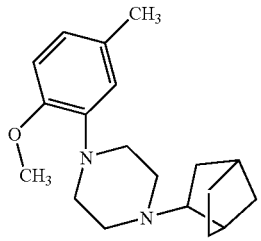 | 147 | 301.20 | 2.01 |
| 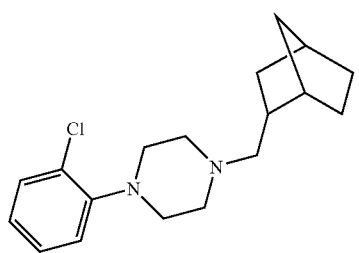 | 148 | 305.30 | 2.58 |
| 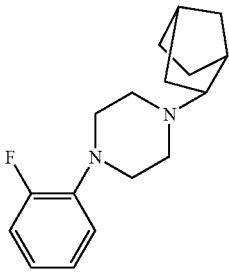 | 149 | | |
| 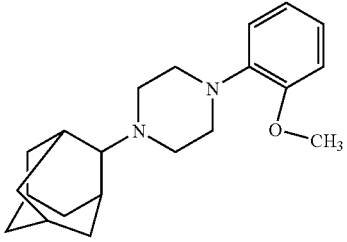 | 151 | 327.20 | 2.14 |
| 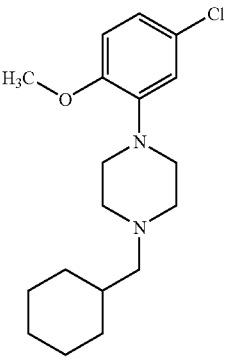 | 152 | 323.30 | 3.09 |

-continued
| Compound | Cmpd # | LC/MS m/z | LC-RT (min) |
|---|---|---|---|
| 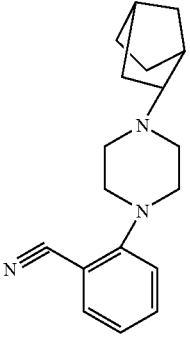 | 153 | 282.30 | 2.09 |
| 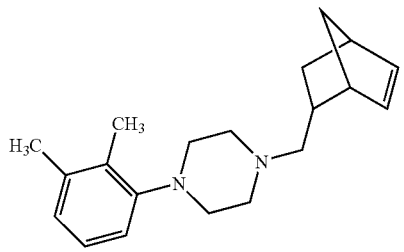 | 155 | 297.40 | 2.41 |
| 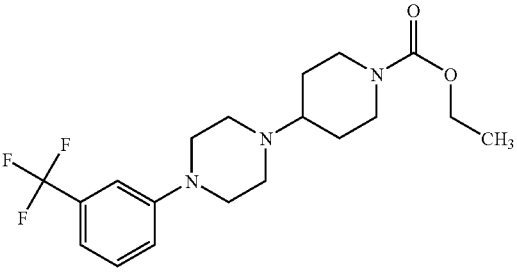 | 156 | | |
| 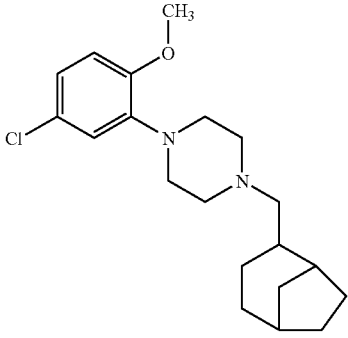 | 157 | 348.20 | 2.66 |
| 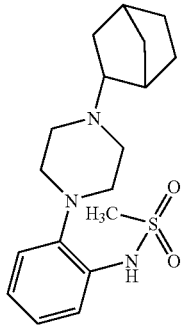 | 158 | 350.20 | 1.82 |

-continued

| Compound | Cmpd # | LC/MS m/z | LC-RT (min) |
|---|---|---|---|
| | 160 | 326.20 | 1.64 |
| | 161 | 330.40 | 1.92 |
| | 162 | 314.20 | 1.52 |
| | 163 | 341.00 | 2.72 |

-continued
| Compound | Cmpd # | LC/MS m/z | LC-RT (min) |
|---|---|---|---|
| 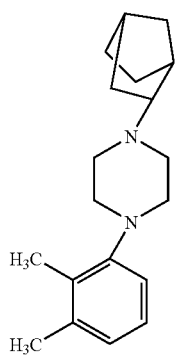 | 166 | 285.20 | 2.26 |
| 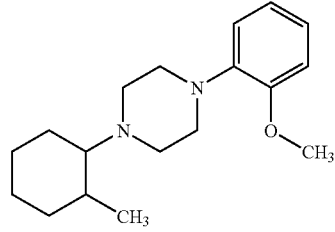 | 167 | 289.00 | 1.93 |
| 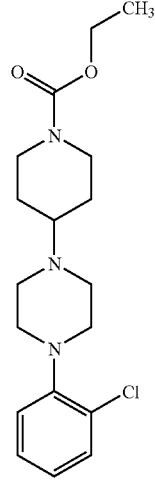 | 168 | 352.20 | 1.99 |
| 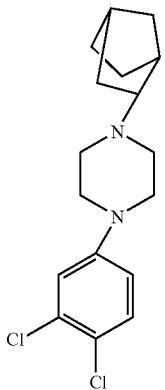 | 169 | 325.20 | 2.29 |

-continued

| Compound | Cmpd # | LC/MS m/z | LC-RT (min) |
|---|---|---|---|
| | 170 | 301.10 | 2.25 |
| | 172 | | |
| | 175 | 297.10 | 2.64 |
| | 176 | 321.00 | 2.34 |
| | 177 | 395.00 | 2.35 |

-continued
| Compound | Cmpd # | LC/MS m/z | LC-RT (min) |
|---|---|---|---|
| 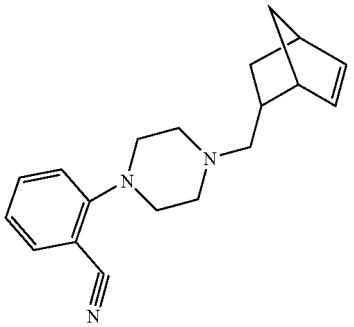 | 178 | 294.30 | 2.35 |
| 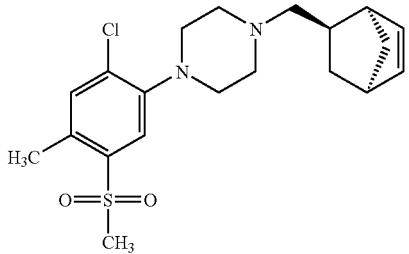 | 179 | 395.00 | 2.36 |
| 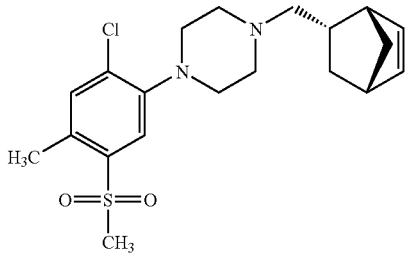 | 180 | 395.00 | 2.36 |
| 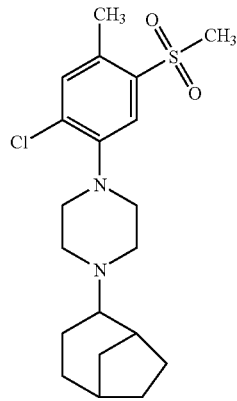 | 181 | 397.20 | 2.29 |
| 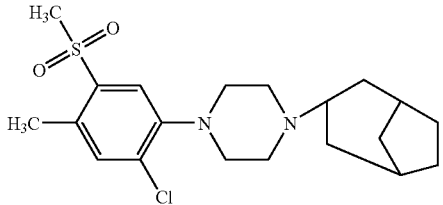 | 182 | 397.00 | 2.34 |

-continued

| Compound | Cmpd # | LC/MS m/z | LC-RT (min) |
|---|---|---|---|
| (structure) | 183 | 444.20 | 2.14 |
| (structure) | 184 | 387.00 | 2.02 |
| (structure) | 185 | 385.00 | 2.35 |

-continued
| Compound | Cmpd # | LC/MS m/z | LC-RT (min) |
|---|---|---|---|
| 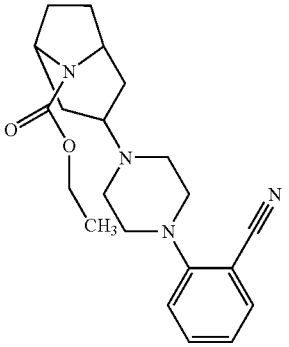 | 186 | 369.00 | 2.16 |
| 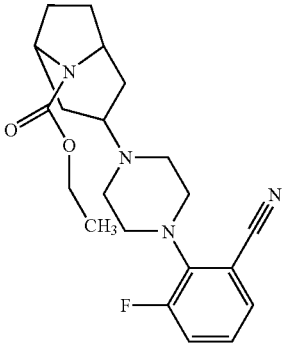 | 187 | 387.20 | 2.14 |
| 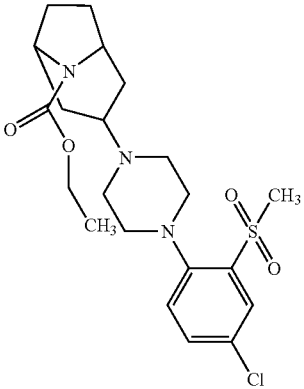 | 188 | 456.20 | 2.24 |
| 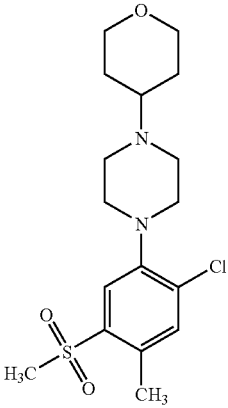 | 189 | 373.00 | 1.83 |

-continued

| Compound | Cmpd # | LC/MS m/z | LC-RT (min) |
|---|---|---|---|
| | 190 | 287.20 | 1.82 |
| | 191 | 349.20 | 2.30 |
| | 192 | 337.40 | 2.45 |

The A-ring in examples 96, 102, 106, 125, 129, 139, 140, 150, 160, and 177 may also be illustrated as

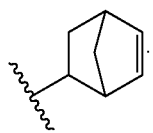

The A ring in examples 112, 134, 162, and 190 may also be illustrated as

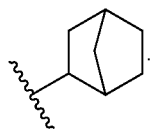

The A ring in example 118 may also be illustrated as

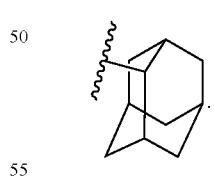

Example 8

Functional Mobilization of Intracellular Calcium to Determine Muscarinic Receptor Activity CHO cells expressing muscarinic receptors (M1 to M5) are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 µg/ml of Streptomycin (GIBCO Cat# 15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Versene (GIBCO Cat# 15040-066), collected by centrifugation and seeded 18-24 hrs prior to running the calcium assay at a density of 5,000-10,000 cells/well in back-walled, clear-bottomed 384-well plates (BD Biocoat, poly-D-lysine, Cat#356663). The day of the experiment, the cells are washed with a plate washer (Bioteck Instruments, ELX 405) using bath1 buffer (140-mM NaCl, 4.5-mM KCl, 2-mM $CaCl_2$, 1-mM $MgCl_2$, 10-mM Hepes-Na, 10-mM Glucose, pH 7.4, with NaOH) containing 1 mM Probenecid. Next, the calcium dye Fluo-3 (25 µl/well of Fluo-3 AM at 4 µM, Molecular Probes F-1241, in Bath 1 buffer containing 1 mM Probenecid) is added to the 25 µl of Bath 1 remaining in each well after the plate wash and the dye is loaded at 37° C. in the tissue culture incubator for 60-90 min. The fluorescent dye is removed using the plate washer with Bath 1 containing 1 mM Probenecid, leaving 25 µl/well of this solution after the wash. Alternatively, cells can be loaded with the calcium indicator from Molecular Devices (Calcium 3 Assay Reagents, Cat # R7181) adding 5 µl of a 5× solution dye in Bath 1 containing 1 mM Probenecid (10 ml per dye flask cat# R7182 to generate a solution 20×) to 20 µl of the same buffer. After loading for 60 min, the experiment can be run without having to remove the dye.

Compounds are prepared at a 2× fold concentration in a 96-well plate (round bottom, Costar Corning cat# 3656), by reconstituting the pre-spotted compounds in bath 1 containing 1 mM probenecid. The final concentration DMSO is 0.5%, and the amount of DMSO is normalized across the assay plate. To determine an agonist action of the compounds on muscarinic receptors, the reconstituted compounds are added (25 µl compound/well) to the cell assay plate (containing 25 µl/well) using the multi-channel robotic system of the FLIPR 3 Instrument (Molecular Devices, Sunnyvale, Calif.). To determine a functional inhibitory action of the compounds on muscarinic receptors, the reconstituted compounds are added (25 µl compound/well) to the assay plate and pre-incubated for 15 min prior to adding 25 µl of Carbachol at 3× the EC80 for each muscarinic subtype. Alternatively, the compounds can be co-applied simultaneously with the agonist. In both assay modes, the fluorescence is recorded for 60 sec (excitation wavelength is 488 nM and emission wavelength 540 nm) using the FLIPR 3 instrument.

The potency, efficacy and selectivity of the muscarinic compounds were evaluated by screening the compound activity across the whole family (M1 to M5 cells).

The compounds of the present invention were found to selectively modulate the muscarinic receptors selectively over the other receptor types.

EXAMPLE 9

β-Lactamase Assay to Determine Muscarinic Receptor Activity

CHO cells expressing muscarinic receptors (M1 to M5) and containing a gene reporter system (β-Lactamase) with transcriptional control mediated by calcium release (NFAT activation). See Zlokarnik, G; Negulescu, P. A.; Knapp, T. E.; Mere, L; Burres, N; Feng, L; Whitney, M; Roemer, K; Tsien, R. Y. Quantitation of transcription and clonal selection of single living cells with β-lactamase as reporter. Science, 1998 Jan 2, 279(5347):84-8. The cells are grown as monolayers in tissue culture flasks at 37° C. in a humidified atmosphere containing 5% $CO_2$ and passaged every 3-5 days. The growth media is Dulbecco's modified eagles medium (DMEM, Gibco Cat# 12430-054), containing 25 mM Hepes and supplemented with 10% Fetal Bovine Serum (Hyclone, cat# SH30071.03), 0.1 mM of MEM non-essential amino acids (GIBCO, Cat# 11140-050), 1 mM MEM Sodium Pyruvate (GIBCO Cat# 11360-070) and 100 units/ml of Penicillin G and 100 µg/ml of Streptomycin (GIBCO Cat# 15140-122). The recombinant muscarinic receptor cell lines are grown under antibiotic pressure with media containing 25 µg/ml zeocin and 500 µg/ml G418 (M1-CHO), 4 µg/ml puromycin, 50 µg/ml zeocin and 2.5 µg/ml blasticidin (M2 and M4-CHO) or 50 µg/ml zeocin and 4 µg/ml puromycin (M3 and M5-CHO).

Cells are harvested at 80-90% confluence using Accutase (Innovative Cell Technologies, Inc. Cat# AT104), collected by centrifugation and seeded for 2-6 hours at a density of 15,000-20,000 cells/well in black-walled, clear-bottomed 384-well plates (BD Biocoat, poly-D-lysine, Cat#356663). Media is replaced with DMEM +1% Fetal Bovine Serum and incubated for another 12-18 hrs prior to running the β-Lactamase assay. The day of the experiment, compounds are prepared at a 1× fold concentration in a 96-well plate (round bottom, Costar Corning cat# 3656), by reconstituting the pre-spotted compounds in DMEM +1% FBS. The final concentration of DMSO is 0.5%, and the amount of DMSO is normalized across the assay plate. To determine an agonist action of the compounds on muscarinic receptors, the reconstituted compounds are added (25 µl compound/well) to the cell assay plate (where the media has been removed) using the multi-channel robotic system, Multimek 96 (Beckman). The compounds are incubated with the cells for 3 hours at 37° C., 5% $CO_2$. to allow for expression of the reporter gene β-Lactamase.

After 3 hours, 5 µg of 6× fold concentrated CCF2/AM dye are added to the assay plates and incubated at room temperature for 1 hour. Fluorescent emission at two wavelengths (460 nm and 530 nm) is determined using the CytoFluor Series 4000 (PerSeptive Biosystems) and the calculations for reporter gene expression determined as specified in prior publications {Zlokarnik, G; Negulescu, P. A.; Knapp, T. E.; Mere, L; Burres, N; Feng, L; Whitney, M; Roemer, K; Tsien, R. Y. Quantitation of transcription and clonal selection of single living cells with β-lactamase as reporter. Science, 1998 Jan 2, 279(5347):84-8.}

The compounds of the present invention were found to modulate the muscarinic receptor activity using the β-Lactamase Assay.

What is claimed is:

1. A compound having formula (II):

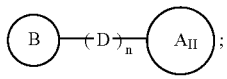

wherein:
B is selected from

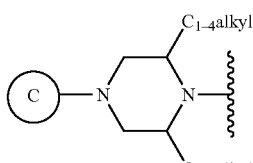

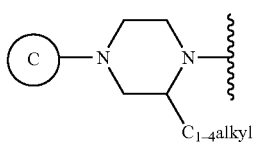

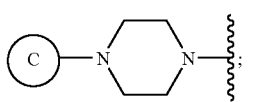

D is $CF_2$, $CH_2$, or $CHR^9$;
Ring C is phenyl optionally substituted with 1 to 4 of $R^1$, $R^2$, $R^3$, $R^4$, or $R^5$;
ring $A_{II}$ is selected from:

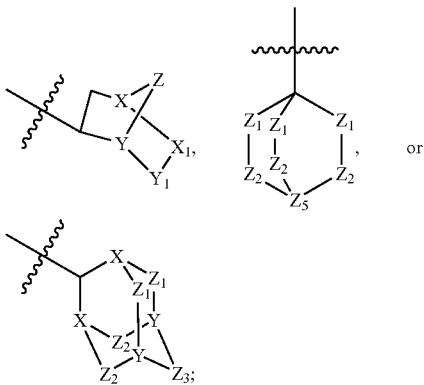

X, Y, and $Z_5$ are each independently CR';
$X_1$ and $Y_1$ are independently selected from a bond, $CH_2$, $CHR^9$, C(O), or $X_1$ and $Y_1$ are together —CH=CH—, provided that both $X_1$ and $Y_1$ are not simultaneously a bond;
Each Z is independently $C(R')_2$, $C(R')_2$—$C(R')_2$, or $C(R')_2$-Q, wherein Q is O, NR', S(O), $SO_2$, or C(O);
Each of $Z_1$, $Z_2$, and $Z_3$ is independently selected from CHR', or C(O);
Each R' is independently selected from (C1-C4)aliphatic$_m$-$Q^1$, $S(O)_iR^6$, $S(O)_iR^5$, $SO_2N(R^6)_2$, $SO_2N(R^5)_2$, $SO_2NR^5R^6$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)$ $R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $R^2$, or $R_6$;

Each $R^1$ is independently oxo or ((C1-C4)aliphatic)$_m$-$Q^1$;
Each $Q^1$ is independently halo, CN, $NO_2$, $CF_3$, $OCF_3$, OH, $SR^6$, $S(O)R^6$, $SO_2R^6$, $N(R^6)_2$, $NR^6R^8$, COOH, $COOR^6$ or $OR^6$;
Each $R^2$ is independently aliphatic optionally substituted with 1-3 substituents independently selected from $R^1$, $R^4$, or $R^5$;
Each $R^3$ is independently a cycloaliphatic, aryl, heterocyclic, or heteroaryl ring, wherein each of the cycloaliphatic, aryl, heterocyclic, or heteroaryl are optionally substituted with 1-3 substituents independently selected from $R^1$, $R^2$, $R^4$, or $R^5$;
Each $R^4$ is independently $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $S(O)_iR^6$, $S(O)_iR^5$, $SO_2N(R^6)_2$, $SO_2N(R^5)_2$, $SO_2NR^5R^6$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^6C(O)OR^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;
Each $R^5$ is independently a cycloaliphatic, aryl, heterocyclic, or heteroaryl ring, wherein each of the cycloaliphatic, aryl, heterocyclic, or heteroaryl are optionally substituted with 1 to 3 of $R^1$;
Each $R^6$ is independently H or aliphatic optionally substituted with $R^7$;
Each $R^7$ is independently a cycloaliphatic, aryl, heterocyclic, or heteroaryl ring, wherein each of the cycloaliphatic, aryl, heterocyclic, or heteroaryl are optionally substituted with 1 to 2 of ($C_1$-$C_6$)-straight or branched alkyl, ($C_2$-$C_6$) straight or branched alkenyl or alkynyl, 1,2-methylenedioxy, 1,2-ethylenedioxy, or $(CH_2)_n$-$Q^2$;
Each $Q^2$ is independently selected from halo, CN, $NO_2$, $CF_3$, $OCF_3$, OH, S-aliphatic, S(O)-aliphatic, $SO_2$-aliphatic, COOH, C(O)O-aliphatic, or O-aliphatic;
Each $R^8$ is independently an amino protecting group;
Each $R^9$ is independently $R^2$, $R^3$, or $R^6$;
Each i is 0, 1, 2, or 3;
Each m is 0 or 1;
Each n is 0 or 1; and
Further provided that:
(i) when C is dimethyl-fluoro-phenyl, n is 1, D is $CH_2$, Z is $C(CH_3)_2$, X and Y are both CH, and B is piperazine, then $X_1$ and $Y_1$ are not both $CH_2$; and
(ii) when C is phenyl substituted with $R^2$, D is $CH_2$, n is 1, and B is piperazine, then ring $A_{II}$ is not adamantanyl; and
(iii) the compound is not 1-phenyl-4-4(tricycle[3.3.1.13,7]dec-1ylmethyl-piperazine.

2. The compound according to claim 1, wherein ring $A_{II}$ is

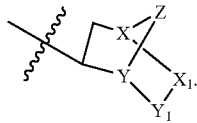

3. The compound according to claim 2, wherein X and Y are CH.
4. The compound according to claim 2, wherein $X_1$ and $Y_1$ are both $CH_2$.
5. The compound according to claim 2, wherein $X_1$ and $Y_1$ together form —CH=CH—.
6. The compound according to claim 2, wherein Z is $CH_2$.
7. The compound according to claim 2, wherein Z is C(O), —$CH_2$—C(O)—, or —C(O)—$CH_2$—.
8. The compound according to claim 1, wherein ring $A_{II}$ is

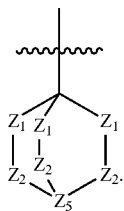

9. The compound according to claim 8, wherein each of $Z_1$ and $Z_2$ is independently $CH_2$, CHR', or C(O).
10. The compound according to claim 8, wherein each of $Z_1$ and $Z_2$ is independently $CH_2$.
11. The compound according to claim 1, wherein ring $A_{II}$ is

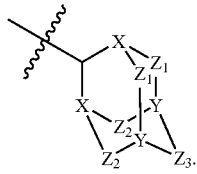

12. The compound according to claim 11, wherein each of $Z_1$ and $Z_3$ is independently $CH_2$.
13. The compound according to claim 11, wherein each of X and Y is CR'.
14. The compound according to claim 11, wherein each of X and Y is CH.
15. The compound according to claim 1 wherein B is piperazine.
16. The compound according to claim 1 selected from a)
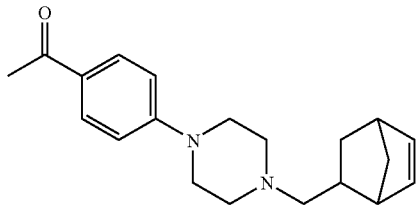

b)
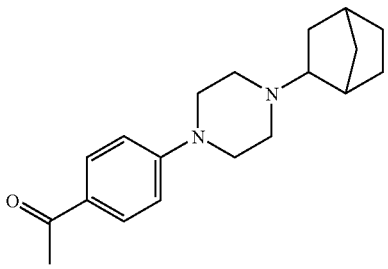

c)
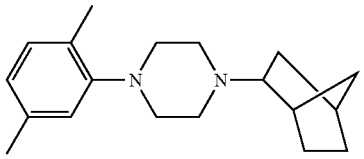

d)
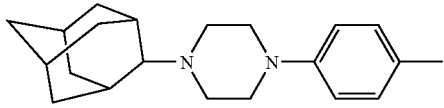

e)
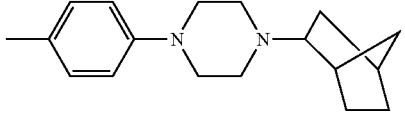

f)
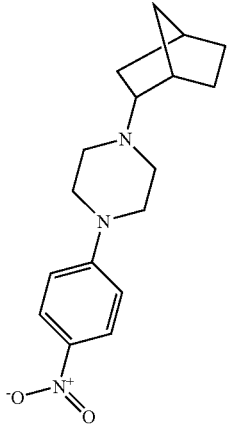

g)
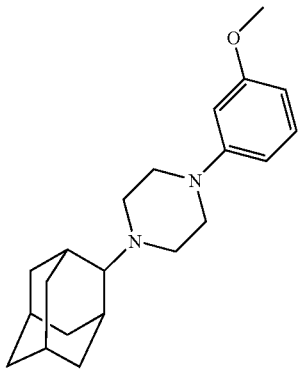

h) 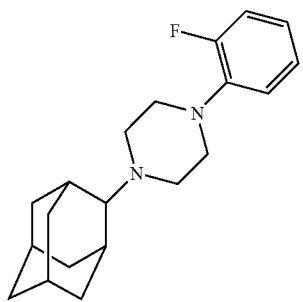
i) 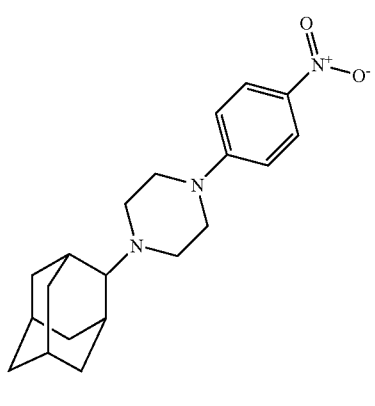
j) 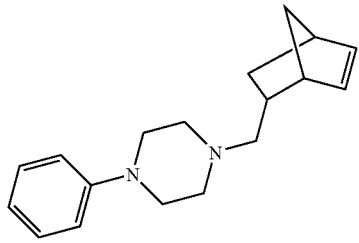
k) 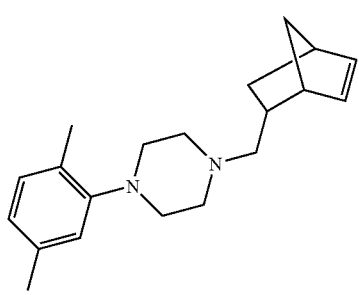
l) 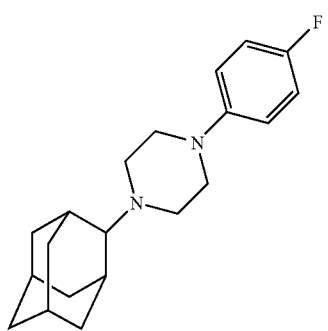
m) 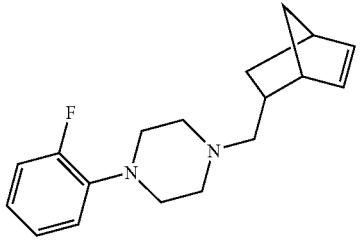
n) 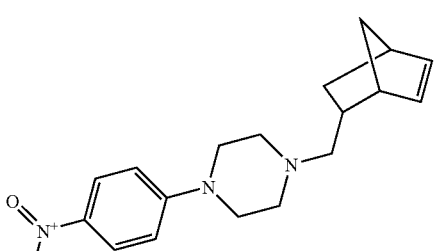
o) 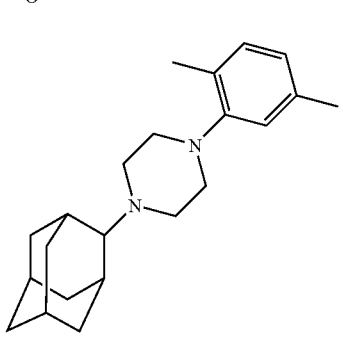
p) 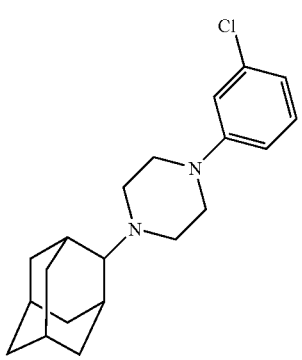
q) 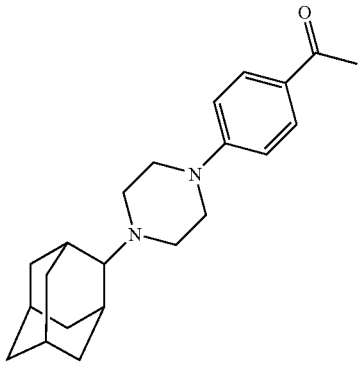

r) 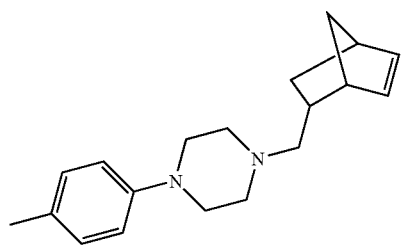
s) 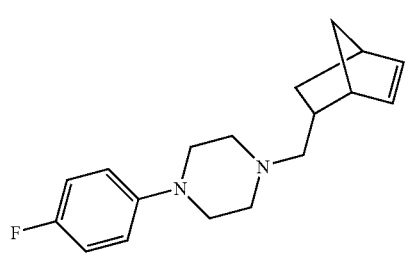
t) 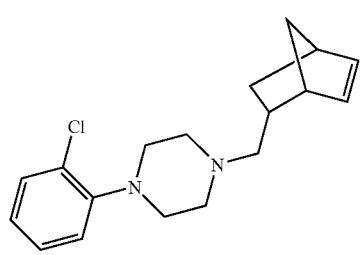
u) 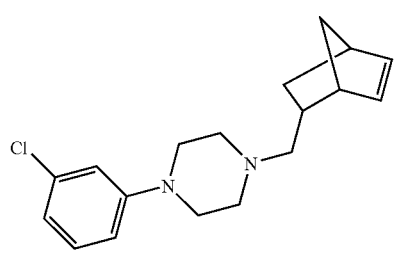
v) 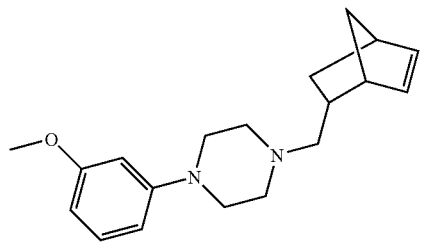
w) 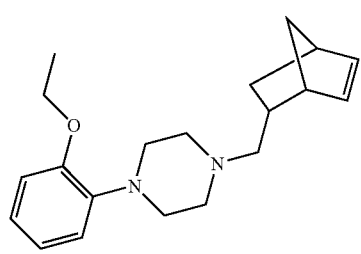
x) 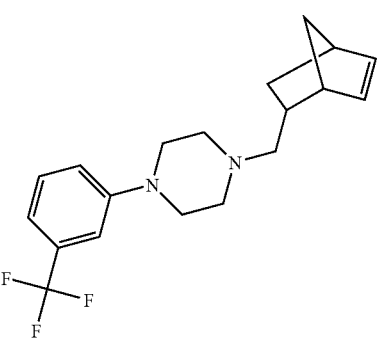
y) 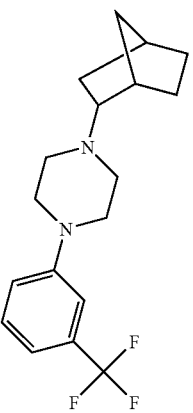
z) 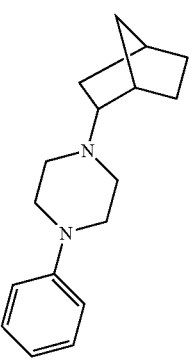
aa) 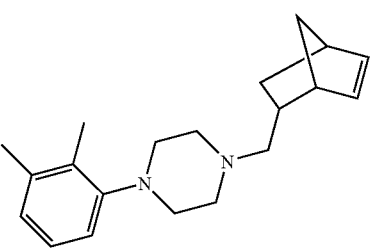
bb) 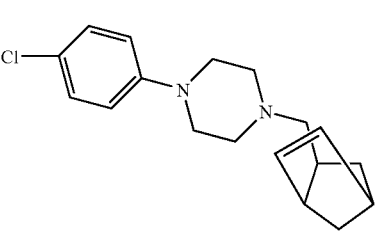

-continued
cc) 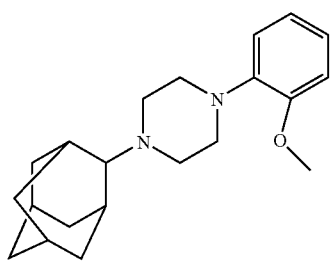
dd) 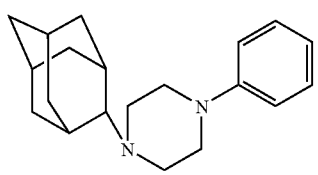
ee) 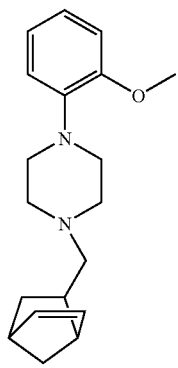
ff) 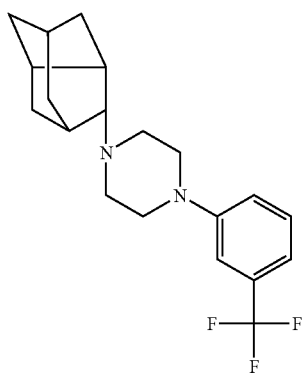
gg) 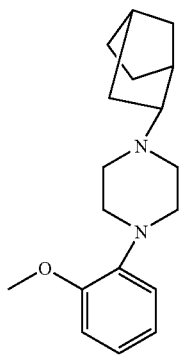
-continued
hh) 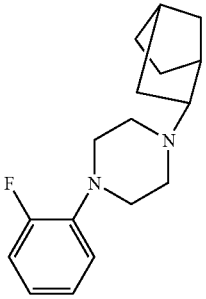
ii) 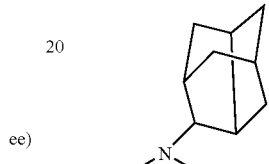
jj) 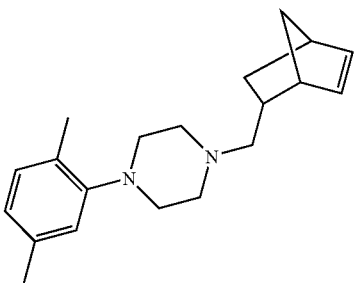
kk) 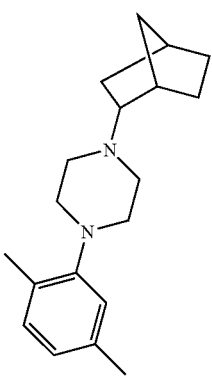

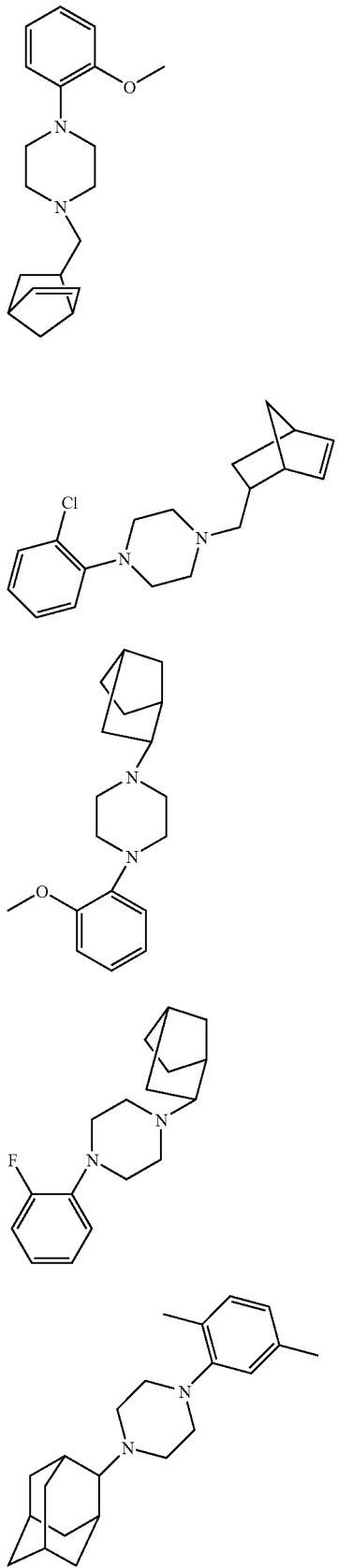
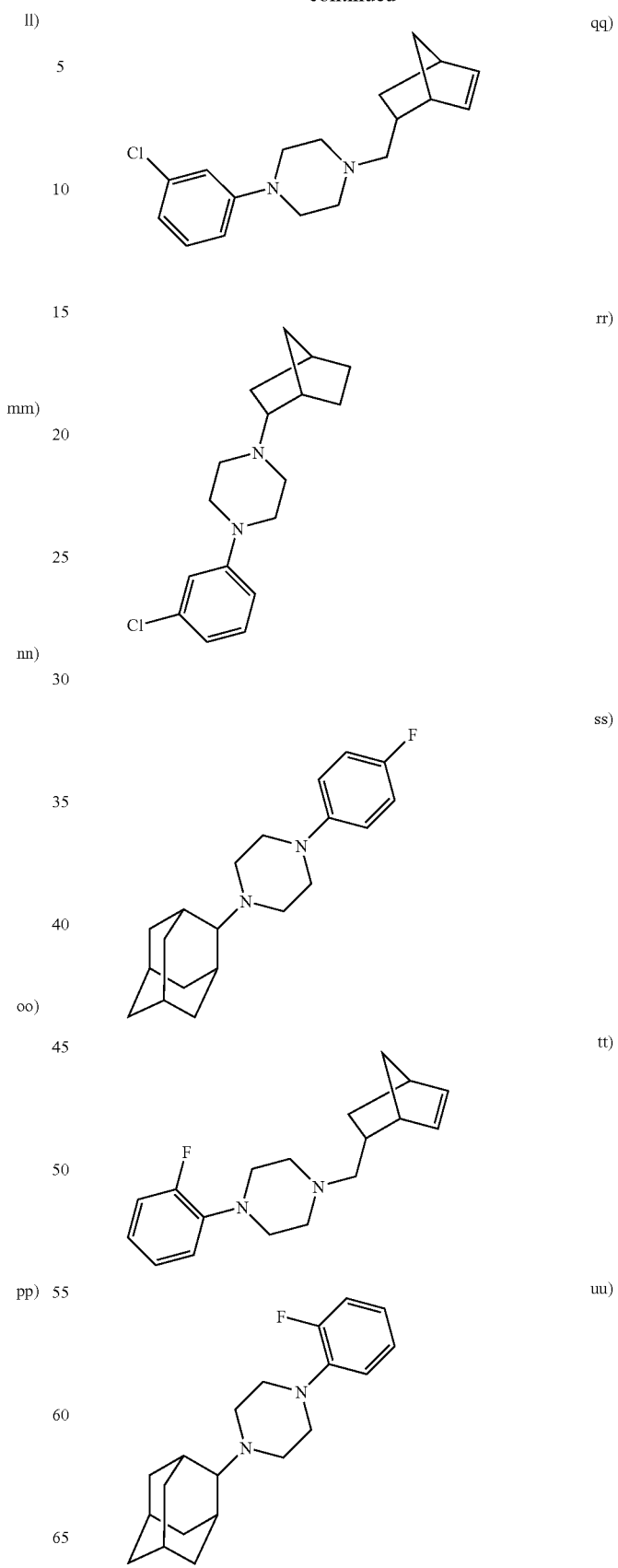

vv)
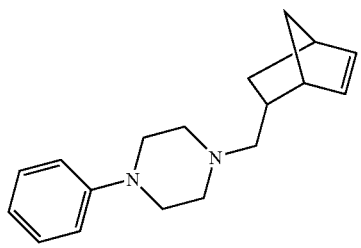
ww)
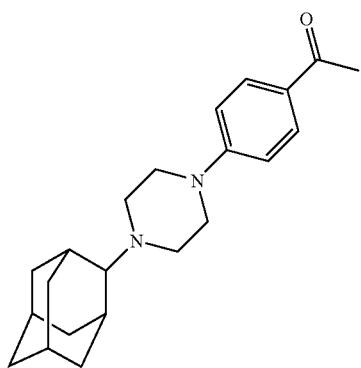
xx)
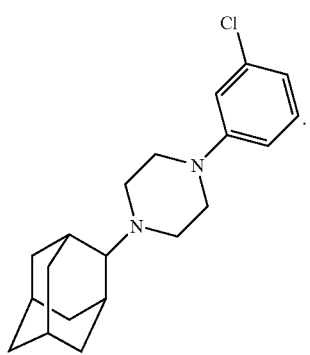
17. The compound according to claim 1 selected from
89
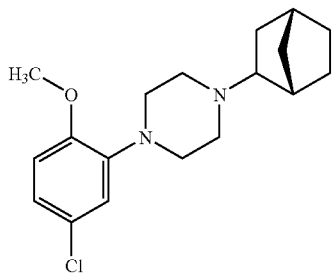
90
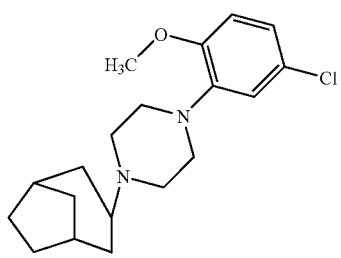
91
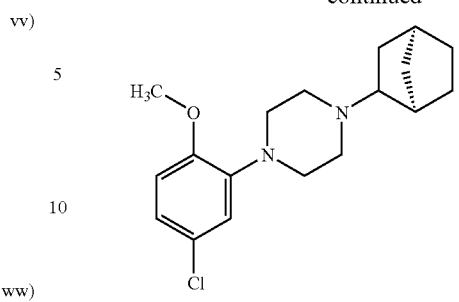
92
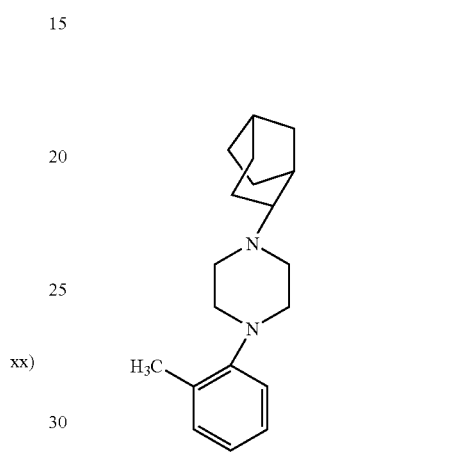
93
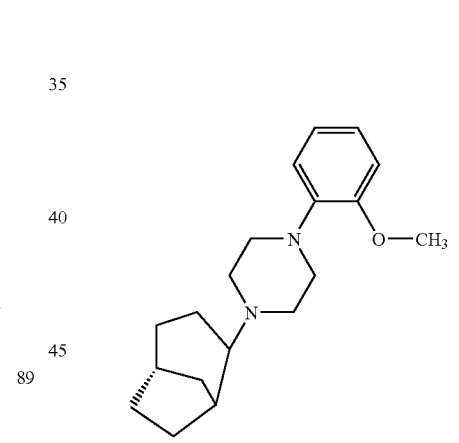
94
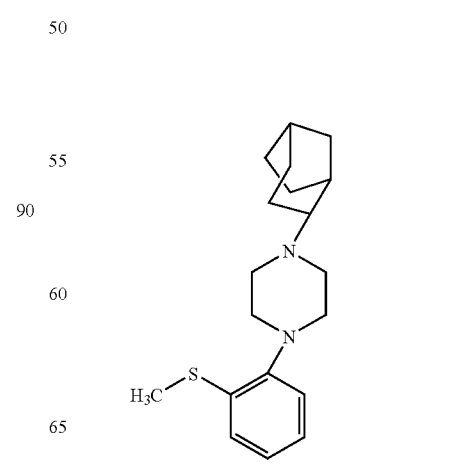

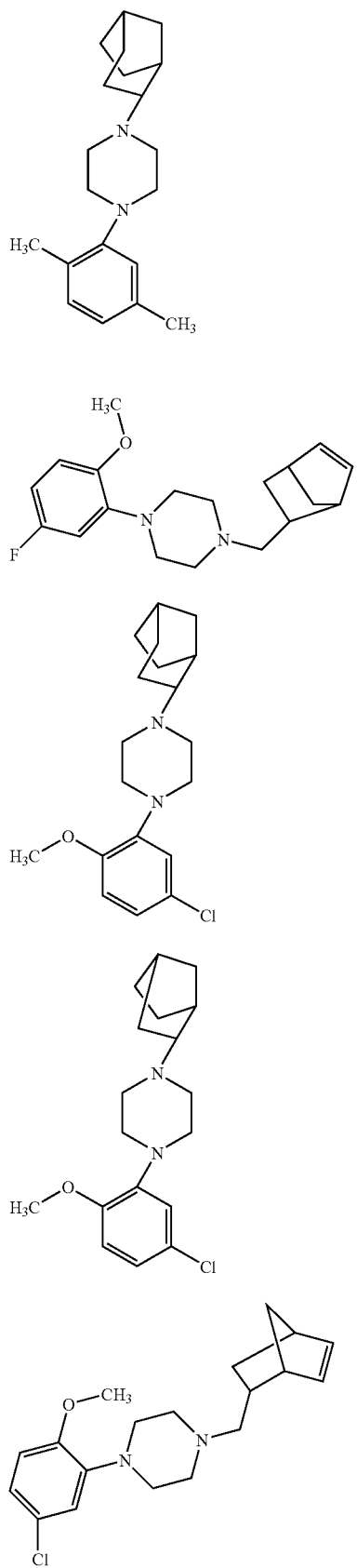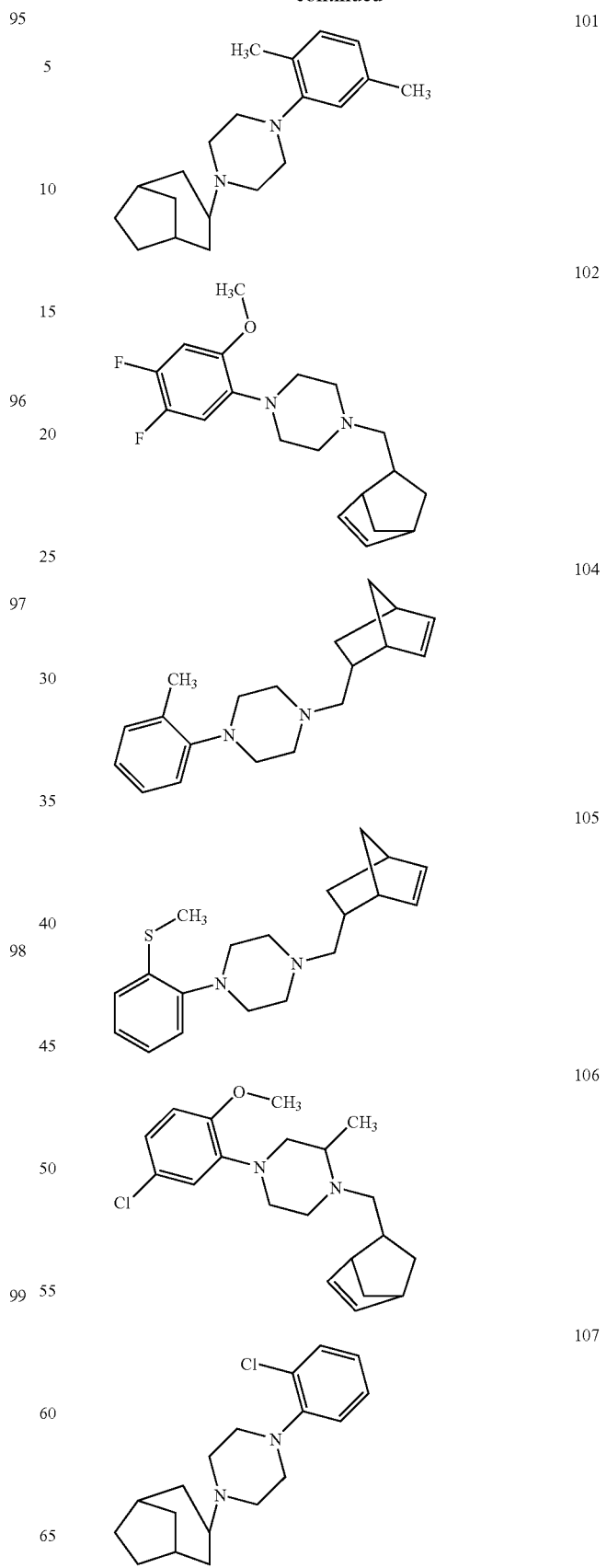

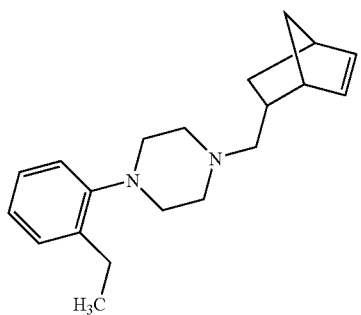
108
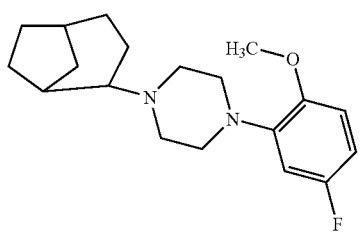
109
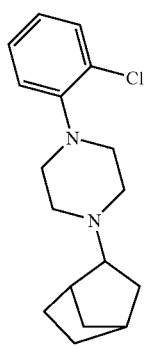
112
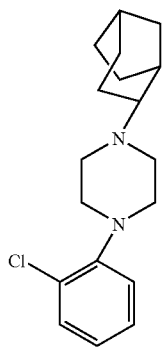
114
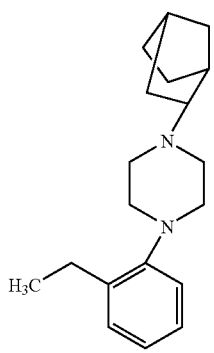
115
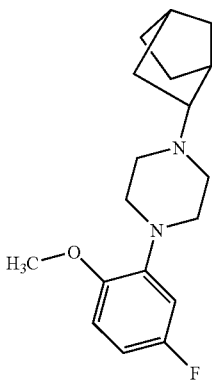
116
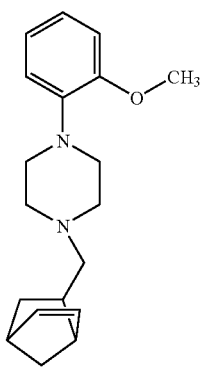
119
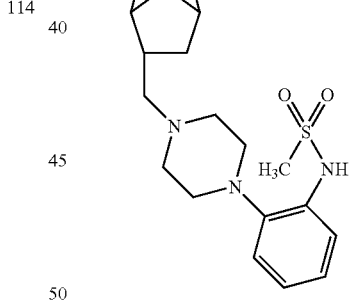
121
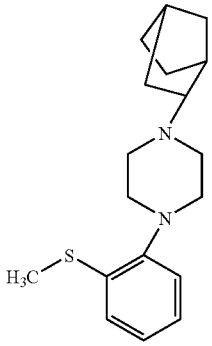
122

-continued
125 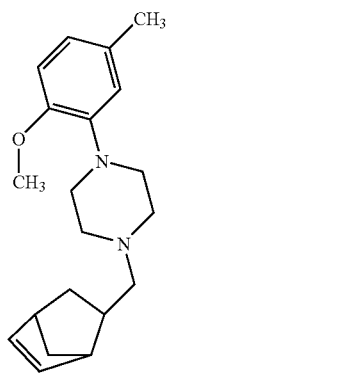
126 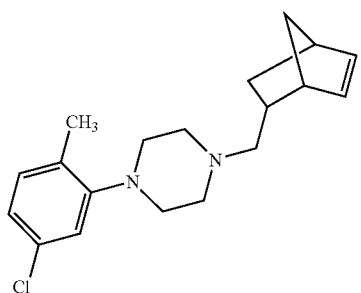
127 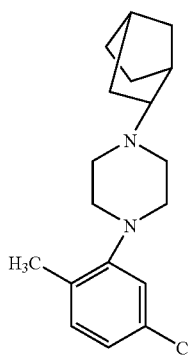
128 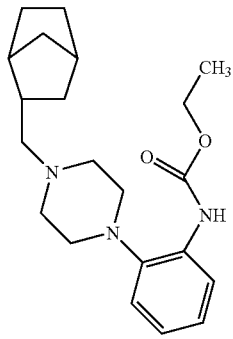
129 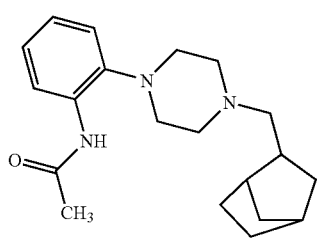
-continued
130 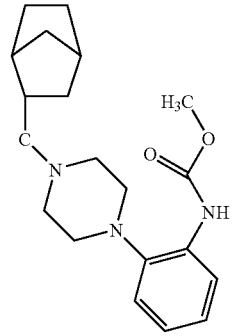
131 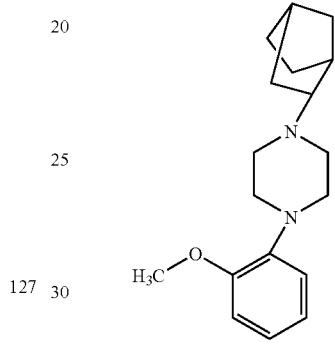
132 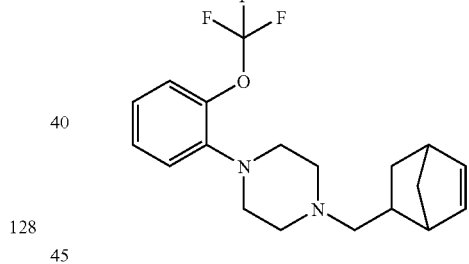
134 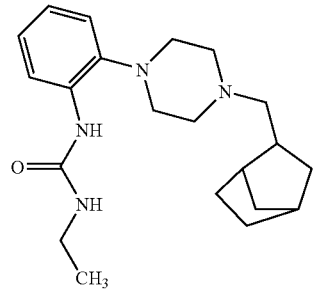
135 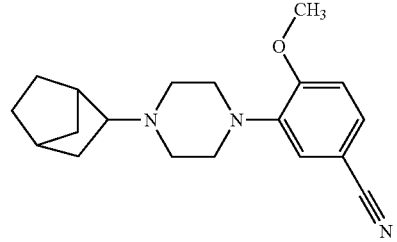

-continued
136 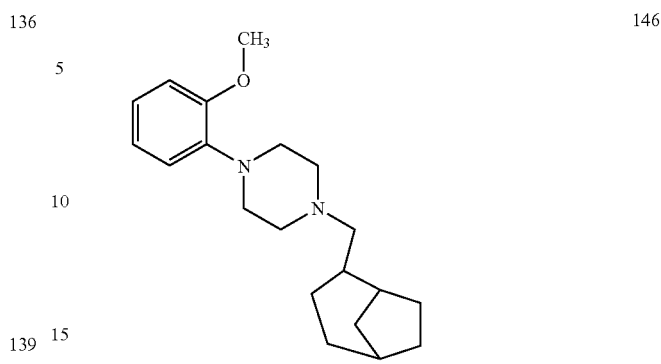
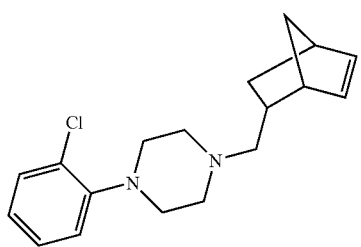
139 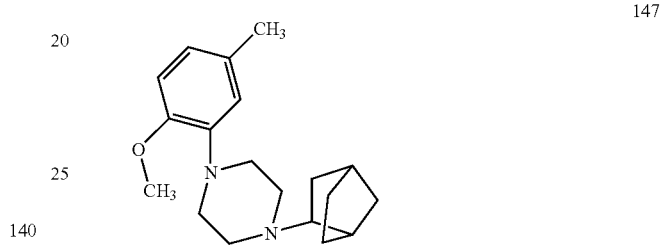
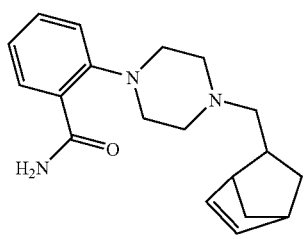
140 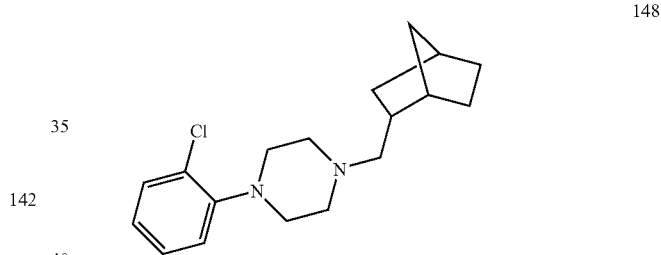
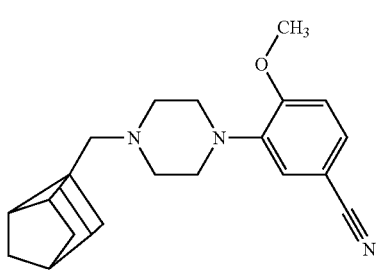
142 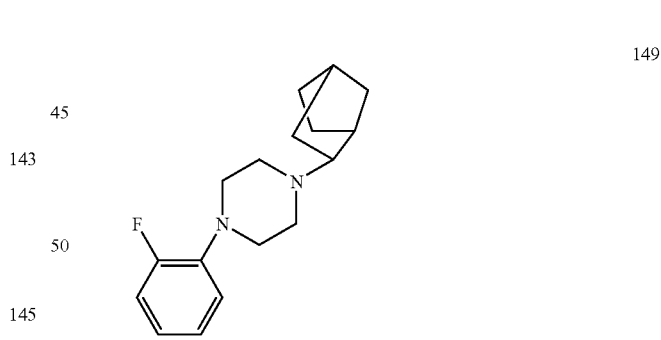
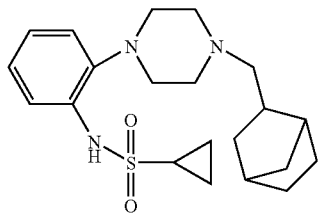
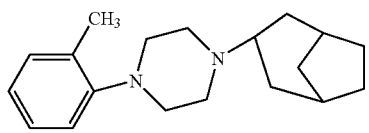
145 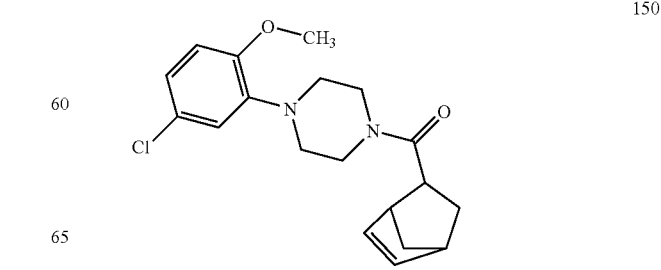
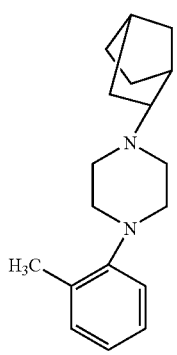

153 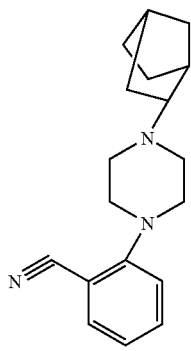
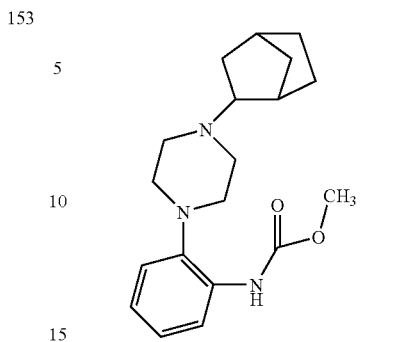
161
155 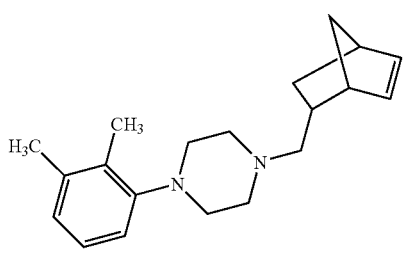
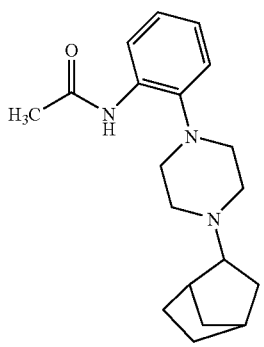
162
157 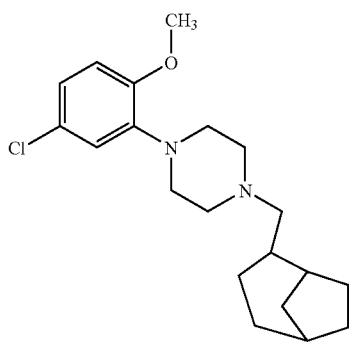
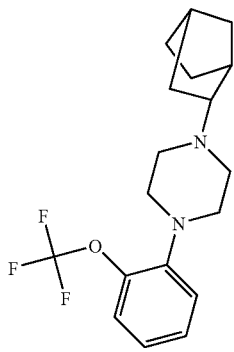
163
158 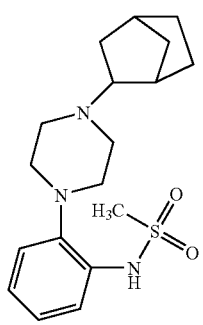
160 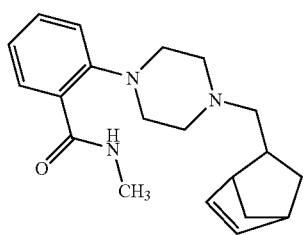
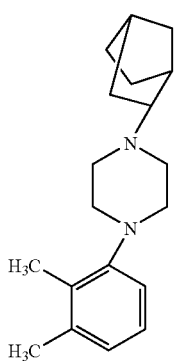
166

117 118
-continued -continued
| | |
|---|---|
| 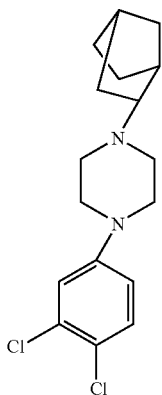 169 | 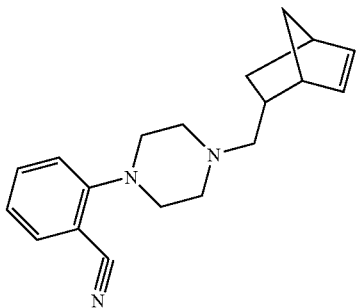 178 |
| 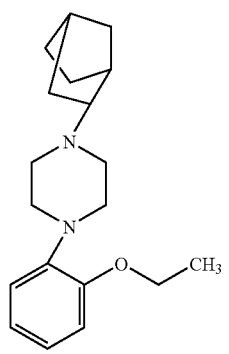 170 | 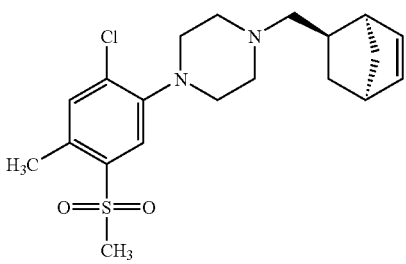 179 |
| 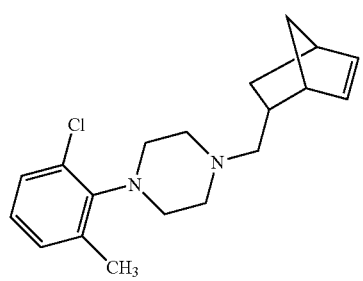 175 | 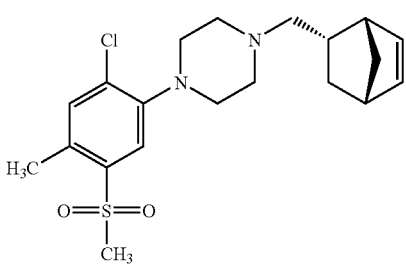 180 |
| 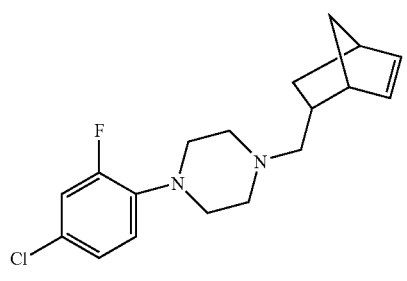 176 | 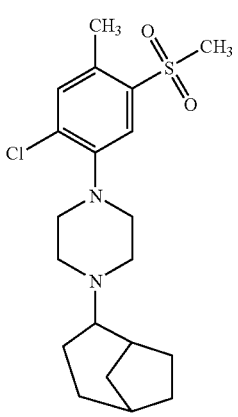 181 |
| 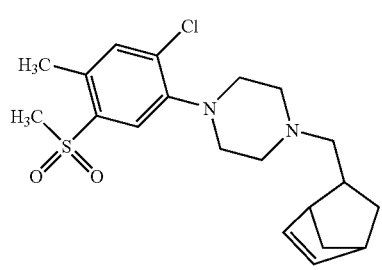 177 | 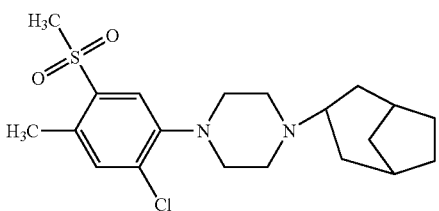 182 |

-continued

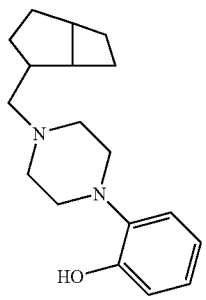

190

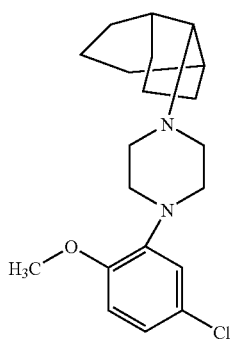

191

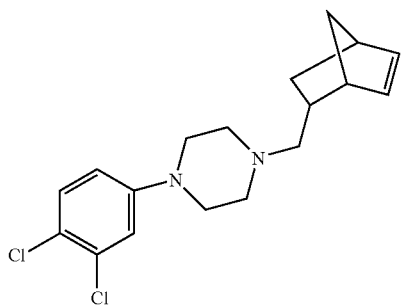

192

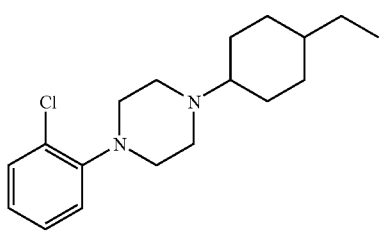

193

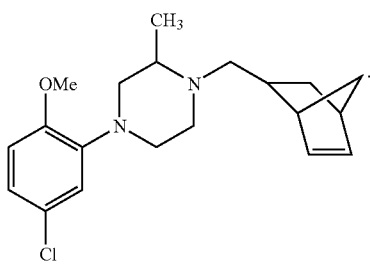

194

18. A compound of formula III

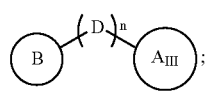

wherein:
B is selected from

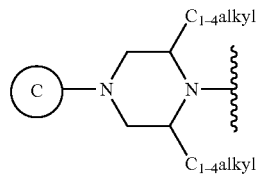

(i)

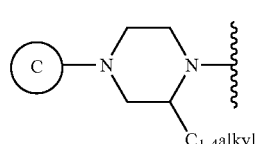

(ii)

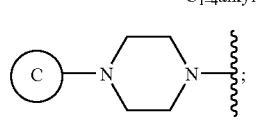

(iii)

D is $CF_2$, $CH_2$, or $CHR^9$;
Ring C is phenyl optionally substituted with 1 to 4 of $R^1$, $R^2$, $R^3$, $R^4$, or $R^5$;
ring $A_{III}$ is

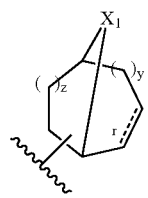

optionally substituted with 1-3 of R';
$X_1$ is independently selected from a bond, $CH_2$, $CHR^9$, or $C(O)$;
Each R' is independently selected from (C1-C4)aliphatic)$_m$-$Q^1$, $S(O)_iR^6$, $S(O)_iR^5$, $SO_2N(R^6)_2$, $SO_2N(R^5)_2$, $SO_2NR^5R^6$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $R^2$, or $R^6$;
Each $R^1$ is independently oxo or ((C1-C4)aliphatic)$_m$-$Q^1$;
Each $Q^1$ is independently halo, CN, $NO_2$, $CF_3$, $OCF_3$, OH, $SR^6$, $S(O)R^6$, $SO_2R^6$, $N(R^6)_2$, $NR^6R^8$, COOH, $COOR^6$ or $OR^6$;
Each $R^2$ independently is aliphatic optionally substituted with 1-3 substituents independently selected from $R^1$, $R^4$, or $R^5$;
Each $R^3$ is independently a cycloaliphatic, aryl, heterocyclic, or heteroaryl ring, wherein each of the cycloaliphatic, aryl, heterocyclic, or heteroaryl are optionally substituted with 1-3 substituents independently selected from $R^1$, $R^2$, $R^4$, or $R^5$;

Each $R^4$ is independently $OR^5$, $OR^6$, $OC(O)R^6$, $OC(O)R^5$, $OC(O)OR^6$, $OC(O)OR^5$, $OC(O)N(R^6)_2$, $OC(O)N(R^5)_2$, $OC(O)N(R^6R^5)$, $S(O)_iR^6$, $S(O)_iR^5$, $SO_2N(R^6)_2$, $SO_2N(R^5)_2$, $SO_2NR^5R^6$, $C(O)R^5$, $C(O)OR^5$, $C(O)R^6$, $C(O)OR^6$, $C(O)N(R^6)_2$, $C(O)N(R^5)_2$, $C(O)N(R^5R^6)$, $C(O)N(OR^6)R^6$, $C(O)N(OR^5)R^6$, $C(O)N(OR^6)R^5$, $C(O)N(OR^5)R^5$, $C(NOR^6)R^6$, $C(NOR^6)R^5$, $C(NOR^5)R^6$, $C(NOR^5)R^5$, $N(R^6)_2$, $N(R^5)_2$, $N(R^5R^6)$, $NR^5C(O)R^5$, $NR^6C(O)R^6$, $NR^6C(O)R^5$, $NR^5C(O)R^6$, $NR^5C(O)OR^6$, $NR^6C(O)OR^5$, $NR^5C(O)OR^5$, $NR^6C(O)N(R^6)_2$, $NR^6C(O)NR^5R^6$, $NR^6C(O)N(R^5)_2$, $NR^5C(O)N(R^6)_2$, $NR^5C(O)NR^5R^6$, $NR^5C(O)N(R^5)_2$, $NR^6SO_2R^6$, $NR^6SO_2R^5$, $NR^5SO_2R^5$, $NR^6SO_2N(R^6)_2$, $NR^6SO_2NR^5R^6$, $NR^6SO_2N(R^5)_2$, $NR^5SO_2NR^5R^6$, $NR^5SO_2N(R^5)_2$, $N(OR^6)R^6$, $N(OR^6)R^5$, $N(OR^5)R^5$, or $N(OR^5)R^6$;

Each $R^5$ is independently a cycloaliphatic, aryl, heterocyclic, or heteroaryl ring, wherein each of the cycloaliphatic, aryl, heterocyclic, or heteroaryl are optionally substituted with 1 to 3 of $R^1$;

Each $R^6$ is independently H or aliphatic optionally substituted with $R^7$;

Each $R^7$ is independently a cycloaliphatic, aryl, heterocyclic, or heteroaryl ring, wherein each of the cycloaliphatic, aryl, heterocyclic, or heteroaryl are optionally substituted with 1 to 2 of $(C_1-C_6)$-straight or branched alkyl, $(C_2-C_6)$ straight or branched alkenyl or alkynyl, 1,2-methylenedioxy, 1,2-ethylenedioxy, or $(CH_2)_n-Q^2$;

Each $Q^2$ is independently selected from halo, CN, $NO_2$, $CF_3$, $OCF_3$, OH, S-aliphatic, S(O)-aliphatic, $SO_2$-aliphatic, COOH, C(O)O-aliphatic, or O-aliphatic;

Each $R^8$ is independently an amino protecting group;

Each $R^9$ is independently $R^2$, $R^3$, or $R^6$;

Each i is 0, 1, 2, or 3;

Each m is 0 or 1;

Each n is 0 or 1;

Each y is 0, 1 or 2;

Each z is 0, 1, or 2 provided that y+z is 1, 2, or 3; and

Bond r is a single or double bond;

provided that when D is $CH_2$, y is 1 and z is 2, that $X_1$ is other than C(O) or —CH(OH)—.

19. The compound according to claim 18, wherein B is piperazine.

20. The compound of claim 18 selected from a)

b)

c)

d)

e)

f)

g)

-continued
h) 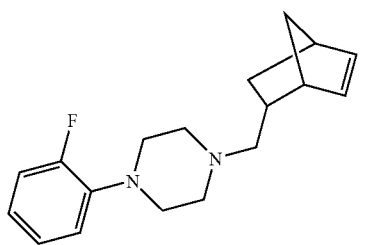
i) 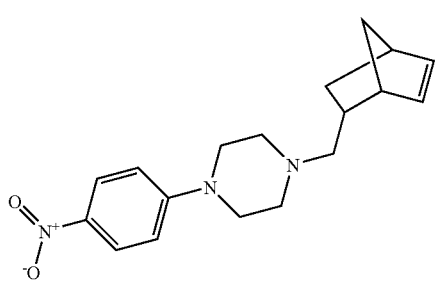
j) 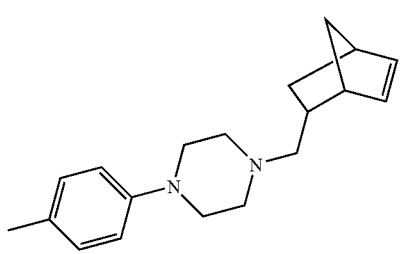
k) 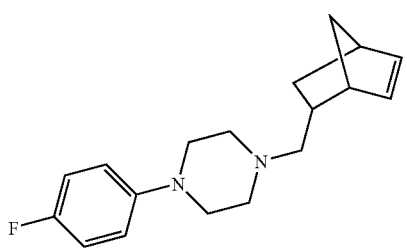
l) 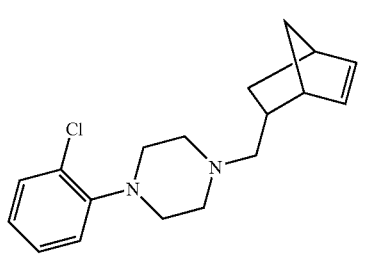
m) 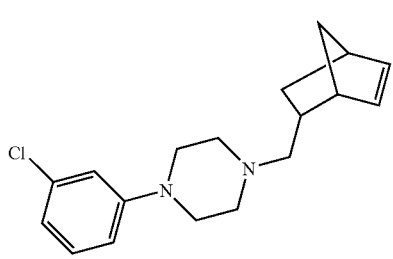
-continued
n) 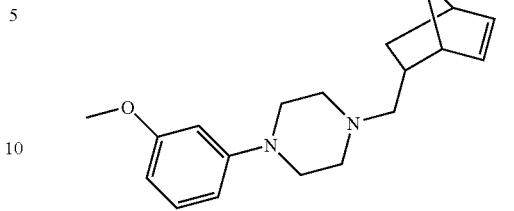
o) 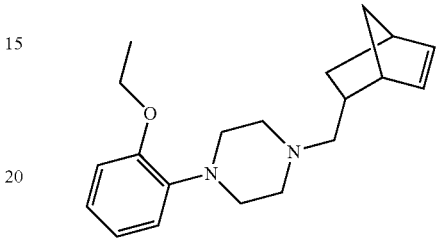
p) 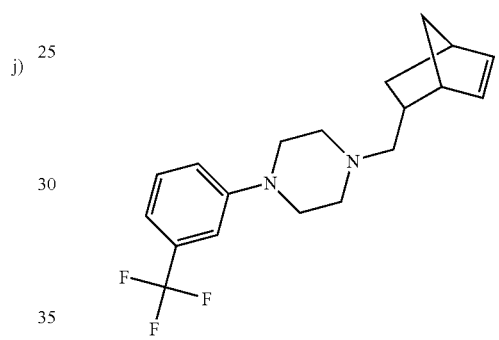
q) 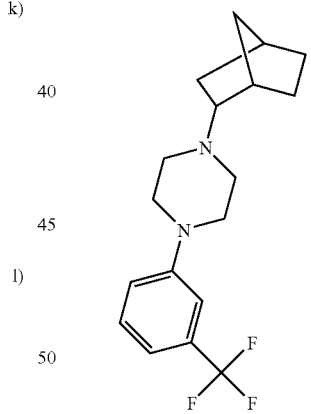
r) 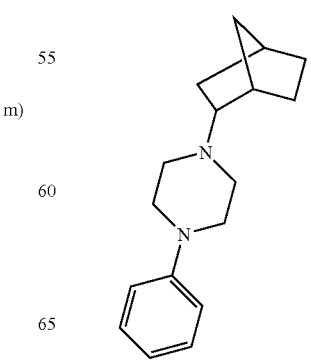

-continued
s)
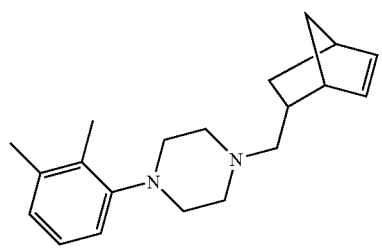
t)
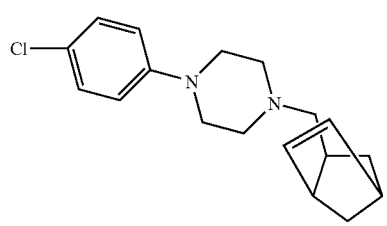
u)
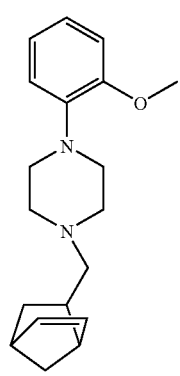
v)
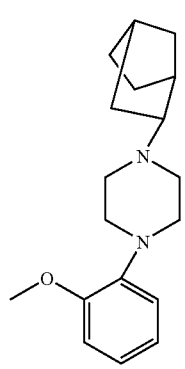
w)
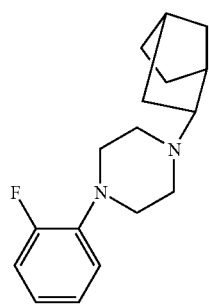
-continued
x)
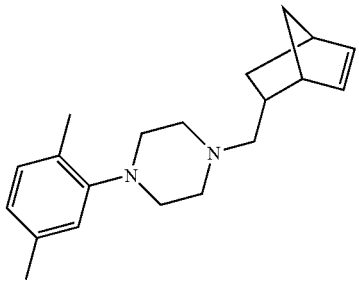
y)
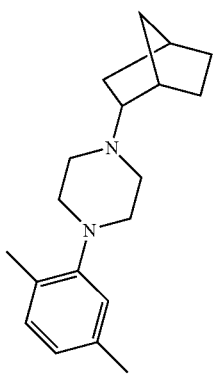
z)
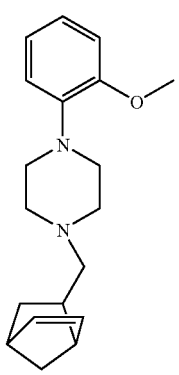
aa)
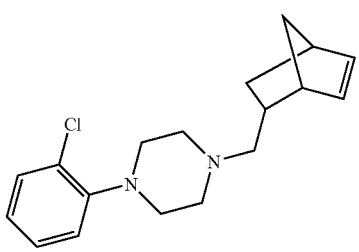
bb)
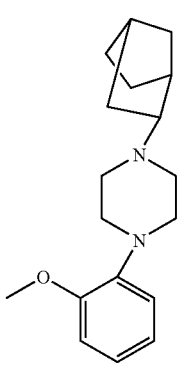

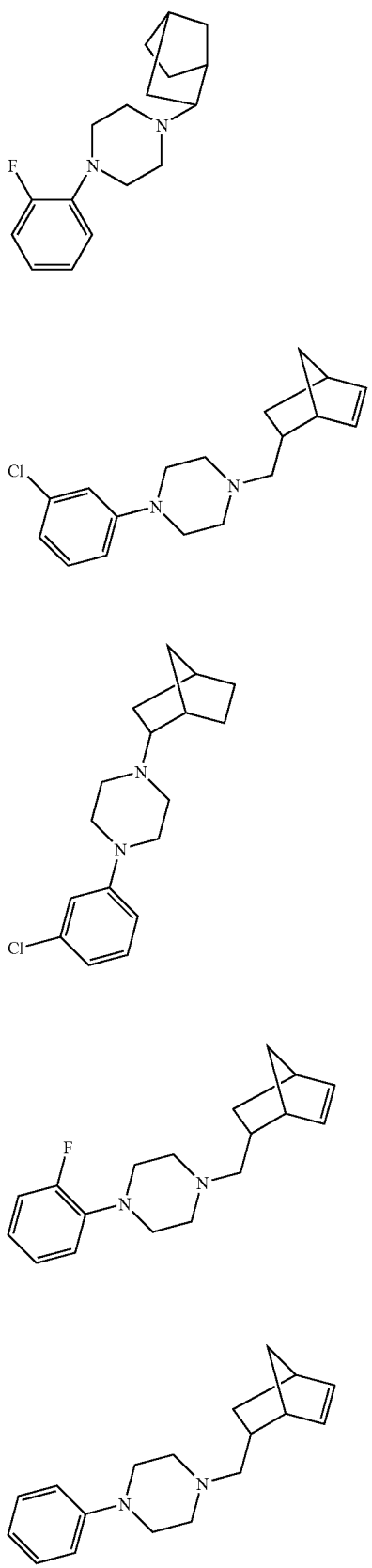
21. The compound of claim 18 selected from
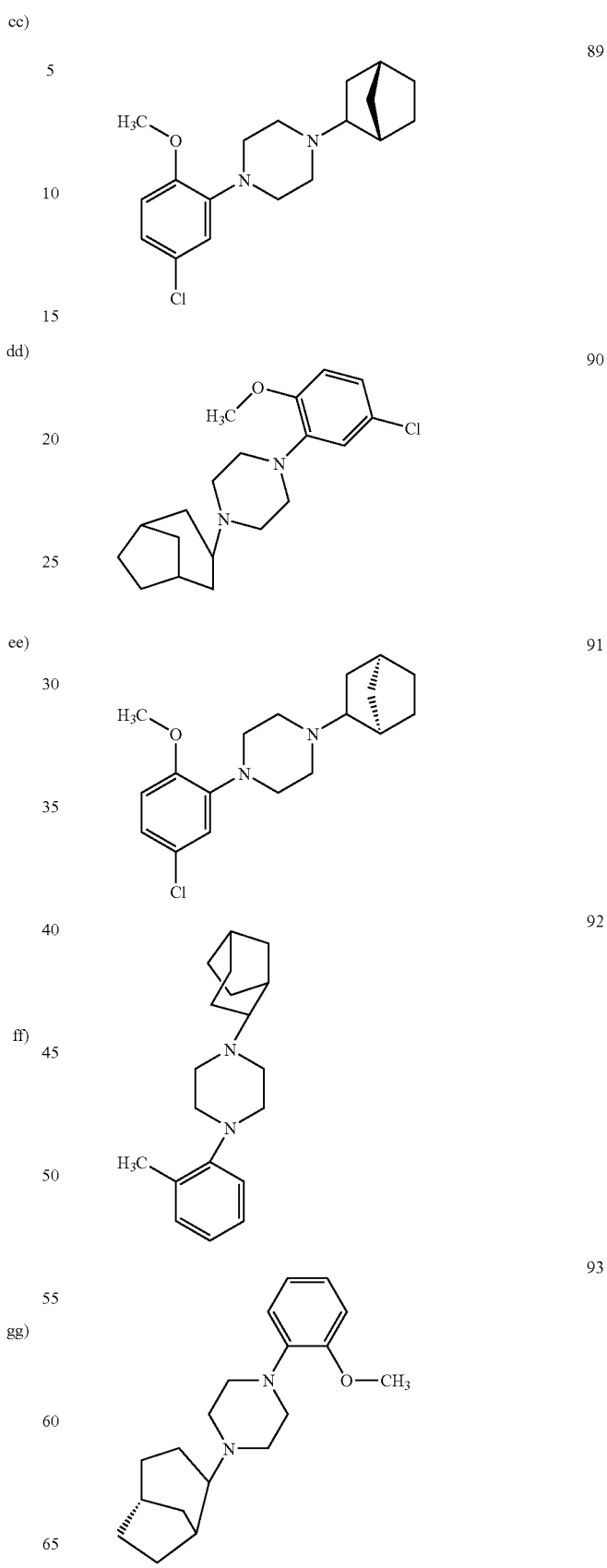

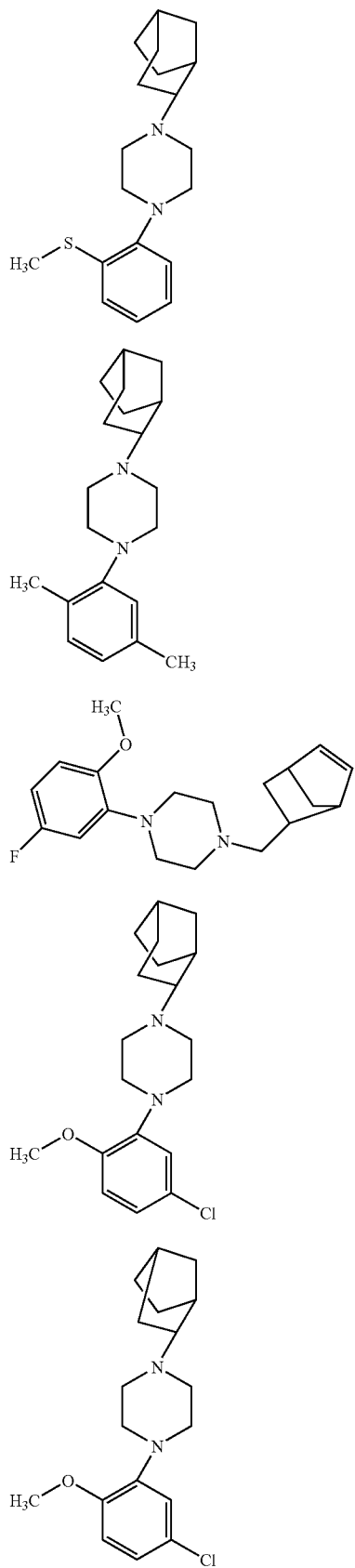
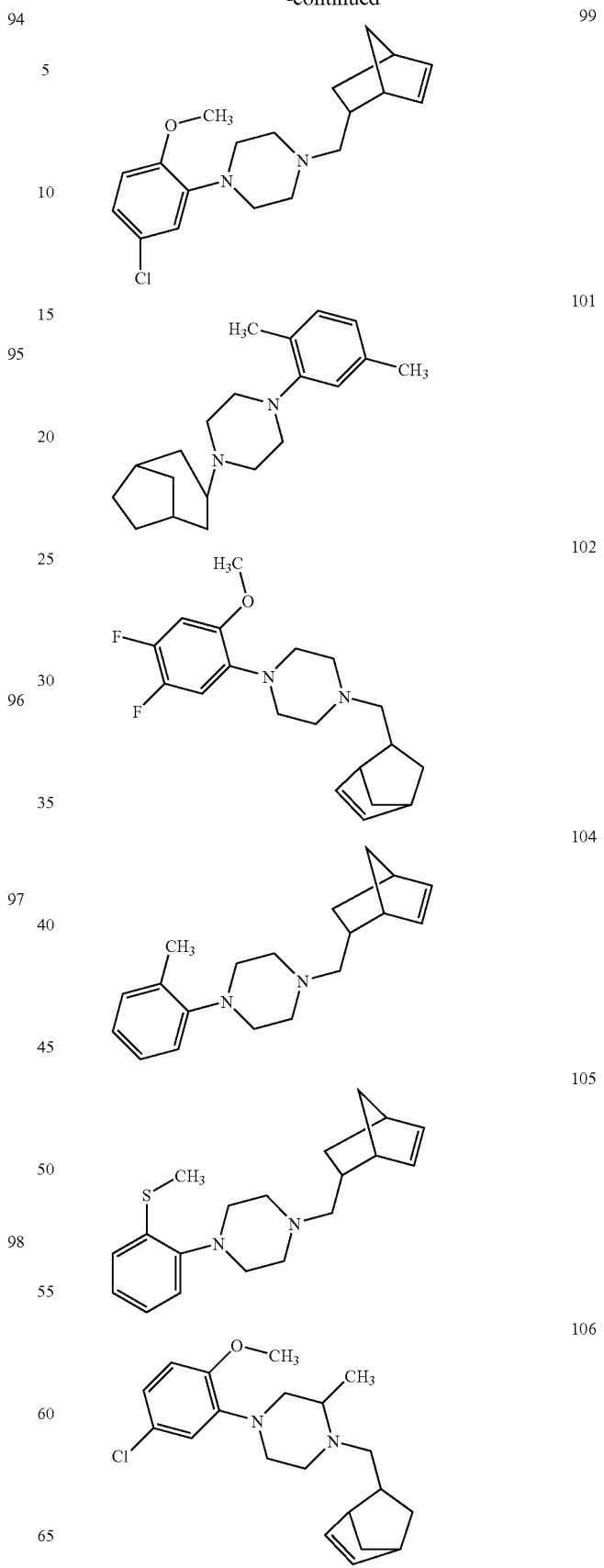

107 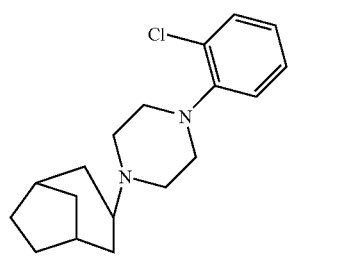
108 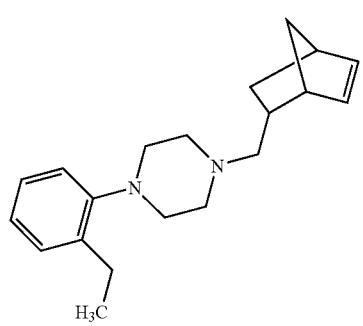
109 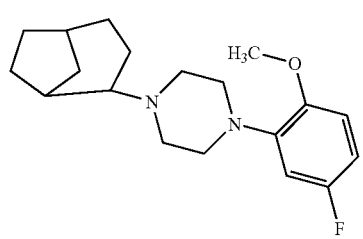
112 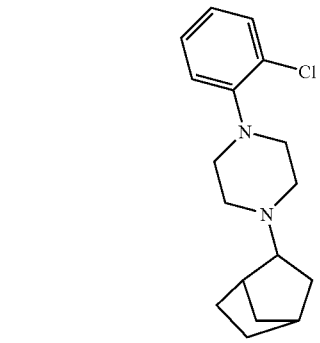
114 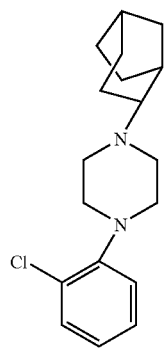
115 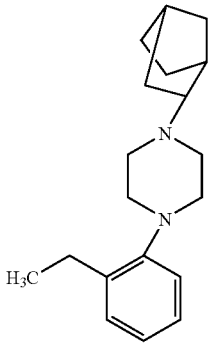
116 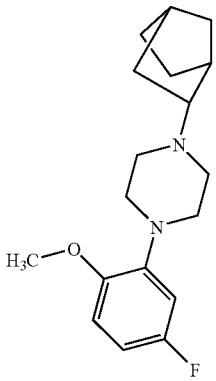
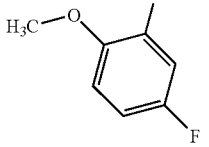
119 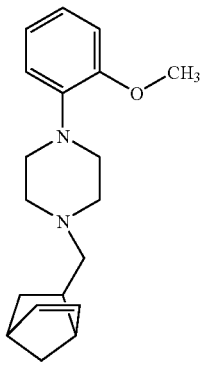
121 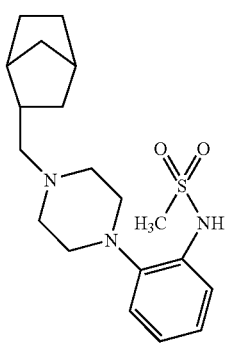

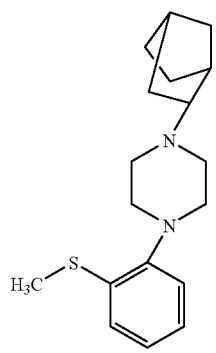
122
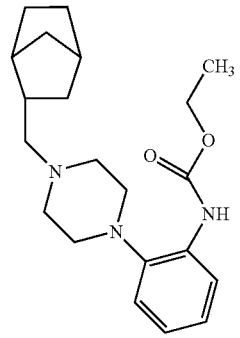
128
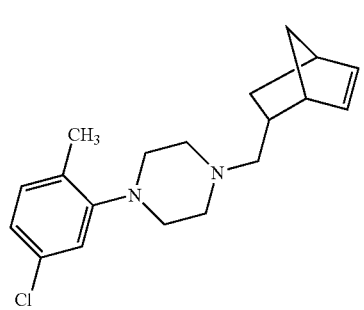
125
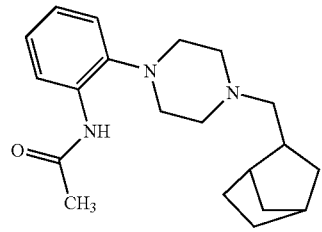
129
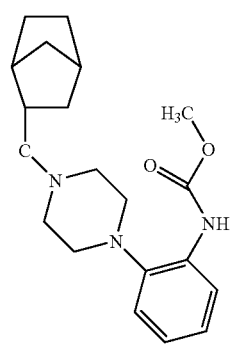
130
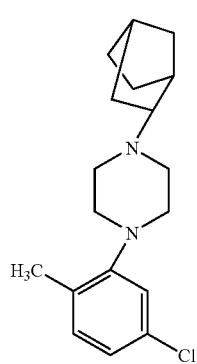
126
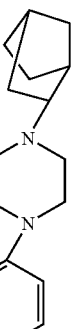
131
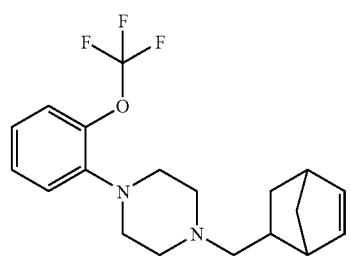
127
132

-continued
134
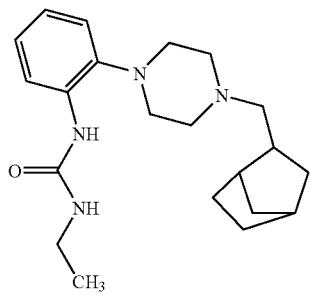
135
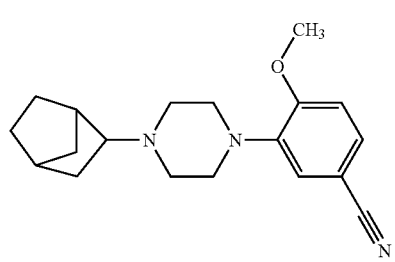
136
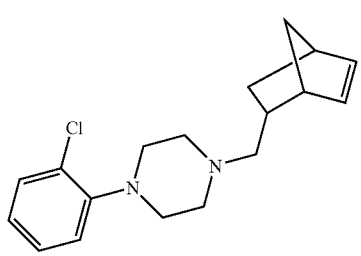
139
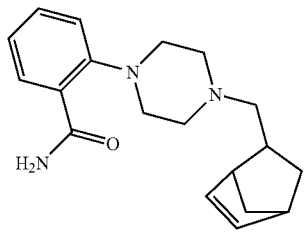
140
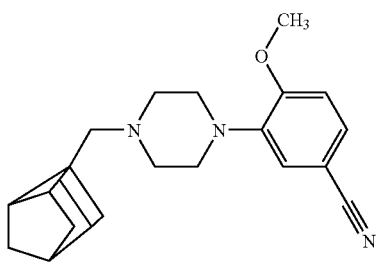
142
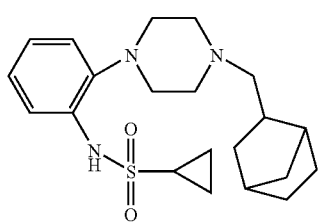
-continued
143
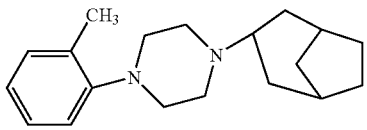
145
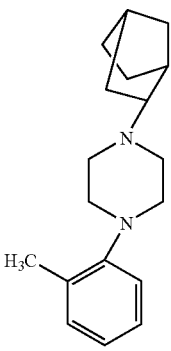
146
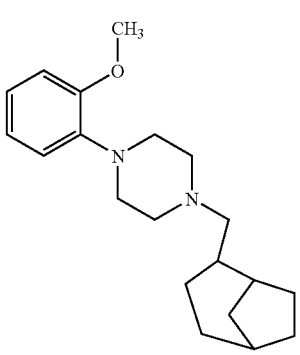
147
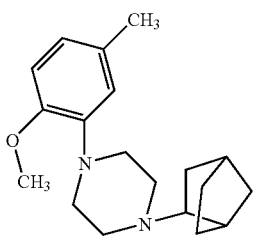
148
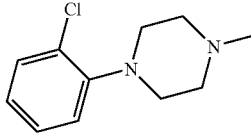
149
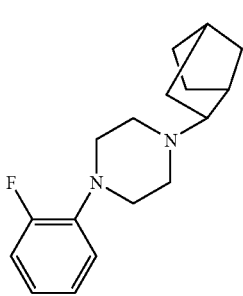

150 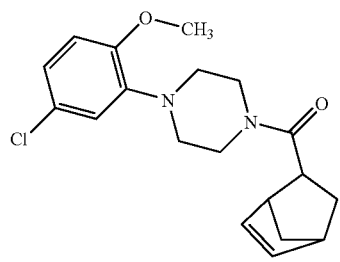
153 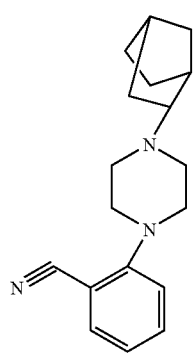
155 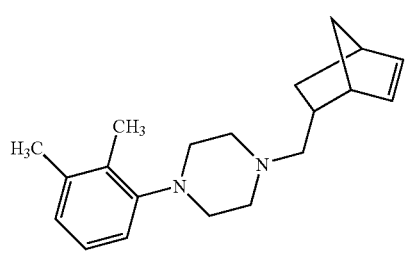
157 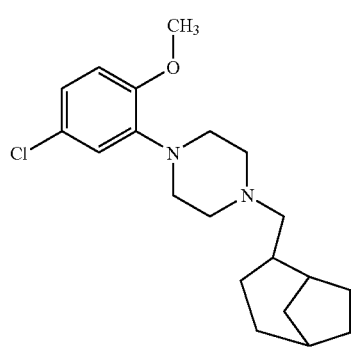
158 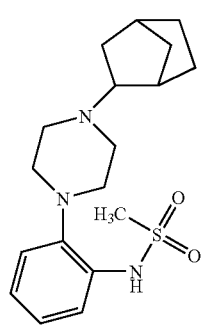
160 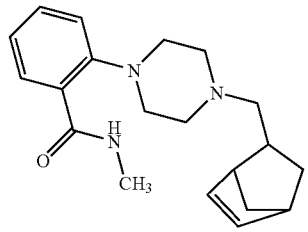
161 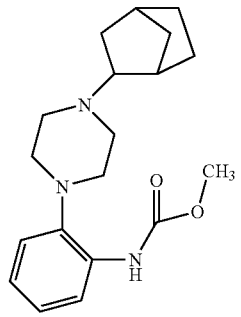
162 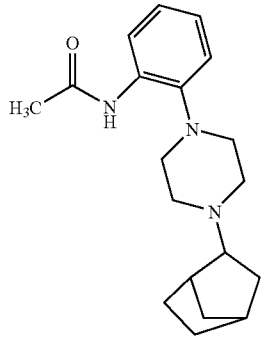
163 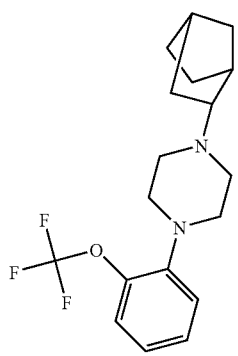
166 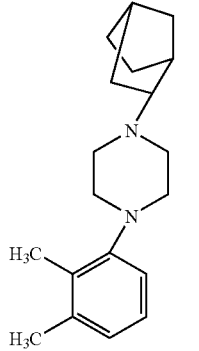

-continued
169 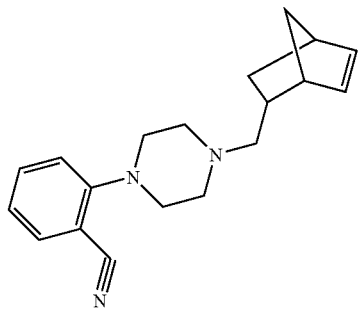
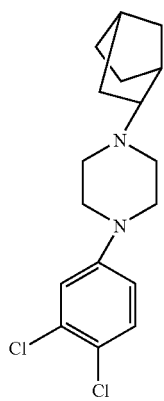
170
178 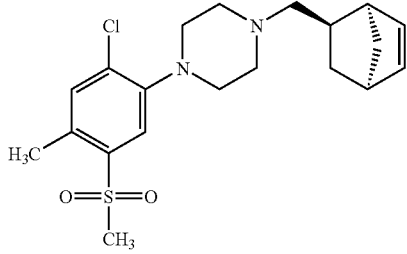
179
175 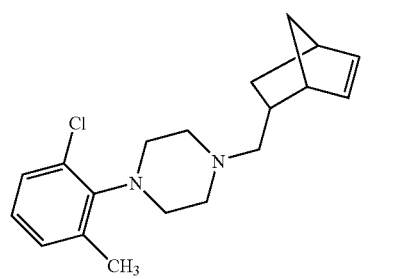
180 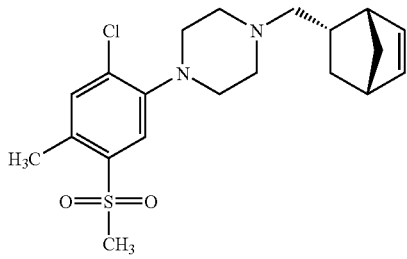
176 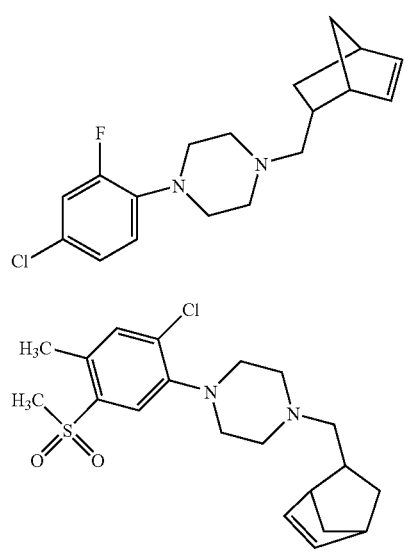
181 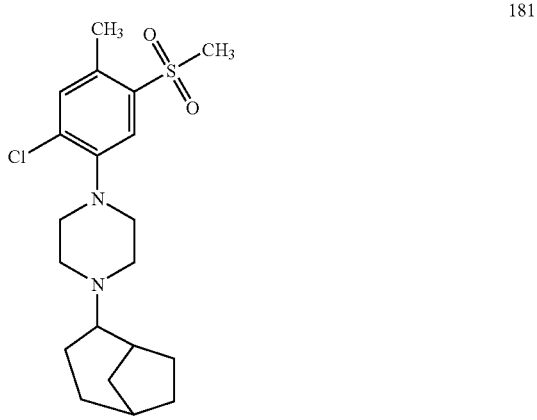
177

-continued
182
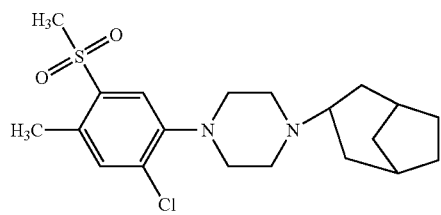
190
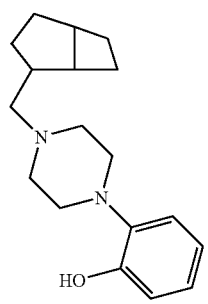
-continued
191
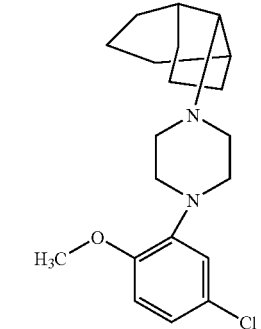
192
22. A pharmaceutical composition comprising a compound a compound according to claim 1 and a pharmaceutical carrier.
* * * * *